United States Patent
Kato et al.

(10) Patent No.: US 8,519,136 B2
(45) Date of Patent: Aug. 27, 2013

(54) AMINOPYRIDINE DERIVATIVES HAVING AURORA A SELECTIVE INHIBITORY ACTION

(75) Inventors: Tetsuya Kato, Tsukuba (JP); Nobuhiko Kawanishi, Moriya (JP); Takashi Mita, Tsukuba (JP); Katsumasa Nonoshita, Tsukuba (JP); Mitsuru Ohkubo, Ushiku (JP)

(73) Assignee: MSD K.K., Chiyoda-Ku, Tokyo (JP)

( * ) Notice: Subject to any disclaimer, the term of this patent is extended or adjusted under 35 U.S.C. 154(b) by 265 days.

(21) Appl. No.: 12/866,955

(22) PCT Filed: Feb. 18, 2009

(86) PCT No.: PCT/JP2009/053312
§ 371 (c)(1),
(2), (4) Date: Aug. 10, 2010

(87) PCT Pub. No.: WO2009/104802
PCT Pub. Date: Aug. 27, 2009

(65) Prior Publication Data
US 2011/0003833 A1    Jan. 6, 2011

Related U.S. Application Data

(60) Provisional application No. 61/066,724, filed on Feb. 22, 2008.

(51) Int. Cl.
*C07D 413/14*    (2006.01)
*C07D 401/14*    (2006.01)
*A61K 31/4525*    (2006.01)
*A61K 31/454*    (2006.01)

(52) U.S. Cl.
USPC .......................................... 546/194; 514/318

(58) Field of Classification Search
USPC .......................................... 546/194; 514/318
See application file for complete search history.

(56) References Cited

U.S. PATENT DOCUMENTS
2008/0027042 A1    1/2008    Ohkubo et al.

FOREIGN PATENT DOCUMENTS
| JP | 2004517927 | 6/2004 |
| WO | 2006046734 A2 | 5/2006 |
| WO | 2006046735 A1 | 5/2006 |
| WO | 2008026768 A1 | 3/2008 |

OTHER PUBLICATIONS
Simone, Oncology: Introduction, Cecil Textbook of Medicine, 20th Edition, 1996 vol. 1, pp. 1004-1010.*
Trisha Gura "Cancer Models: Systems for Identifying New Drugs Are Often Faulty" Science Nov. 7, 1997: vol. 278. No. 5340, pp. 1041-1042.*
Wakefield, Basil "Fluorinated Pharmaceuticals" Innovations in Pharmaceutical Technology 2003, 74, 76-78.*

* cited by examiner

*Primary Examiner* — David K O Dell
(74) *Attorney, Agent, or Firm* — Yong Zhao; David A. Muthard; Matthew A. Leff

(57) ABSTRACT

The present invention relates to a compound of formula I: wherein: $R_1$ is a hydrogen atom, F, CN, etc.; $R_2$ is CO, $SO_2$, etc.; $R_3$ is a phenyl which may be substituted; $X_1$, $X_2$, and $X_3$ each independently CH, N, etc. provided, however, that among $X_1$, $X_2$ and $X_3$, the number of nitrogen is 0 or 1; W is the following residue: wherein: $W_1$, $W_2$, and $W_3$ each independently CH, N, etc., or a pharmaceutically acceptable salt or ester thereof.

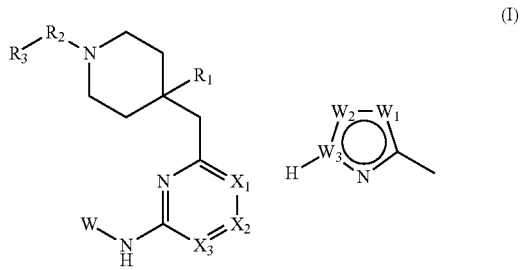

8 Claims, No Drawings

AMINOPYRIDINE DERIVATIVES HAVING AURORA A SELECTIVE INHIBITORY ACTION

REFERENCE TO SEQUENCE LISTING SUBMITTED ELECTRONICALLY

The sequence listing of the present application is being submitted electronically via EFS-Web as an ASCII formatted sequence listing with a file name "BANONC0237-SE-QLIST", creation date of Aug. 9, 2010 and a size of 991 bytes. This sequence listing submitted via EFS-Web is part of the specification and is herein incorporated by reference in its entirety.

TECHNICAL FIELD

The present invention relates to novel aminopyridine derivatives which are useful in the pharmaceutical field, and more particularly, to those which inhibit the growth of tumor cells based on an Aurora A selective inhibitory action and exhibit an antitumor effect, and also to an Aurora A selective inhibitor and an antitumor agent containing them.

BACKGROUND ART

Aurora kinase is a serine/threonine kinase involved in cell division. With regard to the Aurora kinase, three subtypes of A, B and C are known at present, and they have very high homology to each other. Aurora A participates in the maturation and distribution of centrosome or in the formation of spindle body. On the other hand, it is believed that Aurora B participates in the aggregation and pairing of chromosome, a spindle checkpoint and cytoplasm division [*Nat. Rev. Mol. Cell. Biol.*, No. 4, pp. 842-854]. Also, it is believed that Aurora C acts similarly as a result of interaction with Aurora B [*J. Biol. Chem.*, Epub ahead (2004)]. From the fact that high expression of Aurora A has been hitherto confirmed in many cancer cells; that high expression of Aurora A in normal cells leads to transformation of normal cell strains of rodent; and the like, Aurora A, being one of oncogenes, is recognized to be an adequate target for an antitumor agent [*EMBO J.*, No. 17, pp. 3052-3065 (1998)].

There is another report that cancer cells in which Aurora A is highly expressed have a resistance to paclitaxel [*Cancer Cell*, Vol. 3, pp. 51-62 (2003)]. Meanwhile, with regard to the Aurora kinase inhibitor, development of subtype-selective drugs has been thought to be difficult in view of high homology among subtypes, protein structure analysis and the like; and although there have been known reports on drugs such as ZM447439 which inhibit both Aurora A and Aurora B at the same time [*J. Cell Biol.*, No. 161, pp. 267-280 (2003); *J. Cell Biol.*, No. 161, pp. 281-294, (2003); *Nat. Med.*, No. 10, pp. 262-267, (2004)], no report concerning Aurora A selective drugs have been known. Thus, in those reports, disclosed is the antitumor effect only for the case where a drug which inhibits both Aurora A and Aurora B at the same time is solely administered. In addition, there has been also reported a result that in a drug which inhibits both Aurora A and Aurora B at the same time, the Aurora kinase inhibiting action attenuates the action of paclitaxel [*J. Cell Biol.*, No. 161, pp. 281-294, (2003)].

Now, patent applications concerning compounds having an Aurora kinase inhibiting action have been previously filed (WO 02/057259, U.S. Pat. No. 6,664,247, etc.), and patent applications concerning aminopyridine derivatives has been filed as well (U.S. Pat. No. 6,586,424, etc.). Under these circumstances, the present inventors filed a patent application directed to an aminopyridine derivative having an excellent Aurora A selective inhibitory action (WO2006/046734).

DISCLOSURE OF THE INVENTION

The problems that the present invention should solve are to create novel aminopyridine derivatives which show an excellent Aurora A selective inhibitory action and cell-growth inhibitory action based on the foregoing, as well as achieve a synergistic action by a combined use with other antitumor agent(s). Further, it is also the problems that the present invention should solve, to create, in the case of oral administration, novel aminopyridine derivatives which show an excellent Aurora A selective inhibitory action.

In order to solve the above problems, the present inventors have synthesized a variety of novel aminopyridine derivatives and found that the compound represented by the following Formula (I) shows an excellent Aurora A selective inhibitory action and cell-growth inhibitory action based on the foregoing, and also achieves a synergistic action by a combined use with other antitumor agents, thus completing the invention. With regard to those cancers which have been unable to be completely treated with known antitumor agents such as paclitaxel because it has been impossible to use a sufficient amount of the agents owing to side-effects or drug resistance thereof, the oral administration of the compound according to the invention or the combined administration of the compound according to the invention with other antitumor agent is expected to exhibit an excellent antitumor effect (including potentiation of action due to the other antitumor agent) and an effect of attenuating side-effects.

Thus, the invention relates to a compound of general formula I:

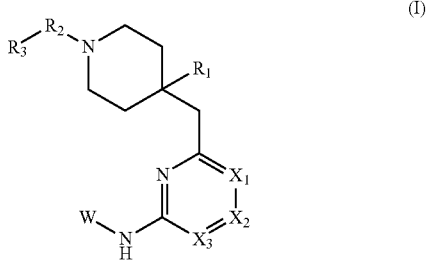

wherein:

$R_1$ is a hydrogen atom, F, CN, $COOR_{a1}$, $CONR_{a2}R_{a2}'$, $NR_{a3}COR_{a3}'$, $CONR_{a4}OR_{a4}'$, $NR_{a5}CONR_{a5}'R_{a5}''$, $NR_{a6}COOR_{a6}'$, $SO_2NR_{a7}R_{a7}'$, $NR_{a8}SO_2R_{a8}'$, $COR_{a9}$, $SO_2R_{a10}$, $NO_2$, $OR_{a11}$, $NR_{a12}R_{a12}'$, a lower alkyl which may be substituted, or a heterocyclic group which may be substituted, wherein:

$R_{a1}$, $R_{a3}$, $R_{a4}$, $R_{a5}$, $R_{a6}$, and $R_{a8}$ are each independently a hydrogen atom or lower alkyl which may be substituted;

$R_{a2}$, $R_{a2}'$, $R_{a5}'$, $R_{a5}''$, $R_{a7}$, $R_{a7}'$, $R_{a12}$, and $R_{a12}'$ are each independently a hydrogen atom or lower alkyl which may be substituted, provided, however, that $R_{a2}$ and $R_{a2}'$; $R_{a5}'$ and $R_{a5}''$; $R_{a7}$ and $R_{a7}'$; and $R_{a12}$ and $R_{a12}'$ each independently, together with the nitrogen atom which they bind to, may form a heterocyclic group which may be substituted;

$R_{a3}'$, $R_{a4}'$, $R_{a6}'$, $R_{a8}'$, $R_{a9}$, $R_{a10}$ and $R_{a11}$ are each independently a hydrogen atom or lower alkyl which may be substituted;

$R_2$ is CO, $SO_2$, or $CHR_x$ wherein $R_x$ is $CF_3$, CN, $COR_{x1}$, $COOR_{x2}$, $CONR_{x3}R_{x3}'$, $SO_2R_{x4}$, or $SO_2NR_{x5}R_{x5}'$; and $R_{x1}$, $R_{x2}$ and $R_{x4}$ are each independently a hydrogen atom or lower alkyl which may be substituted; and $R_{x3}$, $R_{x3}'$, $R_{x5}$ and $R_{x5}'$ are each independently a hydrogen atom or lower alkyl which may be substituted, provided, however, that $R_{x3}$ and $R_{x3}'$, and $R_{x5}$ and $R_{x5}'$, each independently, together with the nitrogen atom which they bind to, may form a heterocyclic group which may be substituted;

$R_3$ is a phenyl which may be substituted;

$X_1$ is CH, $CX_{1a}$, or N wherein $X_{1a}$ is a lower alkyl which may be substituted;

$X_2$ is CH, $CX_{2a}$, or N wherein:

$X_{2a}$ is a lower alkyl; or $X_{2a}$ is a substituent selected from <substituent group $A_1$>, or lower alkyl which is substituted with one or more of the same or different substituents selected from <substituent group $A_1$>, wherein <substituent group $A_1$> is halogen atom; cyano; hydroxy; lower alkylamino; di-lower alkylamino; lower alkoxy which may be substituted with one or more hydroxy groups; lower alkylthio; and lower alkylsulfonyl; phenyl which may be substituted; or $X_{2a}$ is $COOR_{x10}$, $CONR_{x20}R_{x30}$, $NHCOR_{x10}$, $NHCONR_{x20}R_{x30}$, $NHSO_2NR_{x20}R_{x30}$, $NR_{x40}R_{x50}$, or $CH_2NR_{x40}R_{x50}$, wherein:

$R_{x10}$ is a hydrogen atom or lower alkyl which may be substituted;

$R_{x20}$ and $R_{x30}$, which may be the same or different, are each a hydrogen atom, lower alkyl which may be substituted, or cycloalkyl which may be substituted; or alternatively $R_{x20}$ and $R_{x30}$, together with the nitrogen atom to which they bond, form a 5- or 6-membered aliphatic heterocyclic group which contains at least one atom selected from N, O and S and which may be substituted; and $R_{x40}$ and $R_{x50}$, which may be the same or different, are a hydrogen atom, lower alkyl that may be substituted, or cycloalkyl that may be substituted; or $X_{2a}$ is a 5- to 6-membered aliphatic heterocyclic group which contains at least one atom selected from N, O and S and which may be substituted, wherein two hydrogen atoms that are bonded to the same carbon atom of the aliphatic heterocyclic group may be substituted with oxo and neighboring two carbon atoms constituting the aliphatic heterocyclic ring may form a double-bond; or a lower alkyl which is substituted with the aliphatic heterocyclic group; or $X_{2a}$ is a 5- to 6-membered aromatic heterocyclic group which contains at least one atom selected from N, O and S and which may be substituted; or a lower alkyl which is substituted with the aromatic heterocyclic group;

$X_3$ is CH, $CX_{3a}$, or N wherein $X_{3a}$ is a lower alkyl which may be substituted; provided, however, that among $X_1$, $X_2$ and $X_3$, the number of nitrogen is 0 or 1;

W is the following residue:

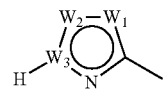

wherein:

$W_1$ is CH, N, NH, O, or S;

$W_2$ is CH, $CW_{2a}$, N, $NW_{2b}$, O or S, wherein $W_{2a}$ and $W_{2b}$ are each independently a hydrogen atom, halogen atom, cyano, lower alkyl having one to two carbon atoms, cycloalkyl having three to five carbon atoms, or lower alkyl having one to two carbon atoms which may be substituted with one or more halogen atoms;

$W_3$ is C or N; and at least one of $W_1$, $W_2$, and $W_3$ is a carbon atom; however, two of $W_1$, $W_2$, and $W_3$ are not simultaneously O and S, or a pharmaceutically acceptable salt or ester thereof.

The invention also relates to a combined preparation for simultaneous, separate or sequential administration in the treatment of cancer, comprising two separate preparations which are:

(i) a preparation comprising, together with a pharmaceutically acceptable carrier or diluent, a compound represented by the above-described Formula (I) or a pharmaceutically acceptable salt or ester thereof; and (ii) a preparation comprising, together with a pharmaceutically acceptable carrier or diluent, one antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents as well as pharmaceutically acceptable salt(s) or ester(s) thereof, wherein:

the antitumor alkylating agent is nitrogen mustard N-oxide, cyclophosphamide, ifosfamide, melphalan, busulfan, mitobronitol, carboquone, thiotepa, ranimustine, nimustine, temozolomide or carmustin;

the antitumor antimetabolite is methotrexate, 6-mercaptopurine riboside, mercaptopurine, 5-fluorouracil, tegafur, doxyfluridine, carmofur, cytarabine, cytarabine ocfosfate, enocitabine, S-1, gemcitabine, fludarabine or pemetrexed disodium;

the antitumor antibiotic is actinomycin D, doxorubicin, daunorubicin, neocarzinostatin, bleomycin, peplomycine, mitomycin C, aclarubicin, pirarubicin, epirubicin, zinostatin stimalamer, idarubicin, sirolimus or valrubicin;

the plant-derived antitumor agent is vincristine, vinblastine, vindesine, etoposide, sobuzoxane, docetaxel, paclitaxel or vinorelbine;

the antitumor platinum coordination compound is cisplatin, carboplatin, nedaplatin or oxaliplatin;

the antitumor camptothecin derivative is irinotecan, topotecan or camptothecin;

the antitumor tyrosine kinase inhibitor is gefitinib, imatinib, sorafenib, sunitinib, dasatinib, or erlotinib;

the monoclonal antibody is cetuximab, rituximab, bevacizumab, alemtuzumab or trastuzumab;

the interferon is interferon α, interferon α-2a, interferon α-2b, interferon β, interferon γ-1a or interferon γ-n1;

the biological response modifier is krestin, lentinan, sizofuran, picibanil or ubenimex; and the other antitumor agent is mitoxantrone, L-asparaginase, procarbazine, dacarbazine, hydroxycarbamide, pentostatin, tretinoin, alefacept, darbepoetin alfa, anastrozole, exemestane, bicalutamide, leuprolelin, flutamide, fulvestrant, pegaptanib octasodium, denileukin diftitox, aldesleukin, thyrotropin alfa, arsenic trioxide, bortezomib, capecitabine or goserelin.

The invention further relates to a pharmaceutical composition comprising, together with a pharmaceutically acceptable carrier or diluent, a compound represented by the above-described Formula (I) or a pharmaceutically acceptable salt or ester thereof, and an antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, biological response modifiers and other antitumor agents (here, the definition of each antitumor agent is the same as that defined hereinabove) or a pharmaceutically acceptable salt or ester thereof.

The invention still further relates to a method for the treatment of cancer, comprising administering simultaneously, separately or sequentially a therapeutically effective amount of a compound represented by the above-described Formula (I) or a pharmaceutically acceptable salt or ester thereof in combination with a therapeutically effective amount of an antitumor agent selected from the group consisting of antitumor alkylating agents, antitumor antimetabolites, antitumor antibiotics, plant-derived antitumor agents, antitumor platinum coordination compounds, antitumor camptothecin derivates, antitumor tyrosine kinase inhibitors, monoclonal antibodies, interferons, biological response modifiers and other antitumor agents (here, definition of each antitumor agent is the same as that defined hereinabove) or a pharmaceutically acceptable salt or ester thereof.

Furthermore, the invention relates to the use of an Aurora selective A inhibitor for the manufacture of a medicament for the treatment of cancer; and the use of an Aurora selective A inhibitor in combination with an antitumor agent for the manufacture of a medicament for the treatment of cancer; and also relates to a method of treating cancer to a mammal (particularly a human) which comprises administering to said mammal a therapeutically effective amount of an Aurora selective A inhibitor; and a method of treating cancer in a mammal (particularly a human) which comprises administering to said mammal a therapeutically effective amount of an Aurora selective A inhibitor in combination with a therapeutically effective amount of an antitumor agent.

The invention relates to a pharmaceutical composition comprising as active ingredient an Aurora selective A inhibitor; and a pharmaceutical composition comprising as active ingredient an Aurora selective A inhibitor, together with an antitumor agent.

Next, symbols and terms used in the present specification will be explained.

The term "lower alkyl" in the above Formula (I) denotes a linear or branched alkyl group having 1 to 6 carbon atoms, and examples thereof include, for example, methyl, ethyl, propyl, isopropyl, butyl, isobutyl, sec-butyl, tert-butyl, pentyl and hexyl, among these methyl being preferred.

The term "cycloalkyl" in the above Formula (I) denotes a 3- to 8-membered aliphatic cyclic group such as, for example, cyclopropyl, cyclobutyl, cyclopentyl, cyclohexyl, cycloheptyl and cyclooctyl.

The "heterocyclic group" in the Formula (I) refers to an "aromatic heterocyclic group" or "aliphatic heterocyclic group". Here, the "aromatic heterocyclic group" refers to an aromatic heterocyclic group containing, in addition to a carbon atom(s), at least one heteroatom such as a nitrogen atom, an oxygen atom or the like, and examples thereof include a 5- to 7-membered monocyclic heterocyclic group, a fused-ring heterocyclic group formed by fusion of a 3- to 8-membered ring to the monocyclic heterocyclic group, and the like. Specifically, a thienyl group, a pyrrolyl group, a thiazolyl group, an imidazolyl group, a pyrazolyl group, an oxazolyl group, a pyridyl group, a pyrazinyl group, a pyrimidinyl group, a pyridazinyl group, an isoxazolyl group, an isoquinolyl group, an isoindolyl group, an indazolyl group, an indolyl group, a quinoxalinyl group, a quinolyl group, a benzoimidazolyl group, a benzofuranyl group and the like may be mentioned. On the other hand, the "aliphatic heterocyclic group" refers to a saturated or unsaturated aliphatic heterocyclic group containing, in addition to a carbon atom(s), at least one atom selected from a nitrogen atom, an oxygen atom and a sulfur atom in addition to carbon atoms, and having a monocyclic ring or a bicyclic or tricyclic fused ring. Examples thereof include an azetidyl group, a pyrrolidinyl group, a piperidinyl group, a piperazinyl group, a morpholino group, a tetrahydrofuranyl group, an imidazolidinyl group, a thiomorpholino group, a tetrahydroquinolyl group, a tetrahydroisoquinolyl group and the like.

The term "5- or 6-membered aliphatic heterocyclic group" in the above Formula (I) denotes a 5- or 6-membered aliphatic cyclic group containing at least one atom selected from nitrogen atom, oxygen atom and sulfur atom in addition to carbon atoms, and examples thereof include pyrrolidinyl, piperidinyl, piperazinyl, morpholino, tetrahydrofuranyl, imidazolidinyl and thiomorpholino. Further, for the aliphatic heterocyclic group, two hydrogen atoms which are bonded to the same carbon atom may be substituted with an oxo group, and also, adjacent carbon atoms constituting the ring of the aliphatic heterocyclic group may be double-bonded.

The term "5- or 6-membered aromatic heterocyclic group" in the above Formula (I) denotes a 5- or 6-membered aromatic cyclic group containing at least one atom selected from nitrogen atom, oxygen atom and sulfur atom in addition to carbon atoms, and examples thereof include thienyl, pyrrolyl, furyl, thiazolyl, imidazolyl and oxazolyl.

The term "halogen atom" in the above Formula (I) is, for example, fluorine atom, chlorine atom, bromine atom or iodine atom. Among them, for example, fluorine atom, chlorine atom or bromine atom is preferred.

The term "lower alkylamino" in the above Formula (I) denotes a group in which amino is N-substituted with the above-described "lower alkyl", and examples thereof include N-methylamino, N-ethylamino, N-propylamino, N-isopropylamino, N-butylamino, N-isobutylamino, N-tert-butylamino, N-pentylamino and N-hexylamino.

The term "di-lower alkylamino" in the above Formula (I) denotes a group in which amino is N,N-disubstituted with the above-described "lower alkyl", and examples thereof include N,N-dimethylamino, N,N-diethylamino, N,N-dipropylamino, N,N-diisopropylamino, N,N-dibutylamino, N,N-diisobutylamino, N,N-di-tert-butylamino, N,N-dipentylamino, N,N-dihexylamino, N-ethyl-N-methylamino and N-methyl-N-propylamino.

The term "lower alkylsulfonyl" in the above Formula (I) denotes a group in which the above-described "lower alkyl" is bonded to sulfonyl, and examples thereof include methylsulfonyl, ethylsulfonyl and butylsulfonyl.

The term "lower alkylsulfonylamino" in the above Formula (I) denotes a group in which the above-described "lower alkylsulfonyl" is bonded to amino, and examples thereof include methylsulfonylamino, ethylsulfonylamino and butylsulfonylamino.

The term "lower alkoxy" in the above Formula (I) denotes a group in which "lower alkyl" is bonded to oxygen atom, and examples thereof include methoxy, ethoxy, propoxy, isopropoxy, butoxy, isobutoxy, sec-butoxy, tert-butoxy, pentyloxy, neopentyloxy, hexyloxy and isohexyloxy.

The term "lower alkoxycarbonyl" in the above Formula (I) denotes a group in which "lower alkoxy" is bonded to carbonyl, and examples thereof include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, neopentyloxycarbonyl, hexyloxycarbonyl and isohexyloxycarbonyl.

The term "lower alkoxycarbonylamino" in the above Formula (I) denotes a group in which "lower alkoxycarbonyl" is bonded to amino, and examples thereof include methoxycarbonylamino, ethoxycarbonylamino, propoxycarbonylamino, isopropoxycarbonylamino, butoxycarbonylamino, isobutoxycarbonylamino, sec-butoxycarbonylamino, tert-butoxycarbonylamino, pentyloxycarbonylamino, neopentyloxycarbonylamino, hexyloxycarbonylamino and isohexyloxycarbonylamino.

The term "lower alkanoyl" in the above Formula (I) denotes a group in which the above-described "lower alkyl" is bonded to carbonyl, and examples thereof include acetyl, propionyl, butyryl, isobutyryl, valeryl, isovaleryl, pivaloyl and pentanoyl.

The term "lower alkanoyloxy" in the above Formula (I) denotes a group in which the above-described "lower alkanoyl" is bonded to an oxygen atom, and examples thereof include acetyloxy, propionyloxy, butyryloxy, isobutyryloxy, valeryloxy, isovaleryloxy, pivaloyloxy and pentanoyloxy.

The term "lower alkylthio" in the above Formula (I) denotes a substituent in which the above-described "lower alkyl" is bonded to sulfur atom, and examples thereof include methylthio, ethylthio and butylthio.

The term "selective inhibitor of Aurora A" used in the present specification is a compound or a drug which selectively inhibits Aurora A as compared with Aurora B. The "selective inhibitor of Aurora A" is preferably a compound or a drug of which inhibitory activities against Aurora A are at least ten times the activities against Aurora B; and more preferably a compound or a drug of which inhibitory activities against Aurora A are at least hundred times the activities against Aurora B.

Explanation for the term "pharmaceutically acceptable salt of ester thereof" or the term "pharmaceutically acceptable carrier or diluent" used in the specification still will be given later.

The term "treatment of cancer" as used in the specification means inhibition of cancer cell growth by administering an antitumor agent to a cancer patient. Preferably, this treatment enables retrogression of cancer growth, that is, reduction in the measurable cancer size. More preferably, such treatment completely eliminates cancer.

The term "cancer" as used in the specification refers to solid cancer and hematopoietic cancer. Here, examples of solid cancer include cerebral tumor, head and neck cancer, esophageal cancer, thyroid cancer, small cell lung cancer, non-small cell lung cancer, breast cancer, stomach cancer, gallbladder and bile duct cancer, liver cancer, pancreas cancer, colon cancer, rectal cancer, ovarian cancer, chorioepithelioma, uterine cancer, cervical cancer, renal pelvic and ureteral cancer, bladder cancer, prostate cancer, penile cancer, testicular cancer, embryonal cancer, wilms tumor, skin cancer, malignant melanoma, neuroblastoma, osteosarcoma, Ewing's tumor and soft tissue sarcoma. On the other hand, examples of hematopoietic cancer include acute leukemia, chronic lymphatic leukemia, chronic myelocytic leukemia, polycythemia vera, malignant lymphoma, multiple myeloma and non-Hodgkins' lymphoma.

The term "preparation" as used in the specification includes oral preparations and parenteral preparations. Examples of oral preparations include tablets, capsules, powders and granules, while examples of parenteral preparations include sterilized liquid preparations such as solutions or suspensions, specifically injections or drip infusions. Preferably, they are intravenous injections or intravenous drip infusions, and more preferably intravenous drip infusions.

The term "combined preparation" as used in the specification refers to those comprising two or more preparations for simultaneous, separate or sequential administration in the treatment, and such preparation may be a so-called kit type preparation or pharmaceutical composition. The term "combined preparation" also includes those having one or more preparations further combined with the combined preparation comprising two separate preparations used in the treatment of cancer.

The two separate preparations described above can be further combined with, in combination with a pharmaceutically acceptable carrier or diluent, at least one preparation comprising at least one antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents (here, definition of each antitumor agent is the same as that defined above), or a pharmaceutically acceptable salt or ester thereof. In this case, the above-mentioned at least one preparation that has been further combined can be administered simultaneously, separately or sequentially with respect to the two separate preparations. For example, a combined preparation comprising three preparations may include that is comprised of a preparation including a preparation containing the compound represented by the above Formula (I), a preparation containing 5-fluorouracil and a preparation containing leucovorin.

Here, in the above-mentioned combined preparation, either or both of the two separate preparations may be an oral preparation; and also one may be an oral preparation, while another may be a parental preparation (injections or drip infusions).

The term "preparation" according to the invention may usually comprise a therapeutically effective amount of a compound according to the invention, together with a pharmaceutically acceptable carrier or diluent. This technique of formulation is considered to be a technical common knowledge to those having ordinary skill in the pertinent art and is well known. Preferably, oral preparations, intravenous drip infusions or injections can be prepared in combination with a pharmaceutically acceptable carrier or diluent, by various methods that are well known in the art.

In the case of using the combined preparation according to the invention, the term "administration" as used in the present specification refers to parenteral administration and/or oral administration, and preferably oral administration. Thus, when a combined preparation is administered, both administrations may be parenteral; one administration may be parenteral while the other may be oral; or both administrations may be oral. Preferably, both preparations in the combined preparation are administered orally. Here, the term "parenteral administration" is, for example, intravenous administration, subcutaneous administration or intramuscular administration, and preferably it is intravenous administration. Even when three or more preparations are combined and administered, every preparation may be orally administered.

In the embodiment of the present invention, a compound represented by the above Formula (I) may be administered simultaneously with other antitumor agent(s). Further, it is possible to administer the compound represented by the above Formula (I) first and then another antitumor agent consecutively, or alternatively it is possible to administer another antitumor agent first and then the compound represented by the above Formula (I) consecutively. It is also possible to administer the compound represented by the above Formula (I) first and then separately administer another antitumor agent after a while, or alternatively it is possible to administer another antitumor agent first and then separately administer the compound represented by the above Formula (I) after a while. The order and the time interval for the administration may be appropriately selected by a person skilled in the art in accordance with, for example, a preparation containing the compound represented by the above Formula (I) used and a preparation containing an antitumor agent that is used in combination therewith, the type of the cancer cells to be treated and the condition of the patient. For example, in the case of administering the compound represented by the above Formula (I) and paclitaxel or docetaxel, preferably paclitaxel or docetaxel is administered first, and then the compound represented by the above Formula (I) is administered sequentially or separately after a while.

The term "simultaneously" as used in the specification refers to the use of preparations for the treatment substantially at the same time, whereas the term "separately" refers to the separate use of preparations for the treatment at different times such that, for example, one agent is used on the first day and another agent is used on the second day for the treatment. The term "sequentially" refers to the use of preparations in such an order that, for example, one agent is first used and another agent is used after a predetermined period of time for the treatment.

The term "antitumor alkylating agent" as used in the present specification refers to an alkylating agent having antitumor activity, and the term "alkylating agent" herein generally refers to an agent giving an alkyl group in the alkylation reaction in which a hydrogen atom of an organic compound is substituted with an alkyl group. The term "antitumor alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "antitumor antimetabolite" as used in the specification refers to an antimetabolite having antitumor activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "antitumor antimetabolites" may be exemplified methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are 5-fluorouracil, S-1, gemcitabine and the like.

The term "antitumor antibiotic" as used in the specification refers to an antibiotic having antitumor activity, and the "antibiotic" herein includes substances that are produced by microorganisms or by organic synthesis and inhibit cell growth and other functions of microorganisms and of other living organisms. The term "antitumor antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin.

The term "plant-derived antitumor agent" as used in the specification includes compounds having antitumor activities which originate from plants, or compounds prepared by applying chemical modification to the foregoing compounds. The term "plant-derived antitumor agent" may be exemplified by vincristine, vinblastine, vindesine, etoposide, sobuzoxane, docetaxel, paclitaxel and vinorelbine, and preferred and docetaxel and paclitaxel.

The term "antitumor camptothecin derivative" as used in the specification refers to compounds that are structurally related to camptothecin and inhibit cancer cell growth, including camptothecin per se. The term "antitumor camptothecin derivative" is not particularly limited to, but may be exemplified by, camptothecin, 10-hydroxycamptothecin, topotecan, irinotecan or 9-aminocamptothecin, with camptothecin, topotecan and irinotecan being preferred. Further, irinotecan is metabolized in vivo and exhibits antitumor effect as SN-38. The action mechanism and the activity of the camptothecin derivatives are believed to be virtually the same as those of camptothecin (e.g., Nitta, et al., *Gan to Kagaku Ryoho,* 14, 850-857 (1987)).

The term "antitumor platinum coordination (platinum-complex) compound" as used in the specification refers to a platinum coordination compound having antitumor activity, and the term "platinum coordination compound" herein refers to a platinum coordination compound which provides platinum in ion form. Preferred platinum compounds include cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato) platinum (II) (carboplatin); spiroplatin; iproplatin; diammine(2-ethylmalonato)platinum (II); ethylenediamine-malonatoplatinum (II); aqua(1,2-diaminodicyclohexane)sulfatoplatinum (II); aqua(1,2-diaminodicyclohexane)malonatoplatinum (II); (1,2-diaminocyclohexane)malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred is carboplatin or oxaliplatin. Further, other antitumor platinum coordination compounds mentioned in the specification are known and are commercially available and/or producible by a person having ordinary skill in the art by conventional techniques.

The term "antitumor tyrosine kinase inhibitor" as used in the specification refers to a tyrosine kinase inhibitor having antitumor activity, and the term "tyrosine kinase inhibitor" herein refers to a chemical substance inhibiting "tyrosine kinase" which transfers a γ-phosphate group of ATP to a hydroxy group of a specific tyrosine in protein. The term "antitumor tyrosine kinase inhibitor" may be exemplified by gefitinib, imatinib, sorafenib, sunitinib, dasatinib, or erlotinib.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having antitumor activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine. Examples of "interferon" include interferon α, interferon α-2a, interferon α-2b, interferon β, interferon γ-1a and interferon γ-n1.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofuran, picibanil and ubenimex.

The term "other antitumor agent" as used in the specification refers to an antitumor agent which does not belong to any of the above-described agents having antitumor activities. Examples of the "other antitumor agent" include mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

The above-described terms "antitumor alkylating agent", "antitumor antimetabolite", "antitumor antibiotic", "plant-derived antitumor agent", "antitumor platinum coordination compound", "antitumor camptothecin derivative", "antitumor tyrosine kinase inhibitor", "monoclonal antibody", "interferon", "biological response modifier" and "other antitumor agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned antitumor alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from Glaxo-SmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned antitumor antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned antitumor antibiotics are commercially available, as exemplified by the following: actinomycin D from Banyu Pharmaceutical Co., Ltd. as Cosmegen (tradename); doxorubicin from Kyowa Hakko Kogyo Co., Ltd. as adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived antitumor agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxsotere (tadename); paclitaxel from Bristol-Myers Squibb Co. as Taxol (tradename); and vinorelbine from Kyowa Hakko Kogyo Co., Ltd. as Navelbine (tradename).

The above-mentioned antitumor platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned antitumor camptothecin derivatives are commercially available, as exemplified by the following:

irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned antitumor tyrosine kinase inhibitors are commercially available, as exemplified by the following: gefitinib from AstraZeneca Corp. as Iressa (tradename); imatinib from Novartis AG as Gleevec (tradename); sorafenib from Bayer as Nexavar (tradename); sunitinib from Pfizer as Sutent (tradename); dasatinib from Bristol Myers Squibb as Sprycel (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rituxan (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon α from Sumitomo Pharmaceutical Co., Ltd. as Sumiferon (tradename); interferon α-2a from Takeda Pharmaceutical Co., Ltd. as Canferon-A (tradename); interferon α-2b from Schering-Plough Corp. as Intron A (tradename); interferon β from Mochida Pharmaceutical Co., Ltd. as IFNβ (tradename); interferon γ-1a from Shionogi & Co., Ltd. as Immunomax-γ (tradename); and interferon γ-n1 from Otsuka Pharmaceutical Co., Ltd. as Ogamma (tradename).

The above-mentioned biological response modifiers are commercially available, as exemplified by the following: krestin from Sankyo Co., Ltd. as krestin (tradename); lentinan from Aventis Corp. as Lentinan (tradename); sizofuran from Kaken Seiyaku Co., Ltd. as Sonifuran (tradename); picibanil from Chugai Pharmaceutical Co., Ltd. as Picibanil (tradename); and ubenimex from Nippon Kayaku Co., Ltd. as Bestatin (tradename).

The above-mentioned other antitumor agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc. as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename).

The term "antitumor agent" as used in the specification includes the above-described "antitumor alkylating agent", "antitumor antimetabolite", "antitumor antibiotic", "plant-derived antitumor agent", "antitumor platinum coordination compound", "antitumor camptothecin derivative", "antitumor tyrosine kinase inhibitor", "monoclonal antibody", "interferon", "biological response modifier" and "other antitumor agent".

The term "aminopyridine derivative" as used in the specification includes, but is not limited to, any compound having a pyridyl group or a pyridine analogue group, any of which is substituted with an amino group. It is exemplified by a compound of the above General Formula (I), and preferably any one compound of the below-mentioned (a) to (f): a compound which is:

(a)         1-(3-chloro-2-fluorobenzoyl)-4-((6-(1H-pyrazol-3-ylamino)pyridin-2-yl)methyl)piperidin-4-ol (example 2);

(b)     5-(1-(2-fluoro-3-(trifluoromethyl)benzoyl)-4-((6-(1H-pyrazol-3-ylamino)pyridin-2-yl)methyl)piperidin-4-yl)-1,3,4-oxadiazol-2(3H)-one (example 9);

(c)     5-(1-(3-chloro-2-fluorobenzoyl)-4-((6-(1H-pyrazol-3-ylamino)pyridin-2-yl)methyl)piperidin-4-yl)-1,3,4-oxadiazol-2(3H)-one (example 10);

(d) 5-(4-((6-(1H-pyrazol-3-ylamino)pyridin-2-yl)methyl)-1-((2-(trifluoromethyl)phenyl)sulfonyl)piperidin-4-yl)-1,3,4-oxadiazol-2(3H)-one (example 14);

(e)     5-(1-(3-chloro-2-fluorobenzoyl)-4-((4-phenyl-6-(1H-pyrazol-3-ylamino)pyridin-2-yl)methyl)piperidin-4-yl)-1,3,4-oxadiazol-2(3H)-one (example 17); or (f) 5-(4-((6-(1H-pyrazol-3-ylamino)pyridin-2-yl)methyl)-1-(2,2,2-trifluoro-1-(3-(trifluoromethyl)phenyl)ethyl)piperidin-4-yl)-1,3,4-oxadiazol-2(3H)-one (example 19);

or a pharmaceutically acceptable salt or ester thereof.

Embodiments of the compound represented by the above General Formula (I) will be illustrated in more detail.

$R_1$ is a hydrogen atom, F, CN, $COOR_{a1}$, $CONR_{a2}R_{a2}'$, $NR_{a3}COR_{a3}'$, $CONR_{a4}OR_{a4}'$, $NR_{a5}CONR_{a5}'R_{a5}''$, $NR_{a6}COOR_{a6}'$, $SO_2NR_{a7}R_{a7}'$, $NR_{a8}SO_2R_{a8}'$, $COR_{a9}$, $SO_2R_{a10}$, $NO_2$, $OR_{a11}$, $NR_{a12}R_{a12}'$, a lower alkyl which may be substituted, or a heterocyclic group which may be substituted, wherein:

$R_{a1}$, $R_{a3}$, $R_{a4}$, $R_{a5}$, $R_{a6}$, and $R_{a8}$ are each independently a hydrogen atom or lower alkyl which may be substituted;

$R_{a2}$, $R_{a2}'$, $R_{a5}'$, $R_{a5}''$, $R_{a7}$, $R_{a7}'$, $R_{a12}$, and $R_{a12}'$ are each independently a hydrogen atom or lower alkyl which may be substituted, provided, however, that $R_{a2}$ and $R_{a2}'$; $R_{a5}'$ and $R_{a5}''$; $R_{a7}$ and $R_{a7}'$; and $R_{a12}$ and $R_{a12}'$ each independently, together with the nitrogen atom which they bind to, may form a heterocyclic group which may be substituted;

$R_{a3}'$, $R_{a4}'$, $R_{a6}'$, $R_{a8}'$, $R_{a9}$, $R_{a10}$ and $R_{a11}$ are each independently a hydrogen atom or lower alkyl which may be substituted;

Preferably, $R_1$ is a hydrogen atom, F, CN, $COOR_{a1}$, $CONR_{a2}R_{a2}'$, $NR_{a3}COR_{a3}'$, $CONR_{a4}OR_{a4}'$, $NR_{a5}CONR_{a5}'R_{a5}''$, $NR_{a6}COOR_{a6}'$, $SO_2NR_{a7}R_{a7}'$, $NR_{a8}SO_2R_{a8}'$, $COR_{a9}$, $SO_2R_{a10}$, $NO_2$, $OR_{a11}$, or $NR_{a12}R_{a12}'$, wherein:

$R_{a1}$, $R_{a3}$, $R_{a4}$, $R_{a5}$, $R_{a6}$, and $R_{a8}$ are each independently a hydrogen atom or lower alkyl;

$R_{a2}$, $R_{a2}'$, $R_{a5}'$, $R_{a5}s'''$, $R_{a7}$, $R_{a7}'$, $R_{a12}$, and $R_{a12}'$ are each independently a hydrogen atom or lower alkyl which may be substituted with one or more of the same or different substituents selected from <substituent group $L_1$>, wherein <substituent group $L_1$> is a halogen atom, hydroxy, nitro, cyano, amino, carbamoyl, aminosulfonyl, imino, lower alkylamino, di-lower alkylamino, lower alkylsulfonyl, lower alkylsulfonylamino, lower alkoxy, lower alkoxycarbonyl, lower alkoxycarbonylamino, lower alkanoyl, lower alkanoyloxy, lower alkylthio, and carboxyl; provided, however, that $R_{a2}$ and $R_{a2}'$; $R_{a5}'$ and $R_{a5}''$; $R_{a7}$ and $R_{a7}'$; and $R_{a12}$ and $R_{a12}'$ each independently, together with the nitrogen atom which they bind to, may form a 5-membered or 6-membered aromatic or aliphatic heterocyclic group which may be substituted with one or more of the same or different substituents selected from <substituent group $L_2$>, wherein <substituent group $L_2$> is a halogen atom, hydroxy, amino, and hydroxymethyl;

$R_{a3}'$, $R_{a4}'$, $R_{a6}'$, $R_{a8}'$, $R_{a9}$, $R_{a10}$ and $R_{a11}$ are each independently a hydrogen atom or lower alkyl which may be substituted with one or more of the same or different substituents selected from <substituent group $L_1$>; or $R_1$ is a lower alkyl which may be substituted with one or more of the same or different substituents selected from <substituent group M>, wherein <substituent group M> is a halogen atom, hydroxy, nitro, cyano, amino, carbamoyl, aminosulfonyl, imino, lower alkylamino, di-lower alkylamino, lower alkylsulfonyl, lower alkylsulfonylamino, lower alkoxy, lower alkoxycarbonyl, lower alkoxycarbonylamino, lower alkanoyl, lower alkanoyloxy, lower alkylthio, and carboxyl; or $R_1$ is a heterocyclic group selected from the following, wherein $Y_1$ and $Y_2$ are the same and different, and each a hydrogen atom or lower alkyl which may be substituted:

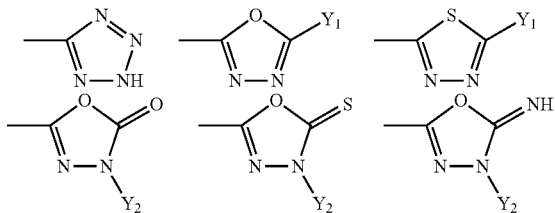

More preferably, $R_1$ is a hydrogen atom, OH, $COOR_{a1}$, $CONR_{a2}R_{a2}'$, or $CONR_{a4}OR_{a4}'$ wherein $R_{a1}$, $R_{a2}$, $R_{a2}'$, $R_{a4}$, and $R_{a4}'$ are the same or different, and each a hydrogen atom or lower alkyl having one to three carbon atoms; or $R_1$ is selected from the following:

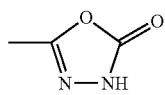

<substituent group $L_1$> is a halogen atom, hydroxy, nitro, cyano, amino, carbamoyl, aminosulfonyl, imino, lower alkylamino, di-lower alkylamino, lower alkylsulfonyl, lower alkylsulfonylamino, lower alkoxy, lower alkoxycarbonyl, lower alkoxycarbonylamino, lower alkanoyl, lower alkanoyloxy, lower alkylthio, and carboxyl; preferably, a hydrogen atom, hydroxy, amino, carbamoyl, lower alkylamino, di-lower alkylamino, and lower alkoxy.

<substituent group $L_2$> is a halogen atom, hydroxy, amino, and hydroxymethyl; preferably hydroxy and hydroxymethyl.

<substituent group M> is a halogen atom, hydroxy, nitro, cyano, amino, carbamoyl, aminosulfonyl, imino, lower alkylamino, di-lower alkylamino, lower alkylsulfonyl, lower alkylsulfonylamino, lower alkoxy, lower alkoxycarbonyl, lower alkoxycarbonylamino, lower alkanoyl, lower alkanoyloxy, lower alkylthio, and carboxyl; preferably, a hydroxy, carbamoyl, aminosulfonyl, lower alkylsulfonylamino, and carboxyl.

$R_2$ is CO, $SO_2$, or $CHR_x$ wherein $R_x$ is $CF_3$, CN, $COR_{x1}$, $COOR_{x2}$, $CONR_{x3}R_{x3}'$, $SO_2R_{x4}$, or $SO_2NR_{x5}R_{x5}'$; and $R_{x1}$, $R_{x2}$ and $R_{x4}$ are each independently a hydrogen atom or lower alkyl which may be substituted; and $R_{x3}$, $R_{x3}'$, $R_{x5}$ and $R_{x5}'$ are each independently a hydrogen atom or lower alkyl which may be substituted, provided, however, that $R_{x3}$ and $R_{x3}'$, and $R_{x5}$ and $R_{x5}'$, each independently, together with the nitrogen atom which they bind to, may form a heterocyclic group which may be substituted;

Preferably, $R_2$ is CO, $SO_2$, or $CHCF_3$.

$R_3$ is a phenyl which may be substituted; preferably, $R_3$ is phenyl of which $2^{nd}$ and $3^{rd}$ positions are substituted with the same or different two substituents selected from F, Cl, $CF_3$, and CN, or a phenyl of which $2^{nd}$ or $3^{rd}$ position is substituted with one substituent selected from F, Cl, $CF_3$, and CN.

$X_1$ is CH, $CX_{1a}$, or N wherein $X_{1a}$ is a lower alkyl which may be substituted.

Preferably, $X_1$ is CH or N; more preferably, CH.

$X_2$ is CH, $CX_{2a}$, or N wherein:
$X_{2a}$ is a lower alkyl; or
$X_{2a}$ is a substituent selected from <substituent group $A_1$>, or lower alkyl which is substituted with one or more of the same or different substituents selected from <substituent group $A_1$>, wherein <substituent group $A_1$> is halogen atom; cyano; hydroxy; lower alkylamino; di-lower alkylamino; lower alkoxy which may be substituted with one or more hydroxy groups; lower alkylthio; and lower alkylsulfonyl; phenyl which may be substituted; or $X_{2a}$ is $COOR_{x10}$, $CONR_{x20}R_{x30}$, $NHCOR_{x10}$, $NHCONR_{x20}R_{x30}$, $NHSO_2NR_{x20}R_{x30}$, $NR_{x40}R_{x50}$, or $CH_2NR_{x40}R_{x50}$, wherein:

$R_{x10}$ is a hydrogen atom or lower alkyl which may be substituted;

$R_{x20}$ and $R_{x30}$, which may be the same or different, are each a hydrogen atom, lower alkyl which may be substituted, or cycloalkyl which may be substituted; or alternatively $R_{x20}$ and $R_{x30}$, together with the nitrogen atom to which they bond, form a 5- or 6-membered aliphatic heterocyclic group which contains at least one atom selected from N, O and S and which may be substituted; and $R_{x40}$ and $R_{x50}$, which may be the same or different, are a hydrogen atom, lower alkyl that may be substituted, or cycloalkyl that may be substituted; or $X_{2a}$ is a 5- to 6-membered aliphatic heterocyclic group which contains at least one atom selected from N, O and S and which may be substituted, wherein two hydrogen atoms that are bonded to the same carbon atom of the aliphatic heterocyclic group may be substituted with oxo and neighboring two carbon atoms constituting the aliphatic heterocyclic ring may form a double-bond; or lower alkyl which is substituted with the aliphatic heterocyclic group; or $X_{2a}$ is a 5- to 6-membered aromatic heterocyclic group which contains at least one atom selected from N, O and S and which may be substituted; or lower alkyl which is substituted with the aromatic heterocyclic group.

Preferably, $X_2$ is CH, $CX_{2a}$, or N wherein $X_{2a}$ is a lower alkyl, a halogen atom; a phenyl which may be substituted; more preferably, when $X_1$ is CH, $X_2$ is CH or $CX_{2a}$ wherein $X_{2a}$ is a phenyl which may be substituted; or when $X_1$ is CH, $X_2$ is N; or when $X_1$ is N, $X_2$ is CN or $CX_{2a}$ wherein $X_{2a}$ is a phenyl which may be substituted.

More preferably, $X_2$ is CH or $CX_{2a}$ wherein $X_{2a}$ is a lower alkyl or phenyl which may be substituted.

$X_3$ is CH, $CX_{3a}$, or N wherein $X_{3a}$ is a lower alkyl which may be substituted.

Preferably, $X_3$ is CH.

However, among $X_1$, $X_2$ and $X_3$, the number of nitrogen is 0 or 1;

With regard to the combinations between $X_1$ and $X_2$, preferably, $X_1$ is CH and $X_2$ is CH or $CX_{2a}$ wherein $X_{2a}$ is a phenyl which may be substituted; or $X_1$ is CH and $X_2$ is N; or $X_1$ is N and $X_2$ is CH or $CX_{2a}$ wherein $X_{2a}$ is a lower alkyl.

With regard to the combinations between $X_1$ and $X_2$, more preferably, both $X_1$ and $X_2$ are CH; or $X_1$ is CH and $X_2$ is $CX_{2a}$ wherein $X_{2a}$ is a phenyl which may be substituted.

<substituent group $A_1$> is halogen atom; cyano; hydroxy; lower alkylamino; di-lower alkylamino; lower alkoxy which may be substituted with one or more hydroxy groups; lower alkylthio; and lower alkylsulfonyl; and phenyl which may be substituted, preferably, halogen atom, hydroxy, di-lower alkylamino lower alkylsulfonyl; and phenyl which may be substituted;

W is the following residue:

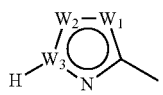

wherein:

$W_1$ is CH, N, NH, O, or S;

$W_2$ is CH, $CW_{2a}$, N, $NW_{2b}$, O or S, wherein $W_{2a}$ and $W_{2b}$ are each independently a hydrogen atom, halogen atom, cyano, lower alkyl having one to two carbon atoms, cycloalkyl having three to five carbon atoms, or lower alkyl having one to two carbon atoms which may be substituted with one or more halogen atoms;

$W_3$ is C or N; and at least one of $W_1$, $W_2$, and $W_3$ is a carbon atom; however two of $W_1$, $W_2$, and $W_3$ are not simultaneously O and S.

W is preferably selected from:

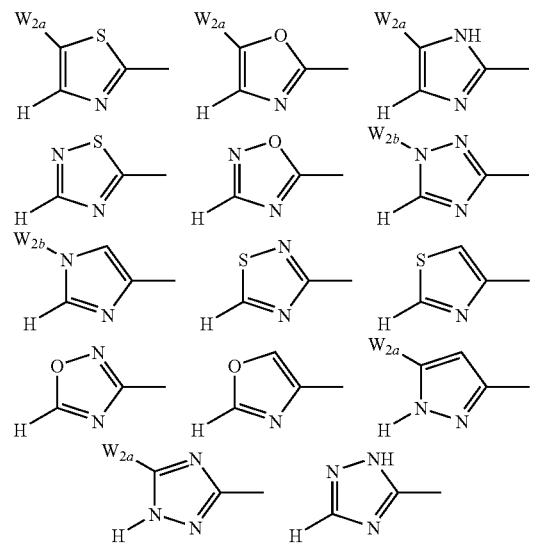

W is more preferably selected from:

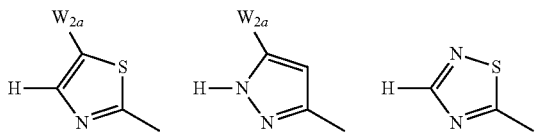

wherein $W_{2a}$ is a hydrogen atom, halogen atom, cyano, or methyl which may be substituted with one to three fluorine atoms.

W is particularly preferably selected from:

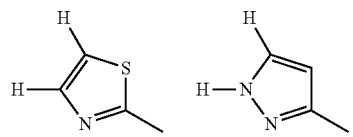

W is still more preferably selected from:

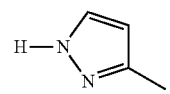

A preferred embodiment of the compound represented by the above General Formula (I) can be also expressed as follows:

(1) The compound of the above Formula (1) or a pharmaceutically acceptable salt or ester thereof, wherein $X_3$ is CH.

(2) The compound as described in above (1), or a pharmaceutically acceptable salt or ester thereof, wherein:

$R_1$ is a hydrogen atom, F, CN, $COOR_{a1}$, $CONR_{a2}R_{a2}'$, $NR_{a3}COR_{a3}'$, $CONR_{a4}OR_{a4}'$, $NR_{a5}CONR_{a5}'R_{a5}''$, $NR_{a6}COOR_{a6}'$, $SO_2NR_{a7}R_{a7}'$, $NR_{a8}SO_2R_{a8}'$, $COR_{a9}$, $SO_2R_{a10}$, $NO_2$, $OR_{a11}$, or $NR_{a12}R_{a12}'$, wherein:

$R_{a1}$, $R_{a3}$, $R_{a4}$, $R_{a5}$, $R_{a6}$, and $R_{a8}$ are each independently a hydrogen atom or lower alkyl;

$R_{a2}$, $R_{a2}'$, $R_{a5}'$, $R_{a5}''$, $R_{a7}$, $R_{a7}'$, $R_{a12}$, and $R_{a12}'$ are each independently a hydrogen atom or lower alkyl which may be substituted with one or more of the same or different substituents selected from <substituent group $L_1$>, wherein <substituent group $L_1$> is a halogen atom, hydroxy, nitro, cyano, amino, carbamoyl, aminosulfonyl, imino, lower alkylamino, di-lower alkylamino, lower alkylsulfonyl, lower alkylsulfonylamino, lower alkoxy, lower alkoxycarbonyl, lower alkoxycarbonylamino, lower alkanoyl, lower alkanoyloxy, lower alkylthio, and carboxyl; provided, however, that $R_{a2}$ and $R_{a2}'$; $R_{a5}'$ and $R_{a5}''$; $R_{a7}$ and $R_{a7}'$; $R_{a12}$ and $R_{a12}'$ each independently, together with the nitrogen atom which they bind to, may form a 5-membered or 6-membered aromatic or aliphatic heterocyclic group which may be substituted with one or more of the same or different substituents selected from <substituent group $L_2$>, wherein <substituent group $L_2$> is a halogen atom, hydroxy, amino, and hydroxymethyl;

$R_{a3}'$, $R_{a4}'$, $R_{a6}'$, $R_{a8}'$, $R_{a9}$, $R_{a10}$ and $R_{a11}$ are each independently a hydrogen atom or lower alkyl which may be substituted with one or more of the same or different substituents selected from <substituent group $L_1$>; or $R_1$ is a lower alkyl which may be substituted with one or more of the same or different substituents selected from <substituent group M>, wherein <substituent group M> is a halogen atom, hydroxy, nitro, cyano, amino, carbamoyl, aminosulfonyl, imino, lower alkylamino, di-lower alkylamino, lower alkylsulfonyl, lower alkylsulfonylamino, lower alkoxy, lower alkoxycarbonyl, lower alkoxycarbonylamino, lower alkanoyl, lower alkanoyloxy, lower alkylthio, and carboxyl; or $R_1$ is a heterocyclic group selected from the following, wherein $Y_1$ and $Y_2$ are the same and different, and each a hydrogen atom or lower alkyl which may be substituted:

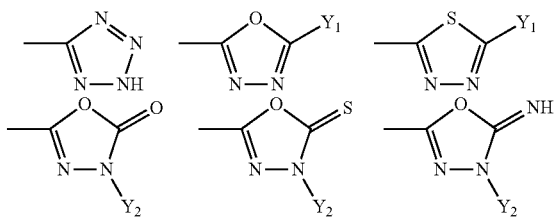

(3) The compound as described in above (2), or a pharmaceutically acceptable salt or ester thereof, wherein W is selected from:

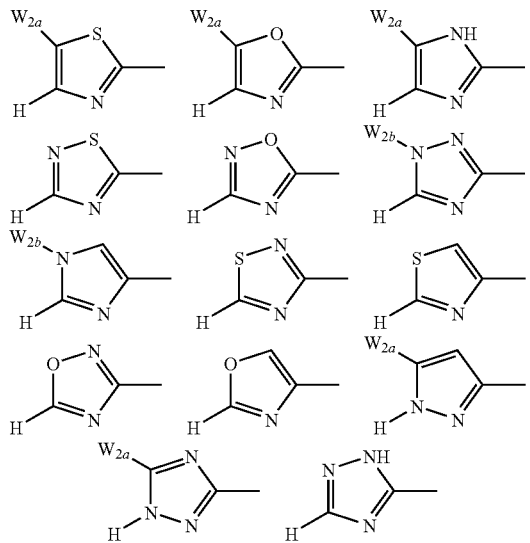

(4) The compound as described in above (3), or a pharmaceutically acceptable salt or ester thereof, wherein $R_3$ is a phenyl of which $2^{nd}$ and $3^{rd}$ positions are substituted with the same or different two substituents selected from F, Cl, $CF_3$, and CN, or a phenyl of which $2^{nd}$ or $3^{rd}$ position is substituted with one substituent selected from F, Cl, $CF_3$, and CN.

(5) The compound as described in above (4), or a pharmaceutically acceptable salt or ester thereof, wherein <substituent group $L_1$> is a halogen atom, hydroxy, amino, carbamoyl, lower alkylamino, di-lower alkylamino, and lower alkoxy; and <substituent group M> is a hydroxy, carbamoyl, aminosulfonyl, lower alkylsulfonylamino, and carboxyl.

(6) The compound as described in above (5), or a pharmaceutically acceptable salt or ester thereof, wherein $X_1$ is CH and $X_2$ is CH or $CX_{2a}$ wherein $X_{2a}$ is a phenyl which may be substituted; or $X_1$ is CH and $X_2$ is N; or $X_1$ is N and $X_2$ is CH or $CX_{2a}$ wherein $X_{2a}$ is a lower alkyl or a halogen atom.

(7) The compound as described in above (6), or a pharmaceutically acceptable salt or ester thereof, wherein $R_1$ is hydrogen atom, OH, $COOR_{a1}$, $CONR_{a2}R_{a2}'$, or $CONR_{a4}OR_{a4}'$ wherein $R_{a1}$, $R_{a2}$, $R_{a2}'$, $R_{a4}$, and $R_{a4}'$ are the same or different, and each a hydrogen atom or lower alkyl having one to three carbon atoms; or $R_1$ is selected from the following:

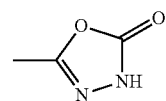

and $R_2$ is CO, $SO_2$, or $CHCF_3$.

(8) The compound as described in above (7), or a pharmaceutically acceptable salt or ester thereof, wherein:
W is selected from:

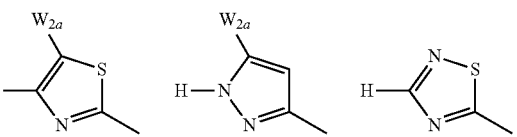

wherein $W_{2a}$ is a hydrogen atom, halogen atom, cyano, or methyl which may be substituted with one to three fluorine atoms.

(9) The compound as described in above (8), or a pharmaceutically acceptable salt or ester thereof, wherein both of $X_1$ and $X_2$ are CH; and W is any one of the following:

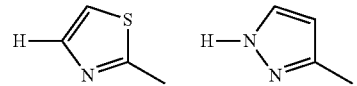

(10) A compound which is:
(a) 1-(3-chloro-2-fluorobenzoyl)-4-((6-(1H-pyrazol-3-ylamino)pyridin-2-yl)methyl)piperidin-4-ol (example 2);
(b) 5-(1-(2-fluoro-3-(trifluoromethyl)benzoyl)-4-((6-(1H-pyrazol-3-ylamino)pyridin-2-yl)methyl)piperidin-4-yl)-1,3,4-oxadiazol-2(3H)-one (example 9);
(c) 5-(1-(3-chloro-2-fluorobenzoyl)-4-((6-(1H-pyrazol-3-ylamino)pyridin-2-yl)methyl)piperidin-4-yl)-1,3,4-oxadiazol-2(3H)-one (example 10);
(d) 5-(4-((6-(1H-pyrazol-3-ylamino)pyridin-2-yl)methyl)-1-((2-(trifluoromethyl)phenyl)sulfonyl)piperidin-4-yl)-1,3,4-oxadiazol-2(3H)-one (example 14);
(e) 5-(1-(3-chloro-2-fluorobenzoyl)-4-((4-phenyl-6-(1H-pyrazol-3-ylamino)pyridin-2-yl)methyl)piperidin-4-yl)-1,3,4-oxadiazol-2(3H)-one (example 17); or
(f) 5-(4-((6-(1H-pyrazol-3-ylamino)pyridin-2-yl)methyl)-1-(2,2,2-trifluoro-1-(3-(trifluoromethyl)phenyl)ethyl)piperidin-4-yl)-1,3,4-oxadiazol-2(3H)-one (example 19);
or a pharmaceutically acceptable salt or ester thereof.

Further, in the combined preparation comprising two separate preparations according to the invention, preferably either or both of the two separate preparations are an oral preparation.

The combined preparation comprising two separate preparations according to the invention is preferably such that one of the preparations is a preparation containing, together with a pharmaceutically acceptable carrier or diluent, the following:

(a) 1-(3-chloro-2-fluorobenzoyl)-4-((6-(1H-pyrazol-3-ylamino)pyridin-2-yl)methyl)piperidin-4-ol;
(b) 5-(1-(2-fluoro-3-(trifluoromethyl)benzoyl)-4-((6-(1H-pyrazol-3-ylamino)pyridin-2-yl)methyl)piperidin-4-yl)-1,3,4-oxadiazol-2(3H)-one;
(c) 5-(1-(3-chloro-2-fluorobenzoyl)-4-((6-(1H-pyrazol-3-ylamino)pyridin-2-yl)methyl)piperidin-4-yl)-1,3,4-oxadiazol-2(3H)-one;
(d) 5-(4-((6-(1H-pyrazol-3-ylamino)pyridin-2-yl)methyl)-1-((2-(trifluoromethyl)phenyl)sulfonyl)piperidin-4-yl)-1,3,4-oxadiazol-2(3H)-one;
(e) 5-(1-(3-chloro-2-fluorobenzoyl)-4-((4-phenyl-6-(1H-pyrazol-3-ylamino)pyridin-2-yl)methyl)piperidin-4-yl)-1,3,4-oxadiazol-2(3H)-one; or
(f) 5-(4-((6-(1H-pyrazol-3-ylamino)pyridin-2-yl)methyl)-1-(2,2,2-trifluoro-1-(3-(trifluoromethyl)phenyl)ethyl)piperidin-4-yl)-1,3,4-oxadiazol-2(3H)-one;

or a pharmaceutically acceptable salt or ester thereof; and
the other preparation is a preparation containing paclitaxel or docetaxel, or a pharmaceutically acceptable salt or ester thereof, together with a pharmaceutically acceptable carrier or diluent.

Moreover, the combined preparation comprising, together with a pharmaceutically acceptable carrier or diluent, two separate preparations according to the invention may be further combined with at least one preparation containing an antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents (here, definition of each antitumor agent is the same as that defined above), or a pharmaceutically acceptable salt or ester thereof.

Also, the pharmaceutical composition according to the invention preferably contains, together with a pharmaceutically acceptable carrier or diluent, the following:

(a) 1-(3-chloro-2-fluorobenzoyl)-4-((6-(1H-pyrazol-3-ylamino)pyridin-2-yl)methyl)piperidin-4-ol;
(b) 5-(1-(2-fluoro-3-(trifluoromethyl)benzoyl)-4-((6-(1H-pyrazol-3-ylamino)pyridin-2-yl)methyl)piperidin-4-yl)-1,3,4-oxadiazol-2(3H)-one;
(c) 5-(1-(3-chloro-2-fluorobenzoyl)-4-((6-(1H-pyrazol-3-ylamino)pyridin-2-yl)methyl)piperidin-4-yl)-1,3,4-oxadiazol-2(3H)-one;
(d) 5-(4-((6-(1H-pyrazol-3-ylamino)pyridin-2-yl)methyl)-1-((2-(trifluoromethyl)phenyl)sulfonyl)piperidin-4-yl)-1,3,4-oxadiazol-2(3H)-one;
(e) 5-(1-(3-chloro-2-fluorobenzoyl)-4-((4-phenyl-6-(1H-pyrazol-3-ylamino)pyridin-2-yl)methyl)piperidin-4-yl)-1,3,4-oxadiazol-2(3H)-one; or
(f) 5-(4-((6-(1H-pyrazol-3-ylamino)pyridin-2-yl)methyl)-1-(2,2,2-trifluoro-1-(3-(trifluoromethyl)phenyl)ethyl)piperidin-4-yl)-1,3,4-oxadiazol-2(3H)-one;

or a pharmaceutically acceptable salt or ester thereof; and paclitaxel or docetaxel, or a pharmaceutically acceptable salt or ester thereof, together with a pharmaceutically acceptable carrier or diluent.

Description of the process for preparation of compound of General Formula (I)

Among the compounds represented by the General Formula (I):

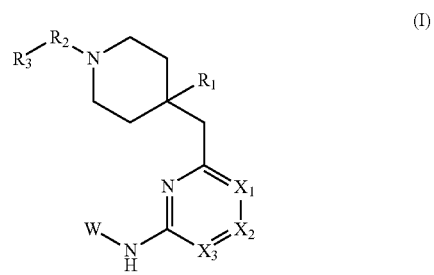

(wherein $R_1$, $R_2$, $R_3$, $X_1$, $X_2$, $X_3$, and W have the same meaning as the symbols for the above Formula (I)) according to the invention, the compound of Formula (I-1):

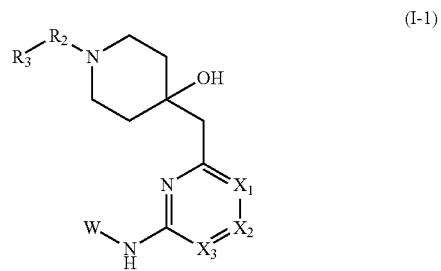

(wherein $R_1$ is OH; $R_2$, $R_3$, $X_1$, $X_2$, $X_3$, and W have the same meaning as the symbols for the above Formula (I)) can be prepared by, for example, the following method. Hereinafter, the phrase "symbols for the above Formula (I)" as used herein means "the respective symbols as described for General Formula (I) initially described in the present specification."

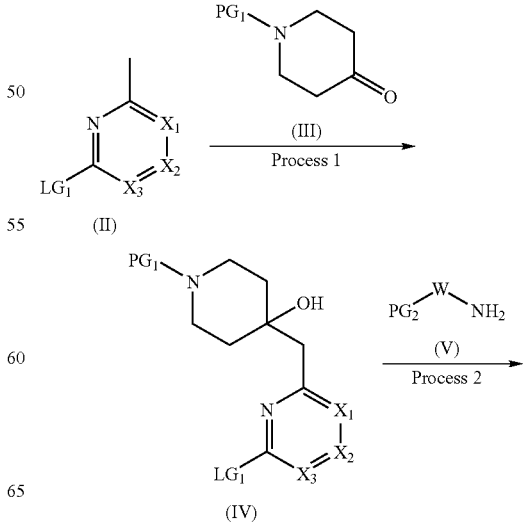

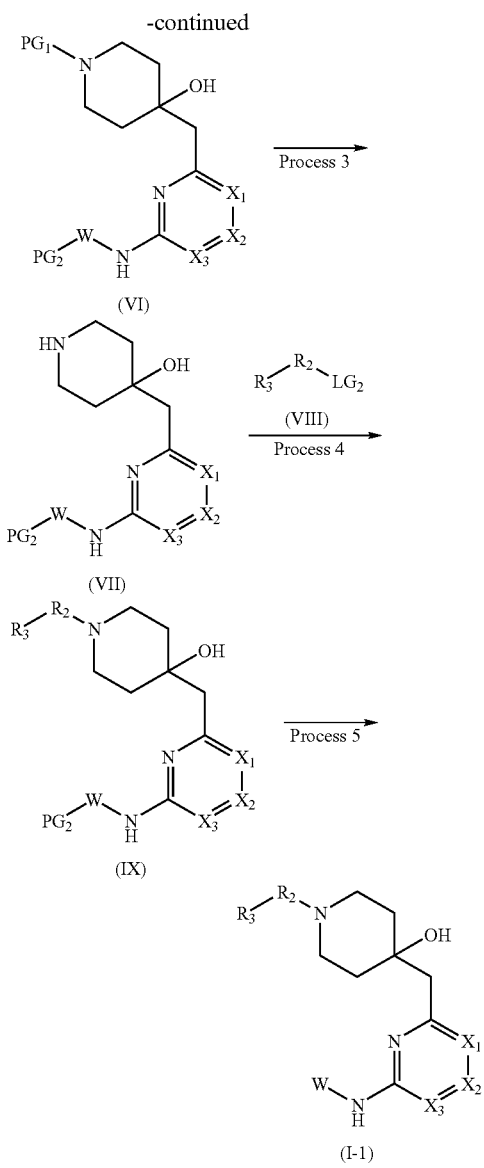

(Process 1)

The present process is a method of subjecting the Compound (II) (wherein $LG_1$ is a leaving group such as halogen atom, and $X_1$, $X_2$, and $X_3$ have the same meaning as the symbols for the above Formula (I)) and Compound (III) (wherein $PG_1$ is a protecting group such as tert-butoxycarbonyl or benzyl), to an alkylation reaction, thereby to produce Compound (IV) (wherein $LG_1$ and $PG_1$ have the same meaning as defined above, and $X_1$, $X_2$, and $X_3$ have the same meaning as the symbols for the above Formula (I)).

The Compound (II) used in this process may be exemplified by 2-chloro-6-methylpyridine, 2-bromo-6-methylpyridine, and the like. The Compound (II) is commercially available or can be prepared by a known method.

The Compound (III) used in this process may be exemplified by tert-butyl 4-oxo-1-piperidinecarboxylate, 1-benzyl-4-piperidone, and the like. The Compound (III) is commercially available or can be prepared by a known method.

The alkylation reaction used in this process employs methods well known to those skilled in the art. The alkylation reaction, for example, can be carried out in accordance with a method described in Tetrahedron (1995), Vol. 51, 1337. In the alkylation reaction used in this process, specifically, for example, the Compound (IV) can be synthesized by reacting the Compound (II) in a solvent such as tetrahydrofuran with a base such as butyllithium or lithium diisopropylamide to produce an anion of the Compound (II), followed by adding thereto the Compound (III) and if necessary an additive such as cerium(III) chloride, and the like. In this reaction, Compound (II) is used in an amount of from 1 to 10 mol, preferably from 1 to 5 mol; and the base is used in an amount of from 1 to 10 mol, preferably from 1 to 5 mol; and the additive is used in an amount of from 1 to 100 mol, preferably from 1 to 10 mol, relative to 1 mol of Compound (II). The reaction temperature can be appropriately selected by a person having ordinary skill in the art in accordance with the starting compound or reaction solvent used, but it is typically from $-78°$ C. to room temperature. Also, the reaction is typically completed within 1 hour to 48 hours, but the reaction time can be appropriately extended or reduced.

The resulting Compound (IV) is subjected to isolation and purification by known separation and purification means such as, for example, concentration, concentration under reduced pressure, crystallization, solvent extraction, reprecipitation or chromatography, or may be subjected to the next process without isolation and purification.

(Process 2)

The present process is a method of subjecting the Compound (IV) (wherein $LG_1$ and $PG_1$ have the same meaning as defined above, and $X_1$, $X_2$, and $X_3$ have the same meaning as the symbols for the above Formula (I)), obtained in the above-described Process 1, and Compound (V) (wherein $PG_2$ may be absent, or if present, it is a protective group such as 4-methoxybenzyl, 2,4-dimethoxybenzyl, benzyl, methoxymethyl, (2-(trimethylsilyl)ethoxy)methyl or tert-butyl, preferably (2-(trimethylsilyl)ethoxy)methyl, methoxymethyl or tert-butyl, and W has the same meaning as the symbol for the above Formula (I)), to an amination reaction, thereby to produce Compound (VI) (wherein $PG_1$ and $PG_2$ have the same meaning as defined above, and $X_1$, $X_2$, $X_3$, and W have the same meaning as the symbols for the above Formula (I)).

The Compound (V) used in this process may be exemplified by 2-aminothiazole, 1-((2-(trimethylsilyl)ethoxy)methyl)-1H-pyrazol-3-amine, 1-tert-butyl-3-methyl-1H-pyrazol-5-amine, 1-tert-butyl-1H-pyrazol-5-amine, and the like. The Compound (V) is commercially available or can be prepared by a known method (e.g., Phosphorus, Sulfur and Silicon and the Related Elements, Vol. 177, No. 11, pages 2651-2659 (2002), and Journal of Chemical Research, Synopses, Vol. 6, page 198 (1979)).

The amination reaction used in this process employs a method well known to those skilled in the art. The amination reaction, for example, can be carried out in accordance with a method described in Organic Letter (2002), Vol. 4, 3484. In the amination reaction used in the process, specifically, for example, synthesis can be conducted by reacting the Compound (IV) and Compound (V) in a solvent such as 1,4-dioxane, 1,2-dimethoxyethane, tetrahydrofuran, methylene chloride, chloroform or toluene, using a palladium catalyst such as trisdibenzylideneacetone dipalladium (0) or palladium acetate; a ligand such as 2,2'-bisdiphenylphosphino-1, 1'-binaphthyl or 4,5-bis(diphenylphosphino)-9,9-dimethylxanthene; and a base such as cesium carbonate or sodium t-butoxide. In the reaction, 0.5 to 3 mol, preferably 1 mol, of Compound (V) is used; 0.001 to 1 mol, preferably 0.05 to 0.5 mol, of the palladium catalyst is used; 0.002 to 2 mol, preferably 0.1 to 1.0 mol, of the ligand is used; and 1 to 10 mol, preferably 1 to 3 mol, of the base is used, relative to 1 mol of Compound (IV). The reaction temperature is appropriately selected by a person skilled in the art in accordance with the starting compound or reaction solvent used, but it is typically from 50° C. to the boiling point of the solvent used in the reaction. Also, the reaction is typically completed between 1 hour to 24 hours, but the reaction time can be appropriately extended or reduced.

The resulting Compound (VI) is subjected to isolation and purification by known separation and purification means such as, for example, concentration, concentration under reduced pressure, crystallization, solvent extraction, reprecipitation or chromatography, or maybe subjected to the next process without isolation and purification.

(Process 3)

The present process is a method of deprotecting a protective group $PG_1$ of the Compound (VI) (wherein $PG_1$ and $PG_2$ have the same meaning as defined above, and $X_1, X_2, X_3$, and W have the same meaning as the symbols for the above Formula (I)), obtained in the above-described Process 2, thereby to produce Compound (VII) (wherein $PG_2$ has the same meaning as defined above, and $X_1, X_2, X_3$, and W have the same meaning as the symbols for the above Formula (I)).

For the deprotection reaction of $PG_1$, the method may vary depending on the type of the protective group or stability of the compound, but methods described in the literature [See T. W. Greene, Protective Groups in Organic Synthesis, John Wiley & Sons (1981)] or methods equivalent thereto can be carried out. For example, the Compound (VI) in which $PG_1$ is tert-butoxycarbonyl can be deprotected in a mixed solvent of trifluoroacetic acid and chloroform. The reaction temperature can be appropriately selected by a person having ordinary skill in the art in accordance with the starting compound or reaction solvent used, but it is typically from 0° C. to the boiling point of the solvent. Also, the reaction is typically completed between 1 hour to 24 hours, but the reaction time can be appropriately extended or reduced.

The resulting Compound (VII) is subjected to isolation and purification by known separation and purification means such as, for example, concentration, concentration under reduced pressure, crystallization, solvent extraction, reprecipitation or chromatography, or may be subjected to the next process without isolation and purification.

(Process 4)

The present process is a method of subjecting Compound (VII) (wherein $PG_2$ has the same meaning as defined above, and $X_1, X_2, X_3$, and W have the same meaning as the symbols for the above Formula (I)), obtained in the above-described Process 3, and Compound (VIII) (wherein $LG_2$ represents a leaving group such as chloride or hydroxy, and $R_2$ and $R_3$ have the same meaning as the symbols for the above Formula (I)), to a condensation reaction, thereby to produce Compound (IX) (wherein $PG_2$ has the same meaning as defined above; and $R_2, R_3, X_1, X_2, X_3$, and W have the same meaning as the symbols for the above Formula (I)).

The Compound (VIII) used in this process may be exemplified by 3-chloro-2-fluorobenzoic acid. The Compound (VIII) is commercially available, or can be produced by a known method.

In the condensation reaction used in this process employs the carboxylic acid of the Compound (VIII) or a reactive derivative thereof, and the Compound (VII) are used together with a condensation agent. The Compound (VIII) as a reactive derivative can be exemplified by a mixed acid anhydride, activated ester, activated amide, and the like; they can be obtained by a method described, for example, in Science of Synthesis (2005), Vol. 21, 43. Specifically, the condensation can be conducted, for example, using the Compound (VII) and the Compound (VIII) in a solvent such as tetrahydrofuran, dimethylsulfoxide, N,N-dimethylformamide, 1,4-dioxane, dichloromethane, chloroform, and the like, together with a condensation agent such as 1-(3-dimethylaminopropyl)-3-ethylcarbodiimide, and 1-hydroxybenzotriazole. In this case, Compound (VIII) is used in an amount of from 1 to 3 mol, preferably 1 mol; the condensation agent is used in an amount of from 1 to 10 mol, preferable from 1 to 3 mol, relative to 1 mol of compound (VII). The reaction temperature is appropriately selected by a person skilled in the art in accordance with the starting compound or reaction solvent used, but it is typically from room temperature to the boiling point of the solvent used in the reaction. Also, the reaction is typically completed between 1 hour to 24 hours, but the reaction time can be appropriately extended or reduced.

The resulting Compound (IX) is subjected to isolation and purification by known separation and purification means such as, for example, concentration, concentration under reduced pressure, crystallization, solvent extraction, reprecipitation or chromatography, or may be subjected to the next process without isolation and purification.

If there is no need for deprotection regarding the Compound (IX), then the Compound (IX) per se becomes the compound according to the present invention without conducting Process 5 and the processes thereafter.

(Process 5)

The present process is a method of deprotecting a protective group $PG_2$ of the Compound (IX) (wherein $PG_2$ has the same meaning as defined above, and $R_2, R_3, X_1, X_2, X_3$, and W have the same meaning as the symbols for the above Formula (I)), obtained in the above-described Process 4, thereby to produce Compound (I-1) (wherein $R_2, R_3, X_1, X_2, X_3$, and W have the same meaning as the symbols for the above Formula (I)).

For the deprotection reaction of $PG_2$, the method may vary depending on the type of the protective group or stability of the compound, but methods described in the literature [See T. W. Greene, Protective Groups in Organic Synthesis, John Wiley & Sons (1981)] or methods equivalent thereto can be carried out. For example, the Compound (IX) (wherein $PG_2$ is (2-(trimethylsilyl)ethoxy)methyl) can be deprotected in a mixed solvent of trifluoroacetic acid and water. The reaction temperature can be appropriately selected by a person having ordinary skill in the art in accordance with the starting compound or reaction solvent used, but it is typically from room temperature to the boiling point of the solvent. Also, the reaction is typically completed between 1 hour to 24 hours, but the reaction time can be appropriately extended or reduced.

The resulting Compound (I-1) is subjected to isolation and purification by known separation and purification means such as, for example, concentration, concentration under reduced pressure, crystallization, solvent extraction, reprecipitation or chromatography.

Among the compounds represented by the General Formula (I) (wherein $R_1, R_2, R_3, X_1, X_2, X_3$, and W have the same meaning as defined in the above) according to the invention, the compound of Formula (I-2):

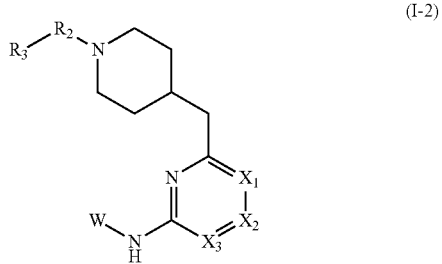

(I-2)

(wherein $R_1$ is a hydrogen atom; $R_2$, $R_3$, $X_1$, $X_2$, $X_3$, and W have the same meaning as the symbols for the above Formula (I)) can be prepared by, for example, the following method.

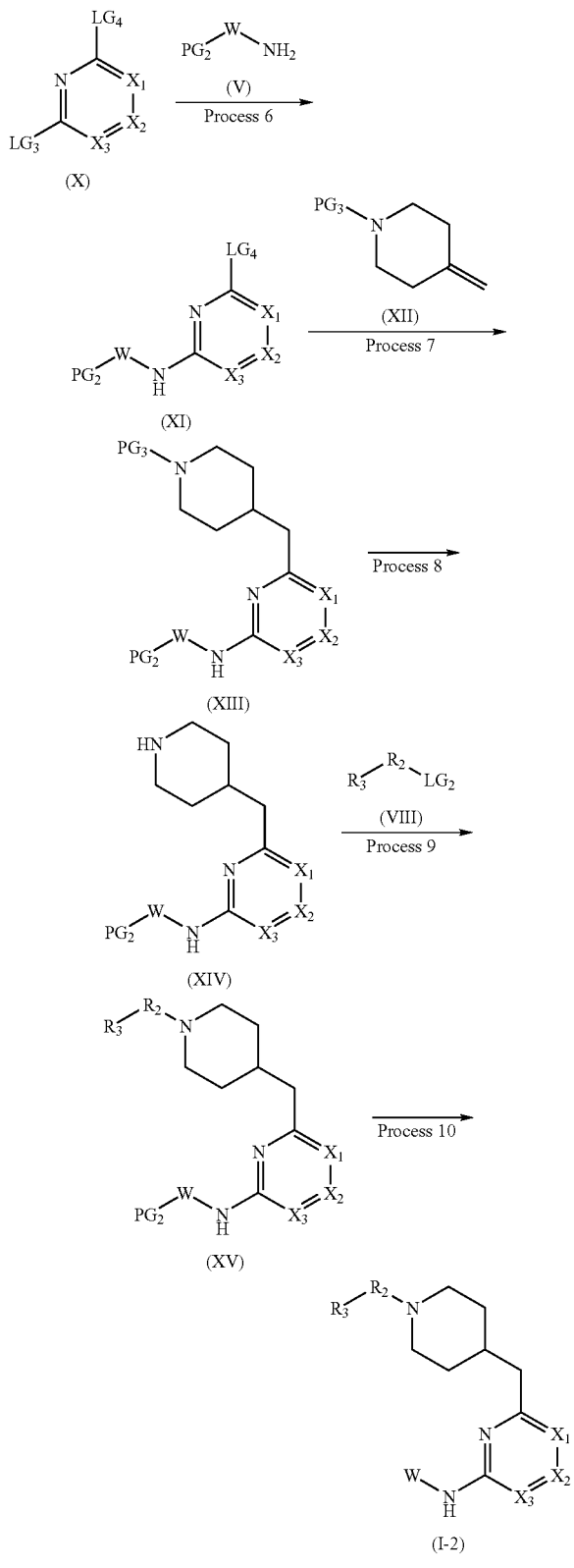

(Process 6)

The present process is a method of subjecting Compound (X) (wherein $LG_3$ and $LG_4$ are a leaving group such as halogen atom, and $X_1$, $X_2$, and $X_3$ have the same meaning as the symbols for the above Formula (I)) and Compound (V) (wherein $PG_2$ may be absent, or if present, it is a protective group such as 4-methoxybenzyl, 2,4-dimethoxybenzyl, benzyl, methoxymethyl, (2-(trimethylsilyl)ethoxy)methyl or tert-butyl, preferably (2-(trimethylsilyl)ethoxy)methyl, methoxymethyl or tert-butyl, and W has the same meaning as the symbol for the above Formula (I)), to an amination reaction, thereby to produce Compound (XI) (wherein $PG_2$ and $LG_4$ have the same meaning as defined above, and $X_1$, $X_2$, $X_3$, and W have the same meaning as the symbols for the above Formula (I)).

The Compound (X) used in this process may be exemplified by 2,4-dichloro-6-methylpyrimidine. The Compound (X) is commercially available or can be prepared by a known method.

The Compound (V) used in this process may be exemplified by 2-aminothiazole, 1-((2-(trimethylsilyl)ethoxy)methyl)-1H-pyrazol-3-amine, 1-tert-butyl-3-methyl-1H-pyrazol-5-amine, 1-tert-butyl-1H-pyrazol-5-amine, and the like. The Compound (V) is commercially available or can be prepared by a known method (e.g., Phosphorus, Sulfur and Silicon and the Related Elements, Vol. 177, No. 11, pages 2651-2659 (2002), and Journal of Chemical Research, Synopses, Vol. 6, page 198 (1979)).

The present process can also be carried out by the same method as used in Process 2, or a method equivalent thereto, or a combination of the same with a commonly used method.

The resulting Compound (XI) is subjected to isolation and purification by known separation and purification means such as, for example, concentration, concentration under reduced pressure, crystallization, solvent extraction, reprecipitation or chromatography, or may be subjected to the next process without isolation and purification.

(Process 7)

The present process is a method of reacting the Compound (XI) (wherein $PG_2$ and $LG_4$ have the same meaning as defined above, and $X_1$, $X_2$, $X_3$, and W have the same meaning as the symbols for the above Formula (I)), obtained in the above-described Process 6, with Compound (XII) (wherein $PG_3$ is a leaving group such as tert-butoxycarbonyl), thereby to produce Compound (XIII) (wherein $PG_2$ and $PG_3$ have the same meaning as defined above, and $X_1$, $X_2$, $X_3$, and W have the same meaning as the symbols for the above Formula (I)).

The Compound (XII) used in this process may be exemplified by tert-butyl 4-methylenepiperidine-1-carboxylate. The Compound (XII) is commercially available, or can be produced by a known method.

The coupling reaction used in this process employs a method well known to those skilled in the art. The coupling reaction, for example, can be carried out in accordance with a method described in Journal of Organic Chemistry (2001), Vol. 66, 2487. In the coupling reaction used in this process, specifically, for example, the Compound (XIII) can be synthesized by reacting the Compound (XII) in a solvent such as tetrahydrofuran, 1,4-dioxane or N,N-dimethylformamide with a boron reagent such as 9-borabicyclo[3.3.1] nonane to produce a boron reagent of the Compound (XII), followed by adding thereto the Compound (XI), using a palladium catalyst such as (1,1'-bis(diphenylphosphino)ferrocene)dichloropalladium(II)-dichloromethane complex; a base such as potassium carbonate; and if necessary an additive such as triphenylarsine, and the like. In this reaction, the Compound (XII) is used in an amount of from 1 to 10 mol, preferably from 1 to 5 mol; the boron reagent is used in an amount of from 0.5 to 5 mol, preferably from 0.5 to 2.5 mol; the palladium catalyst is used in an amount of from 0.01 to 1 mol, preferably from 0.05 to 0.5 mol; the base is used in an amount of from 1 to 10 mol, preferably from 1 to 5 mol; and the additive is used in an amount of from 0.01 to 1 mol, preferably from 0.05 to 0.5 mol, relative to 1 mol of Compound (XI). The reaction temperature can be appropriately selected by a person having ordinary skill in the art in accordance with the starting compound or reaction solvent used, but it is typically from room temperature to the boiling point of the solvent. Also, the reaction is typically completed within 1 hour to 48 hours, but the reaction time can be appropriately extended or reduced.

The resulting Compound (XIII) is subjected to isolation and purification by known separation and purification means such as, for example, concentration, concentration under reduced pressure, crystallization, solvent extraction, reprecipitation or chromatography, or may be subjected to the next process without isolation and purification.

(Process 8)

The present process is a method of deprotecting a protective group $PG_3$ of the Compound (XIII) (wherein $PG_2$ and $PG_3$ have the same meaning as defined above, and $X_1$, $X_2$, $X_3$, and W have the same meaning as the symbols for the above Formula (I)), obtained in the above-described Process 7, thereby to produce Compound (XIV) (wherein $PG_2$ has the same meaning as defined above, and $X_1$, $X_2$, $X_3$, and W have the same meaning as the symbols for the above Formula (I)).

For the deprotection reaction of $PG_3$, the method may vary depending on the type of the protective group or stability of the compound, but methods described in the literature [See T. W. Greene, Protective Groups in Organic Synthesis, John Wiley & Sons (1981)] or methods equivalent thereto can be carried out. For example, the Compound (XIII) in which $PG_3$ is tert-butoxycarbonyl can be deprotected in a mixed solvent of trifluoroacetic acid and chloroform.

The present process can also be carried out by the same method as used in Process 3, or a method equivalent thereto, or a combination of the same with a commonly used method.

The resulting Compound (XIV) is subjected to isolation and purification by known separation and purification means such as, for example, concentration, concentration under reduced pressure, crystallization, solvent extraction, reprecipitation or chromatography, or may be subjected to the next process without isolation and purification.

(Process 9)

The present process is a method of subjecting Compound (XIV) (wherein $PG_2$ has the same meaning as defined above, and $X_1$, $X_2$, $X_3$, and W have the same meaning as the symbols for the above Formula (I)), obtained in the above-described Process 8, and Compound (VIII) (wherein $LG_2$ represents a leaving group such as chloride or hydroxy, and $R_2$ and $R_3$ have the same meaning as the symbols for the above Formula (I)), to a condensation reaction, thereby to produce Compound (XV) (wherein $PG_2$ has the same meaning as defined above; $R_2$, $R_3$, $X_1$, $X_2$, $X_3$, and W have the same meaning as the symbols for the above Formula (I)).

The Compound (VIII) used in this process may be exemplified by 3-chloro-2-fluorobenzoic acid. The Compound (VIII) is commercially available, or can be produced by a known method.

The present process can also be carried out by the same method as used in Process 4, or a method equivalent thereto, or a combination of the same with a commonly used method.

The resulting Compound (XV) is subjected to isolation and purification by known separation and purification means such as, for example, concentration, concentration under reduced pressure, crystallization, solvent extraction, reprecipitation or chromatography, or may be subjected to the next process without isolation and purification.

If there is no need for deprotection regarding the Compound (XV), then the Compound (XV) per se becomes the compound according to the present invention without conducting Process 10 and the processes thereafter.

(Process 10)

The present process is a method of deprotecting a protective group $PG_2$ of the Compound (XV) (wherein $PG_2$ has the same meaning as defined above, $R_2$, $R_3$, $X_1$, $X_2$, $X_3$, and W have the same meaning as the symbols for the above Formula (I)), obtained in the above-described Process 9, thereby to produce Compound (I-2) (wherein $R_2$, $R_3$, $X_1$, $X_2$, $X_3$, and W have the same meaning as the symbols for the above Formula (I)).

For the deprotection reaction of $PG_2$, the method may vary depending on the type of the protective group or stability of the compound, but methods described in the literature [See T. W. Greene, Protective Groups in Organic Synthesis, John Wiley & Sons (1981)] or methods equivalent thereto can be carried out. For example, the Compound (XV) (wherein $PG_2$ is (2-(trimethylsilyl)ethoxy)methyl) can be deprotected in a mixed solvent of trifluoroacetic acid and water.

The present process can also be carried out by the same method as used in Process 5, or a method equivalent thereto, or a combination of the same with a commonly used method.

The resulting Compound (I-2) is subjected to isolation and purification by known separation and purification means such as, for example, concentration, concentration under reduced pressure, crystallization, solvent extraction, reprecipitation or chromatography.

Among the compounds represented by the General Formula (I) (wherein $R_1$, $R_2$, $R_3$, $X_1$, $X_2$, $X_3$, and W have the same meaning as defined in the above) according to the invention, the compound of Formula (I-3):

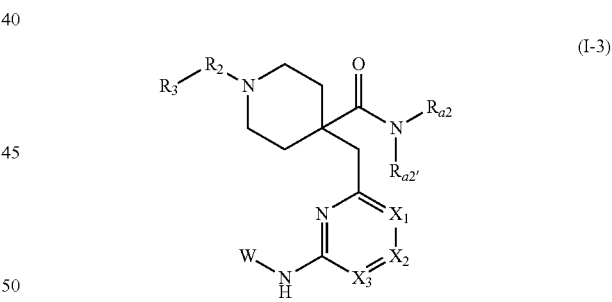

(wherein $R_1$ is $CONR_{a2}R_{a2}'$; $R_2$, $R_3$, $R_{a2}$, $R_{a2}'$, $X_1$, $X_2$, $X_3$, and W have the same meaning as the symbols for the above Formula (I)) can be prepared by, for example, the following method.

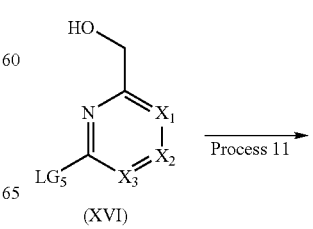

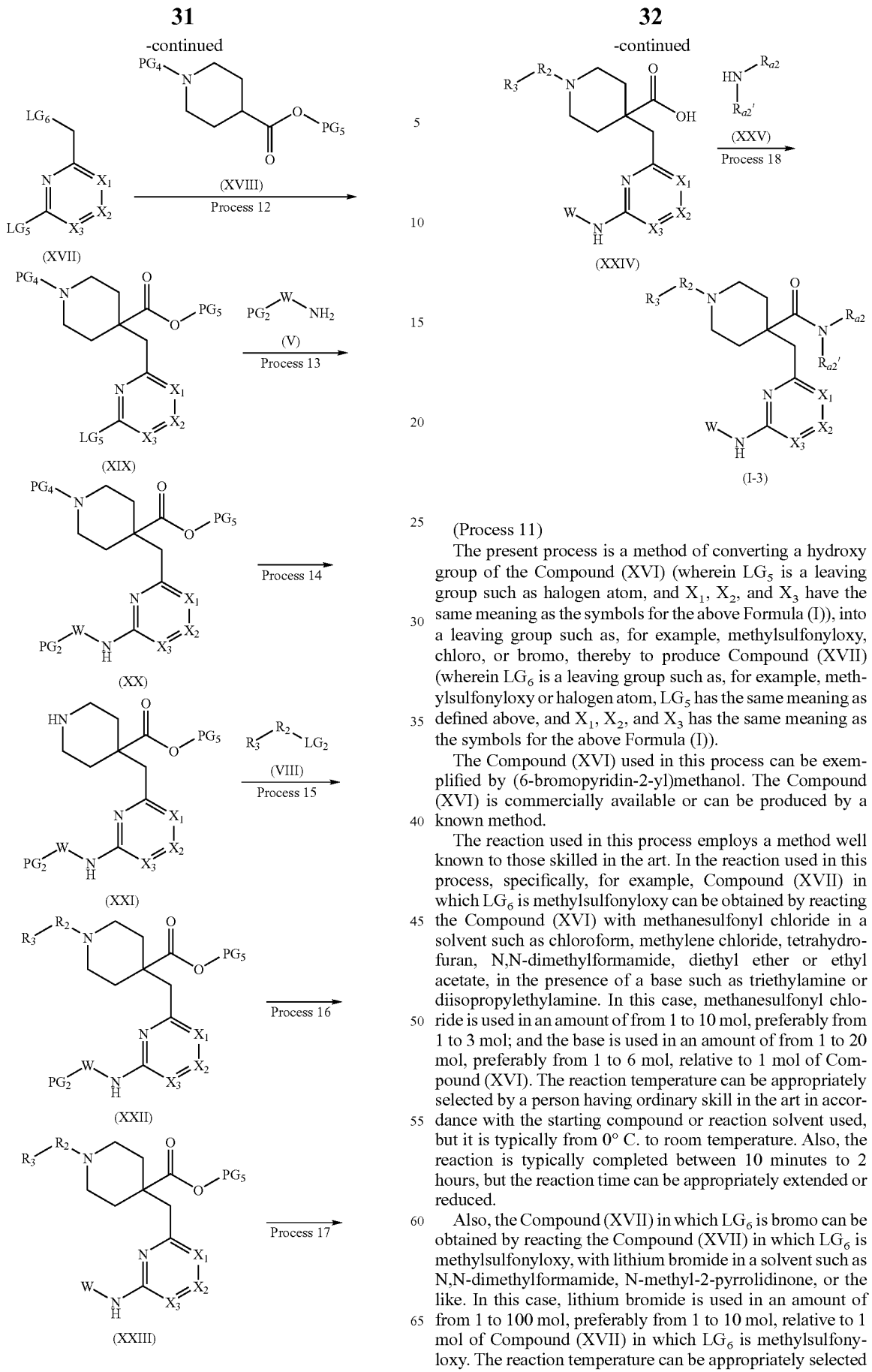

(Process 11)

The present process is a method of converting a hydroxy group of the Compound (XVI) (wherein $LG_5$ is a leaving group such as halogen atom, and $X_1$, $X_2$, and $X_3$ have the same meaning as the symbols for the above Formula (I)), into a leaving group such as, for example, methylsulfonyloxy, chloro, or bromo, thereby to produce Compound (XVII) (wherein $LG_6$ is a leaving group such as, for example, methylsulfonyloxy or halogen atom, $LG_5$ has the same meaning as defined above, and $X_1$, $X_2$, and $X_3$ has the same meaning as the symbols for the above Formula (I)).

The Compound (XVI) used in this process can be exemplified by (6-bromopyridin-2-yl)methanol. The Compound (XVI) is commercially available or can be produced by a known method.

The reaction used in this process employs a method well known to those skilled in the art. In the reaction used in this process, specifically, for example, Compound (XVII) in which $LG_6$ is methylsulfonyloxy can be obtained by reacting the Compound (XVI) with methanesulfonyl chloride in a solvent such as chloroform, methylene chloride, tetrahydrofuran, N,N-dimethylformamide, diethyl ether or ethyl acetate, in the presence of a base such as triethylamine or diisopropylethylamine. In this case, methanesulfonyl chloride is used in an amount of from 1 to 10 mol, preferably from 1 to 3 mol; and the base is used in an amount of from 1 to 20 mol, preferably from 1 to 6 mol, relative to 1 mol of Compound (XVI). The reaction temperature can be appropriately selected by a person having ordinary skill in the art in accordance with the starting compound or reaction solvent used, but it is typically from 0° C. to room temperature. Also, the reaction is typically completed between 10 minutes to 2 hours, but the reaction time can be appropriately extended or reduced.

Also, the Compound (XVII) in which $LG_6$ is bromo can be obtained by reacting the Compound (XVII) in which $LG_6$ is methylsulfonyloxy, with lithium bromide in a solvent such as N,N-dimethylformamide, N-methyl-2-pyrrolidinone, or the like. In this case, lithium bromide is used in an amount of from 1 to 100 mol, preferably from 1 to 10 mol, relative to 1 mol of Compound (XVII) in which $LG_6$ is methylsulfonyloxy. The reaction temperature can be appropriately selected by a person having ordinary skill in the art in accordance with the starting compound or reaction solvent used, but it is typically from 0° C. to the boiling temperature of the solvent. Also, the reaction is typically completed between 1 hour to 24 hours, but the reaction time can be appropriately extended or reduced.

The resulting Compound (XVII) is subjected to isolation and purification by known separation and purification means such as, for example, concentration, concentration under reduced pressure, crystallization, solvent extraction, reprecipitation or chromatography, or may be subjected to the next process without isolation and purification.

(Process 12)

The present process is a method of subjecting the Compound (XVII) (wherein $LG_5$ and $LG_6$ have the same meaning as defined above, and $X_1$, $X_2$ and $X_3$ have the same meaning as the symbols for the above Formula (I)), obtained in the above-described Process 11, and Compound (XVIII) (wherein $PG_4$ is a protecting group such as tert-butoxycarbonyl, and $PG_5$ is a protecting group such as methyl, ethyl, or tert-butyl), to an alkylation reaction, thereby to produce Compound (XIX) (wherein $LG_5$, $PG_4$ and $PG_5$ have the same meaning as defined above, and $X_1$, $X_2$ and $X_3$ have the same meaning as the symbols for the above Formula (I)).

The Compound (XVIII) used in this process may be exemplified by 1-tert-butyl 4-ethyl piperidine-1,4-dicarboxylate, and the like. The Compound (XVIII) is commercially available or can be produced by a known method.

The alkylation reaction used in this process employs a method well known to those skilled in the art. In the alkylation reaction used in this process, specifically, for example, the Compound (XIX) can be synthesized by reacting the Compound (XVIII) in a solvent such as tetrahydrofuran with a base such as lithium diisopropylamide or lithium hexamethyldisilazide to produce an enolate form of the Compound (XVIII), followed by adding thereto the Compound (XVII) and if necessary an additive such as hexamethylphosphoric triamide or 1,3-dimethyl-2-imidazolidinone, and the like, thereby to produce the Compound (XIX). In this reaction, Compound (XVIII) is used in an amount of from 1 to 10 mol, preferably from 1 to 3 mol; and the base is used in an amount of from 1 to 10 mol, preferably from 1 to 3 mol; and the additive is used in an amount of from 1 to 100 mol, preferably from 1 to 10 mol, relative to 1 mol of Compound (XVII). The reaction temperature can be appropriately selected by a person having ordinary skill in the art in accordance with the starting compound or reaction solvent used, but it is typically from −78° C. to room temperature. Also, the reaction is typically completed within 1 hour to 48 hours, but the reaction time can be appropriately extended or reduced.

The resulting Compound (XIX) is subjected to isolation and purification by known separation and purification means such as, for example, concentration, concentration under reduced pressure, crystallization, solvent extraction, reprecipitation or chromatography, or may be subjected to the next process without isolation and purification.

(Process 13)

The present process is a method of subjecting Compound (XIX) (wherein $LG_5$, $PG_4$ and $PG_5$ have the same meaning as defined above, and $X_1$, $X_2$, and $X_3$ have the same meaning as the symbols for the above Formula (I)), obtained in the above-described Process 12, and Compound (V) (wherein $PG_2$ may be absent, or if present, it is a protective group such as 4-methoxybenzyl, 2,4-dimethoxybenzyl, benzyl, methoxymethyl, (2-(trimethylsilyl)ethoxy)methyl or tert-butyl, preferably (2-(trimethylsilyl)ethoxy)methyl, methoxymethyl or tert-butyl, and W has the same meaning as the symbol for the above Formula (I)), to an amination reaction, thereby to produce Compound (XX) (wherein $PG_2$, $PG_4$ and $PG_5$ have the same meaning as defined above, and $X_1$, $X_2$, $X_3$, and W have the same meaning as the symbols for the above Formula (I)).

The Compound (V) used in this process may be exemplified by 2-aminothiazole, 1-((2-(trimethylsilyl)ethoxy)methyl)-1H-pyrazol-3-amine, 1-tert-butyl-3-methyl-1H-pyrazol-5-amine, 1-tert-butyl-1H-pyrazol-5-amine, and the like. The Compound (V) is commercially available or can be prepared by a known method (e.g., Phosphorus, Sulfur and Silicon and the Related Elements, Vol. 177, No. 11, pages 2651-2659 (2002), and Journal of Chemical Research, Synopses, Vol. 6, page 198 (1979)).

The present process can also be carried out by the same method as used in Process 2, or a method equivalent thereto, or a combination of the same with a commonly used method.

The resulting Compound (XX) is subjected to isolation and purification by known separation and purification means such as, for example, concentration, concentration under reduced pressure, crystallization, solvent extraction, reprecipitation or chromatography, or may be subjected to the next process without isolation and purification.

(Process 14)

The present process is a method of deprotecting a protective group $PG_4$ of the Compound (XX) (wherein $PG_2$, $PG_4$ and $PG_5$ have the same meaning as defined above, and $X_1$, $X_2$, $X_3$, and W have the same meaning as the symbols for the above Formula (I)), obtained in the above-described Process 13, thereby to produce Compound (XXI) (wherein $PG_2$ and $PG_5$ have the same meaning as defined above, and $X_1$, $X_2$, $X_3$, and W have the same meaning as the symbols for the above Formula (I)).

For the deprotection reaction of $PG_4$, the method may vary depending on the type of the protective group or stability of the compound, but methods described in the literature [See T. W. Greene, Protective Groups in Organic Synthesis, John Wiley & Sons (1981)] or methods equivalent thereto can be carried out. For example, the Compound (XX) in which $PG_4$ is tert-butoxycarbonyl can be deprotected in a mixed solvent of trifluoroacetic acid and chloroform.

The present process can also be carried out by the same method as used in Process 3, or a method equivalent thereto, or a combination of the same with a commonly used method.

The resulting Compound (XXI) is subjected to isolation and purification by known separation and purification means such as, for example, concentration, concentration under reduced pressure, crystallization, solvent extraction, reprecipitation or chromatography, or may be subjected to the next process without isolation and purification.

(Process 15)

The present process is a method of subjecting Compound (XXI) (wherein $PG_2$ and $PG_5$ have the same meaning as defined above, and $X_1$, $X_2$, $X_3$, and W have the same meaning as the symbols for the above Formula (I)), obtained in the above-described Process 14, and Compound (VIII) (wherein $LG_2$ represents a leaving group such as chloride or hydroxy, and $R_2$ and $R_3$ have the same meaning as the symbols for the above Formula (I)), to a condensation reaction, thereby to produce Compound (XXII) (wherein $PG_2$ and $PG_5$ have the same meaning as defined above, and $R_2$, $R_3$, $X_1$, $X_2$, $X_3$, and W have the same meaning as the symbols for the above Formula (I)).

The Compound (VIII) used in this process may be exemplified by 3-chloro-2-fluorobenzoic acid or 2-fluoro-3-(trifluoromethyl)benzoic acid. The Compound (VIII) is commercially available, or can be produced by a known method.

The present process can also be carried out by the same method as used in Process 4, or a method equivalent thereto, or a combination of the same with a commonly used method.

The resulting Compound (XXII) is subjected to isolation and purification by known separation and purification means such as, for example, concentration, concentration under reduced pressure, crystallization, solvent extraction, reprecipitation or chromatography, or may be subjected to the next process without isolation and purification.

(Process 16)

The present process is a method of deprotecting a protective group $PG_2$ of the Compound (XXII) (wherein $PG_2$ and $PG_5$ have the same meaning as defined above, $R_2$, $R_3$, $X_1$, $X_2$, $X_3$, and W have the same meaning as the symbols for the above Formula (I)), obtained in the above-described Process 15, thereby to produce Compound (XXIII) (wherein $PG_5$ has the same meaning as defined above, and $R_2$, $R_3$, $X_1$, $X_2$, $X_3$, and W have the same meaning as the symbols for the above Formula (I)).

For the deprotection reaction of $PG_2$, the method may vary depending on the type of the protective group or stability of the compound, but methods described in the literature [See T. W. Greene, Protective Groups in Organic Synthesis, John Wiley & Sons (1981)] or methods equivalent thereto can be carried out.

For example, the Compound (XXII) in which $PG_2$ is tert-butyl can be deprotected in a solvent of formic acid. The reaction temperature can be appropriately selected by a person having ordinary skill in the art in accordance with the starting compound or reaction solvent used, but it is typically from room temperature to the boiling point of the solvent. Also, the reaction is typically completed between 1 hour to 24 hours, but the reaction time can be appropriately extended or reduced.

The resulting Compound (XXIII) is subjected to isolation and purification by known separation and purification means such as, for example, concentration, concentration under reduced pressure, crystallization, solvent extraction, reprecipitation or chromatography, or may be subjected to the next process without isolation and purification.

(Process 17)

The present process is a method of deprotecting a protective group $PG_5$ of the Compound (XXIII) (wherein $PG_5$ has the same meaning as defined above, and $R_2$, $R_3$, $X_1$, $X_2$, $X_3$, and W have the same meaning as the symbols for the above Formula (I)), obtained in the above-described Process 16, thereby to produce Compound (XXIV) (wherein $R_2$, $R_3$, $X_1$, $X_2$, $X_3$, and W have the same meaning as the symbols for the above Formula (I)).

For the deprotection reaction of $PG_5$, the method may vary depending on the type of the protective group or stability of the compound, but methods described in the literature [See T. W. Greene, Protective Groups in Organic Synthesis, John Wiley & Sons (1981)] or methods equivalent thereto can be carried out. For example, the Compound (XXIII) in which $PG_5$ is ethyl can be deprotected in a solvent such as methanol or ethanol using aqueous sodium hydroxide solution, or the like. When sodium hydroxide is used for the deprotection reaction, sodium hydroxide is used in an amount of from 1 to 100 mol, preferably from 1 to 10 mol, relative to 1 mol of Compound (XXIII).

The reaction temperature can be appropriately selected by a person having ordinary skill in the art in accordance with the starting compound or reaction solvent used, but it is typically from room temperature to the boiling point of the solvent. Also, the reaction is typically completed between 1 hour to 24 hours, but the reaction time can be appropriately extended or reduced.

The resulting Compound (XXIV) is subjected to isolation and purification by known separation and purification means such as, for example, concentration, concentration under reduced pressure, crystallization, solvent extraction, reprecipitation or chromatography, or may be subjected to the next process without isolation and purification.

(Process 18)

The present process is a method of subjecting the Compound (XXIV) (wherein $R_2$, $R_3$, $X_1$, $X_2$, $X_3$, and W have the same meaning as the symbols for the above Formula (I)), obtained in the above Process 17, and Compound (XXV) (wherein $R_{a2}$ and $R_{a2}'$ have the same meaning as the symbols for the above Formula (I)), to a condensation reaction, thereby to produce Compound (I-3) (wherein $R_2$, $R_3$, $R_{a2}$, $R_{a2}'$, $X_1$, $X_2$, $X_3$, and W have the same meaning as the symbols for the above Formula (I)).

The Compound (XXIV) used in this reaction can be exemplified by ammonium chloride, methylamine, dimethylamine, and the like. The Compound (XXV) is commercially available, or can be prepared by a known method.

The condensation reaction used in this process can be conducted using a carboxylic acid of the Compound (XXIV) or a reactive derivative thereof, and the Compound (XXV). The "reactive derivative" of the Compound (XXIV) can be exemplified by a mixed acid anhydride, an activated ester, an activated amide, and the like; and they can be obtained in accordance with the method described in Science of Synthesis (2005), Vol. 21, 43. Specifically, for example, the condensation reaction can be conducted using the Compound (XXIV) and the Compound (XXV) in a solvent such as, for example, tetrahydrofuran, dimethylsufoxide, N,N-dimethylformamide, 1,4-dioxane, dichloromethane, or chloroform, together with a condensation agent such as 1-(3-dimethylaminopropyl)-3-ethylcarbodiimide, and 1-hydroxybenzotriazole. In this case, the Compound (XXV) is used in an amount of from 1 to 10 mol, preferably 1 to 3 mol; and the condensation agent is used in an amount of 1 to 10 mol, preferably 1 to 3 mol, relative to 1 mol of Compound (XXIV). The reaction temperature is appropriately selected by a person skilled in the art in accordance with the starting compound or reaction solvent used, but it is typically from room temperature to the boiling point of the solvent used in the reaction. Also, the reaction is typically completed between 1 hour to 24 hours, but the reaction time can be appropriately extended or reduced.

The resulting Compound (I-3) is subjected to isolation and purification by known separation and purification means such as, for example, concentration, concentration under reduced pressure, crystallization, solvent extraction, reprecipitation or chromatography.

Also in the case where $R_1$ is $CONR_{a4}OR_{a4}'$ (wherein $R_{a4}$ and $R_{a4}'$ have the same meaning as the symbols for the above Formula (I)), the relevant reaction can be carried out by the same method as used in Process 18 above, or a method equivalent thereto, or a combination of the same with a commonly used method.

Among the compounds represented by the General Formula (I) (wherein $R_1$, $R_2$, $R_3$, $X_1$, $X_2$, $X_3$, and W have the same meaning as defined in the above) according to the invention, the compound of Formula (I-4):

(I-4)

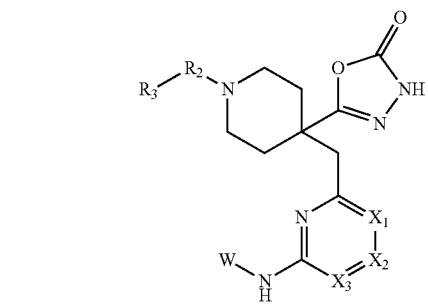

(wherein R₁ is 1,3,4-oxadiazol-2(3H)-one; and $R_2$, $R_3$, $X_1$, $X_2$, $X_3$, and W have the same meaning as the symbols for the above Formula (I)) can be prepared by, for example, the following method.

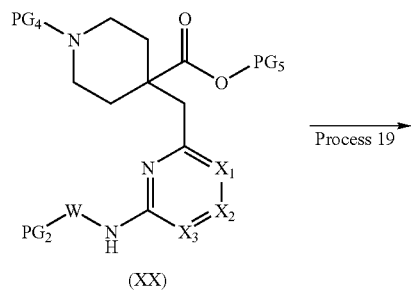

(XX)

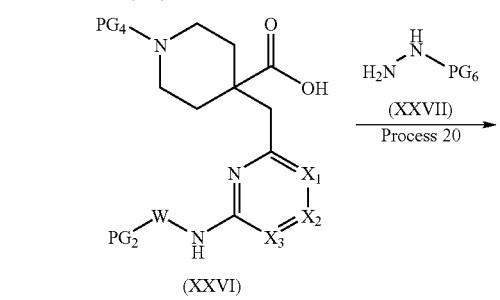

(XXVI)

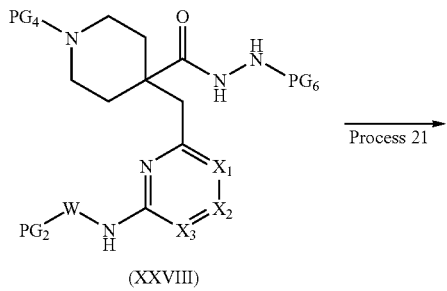

(XXVIII)

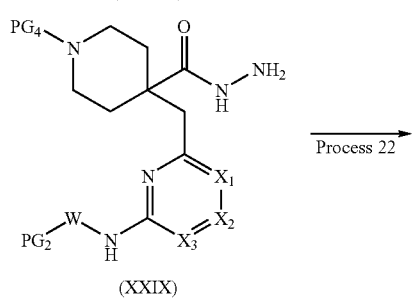

(XXIX)

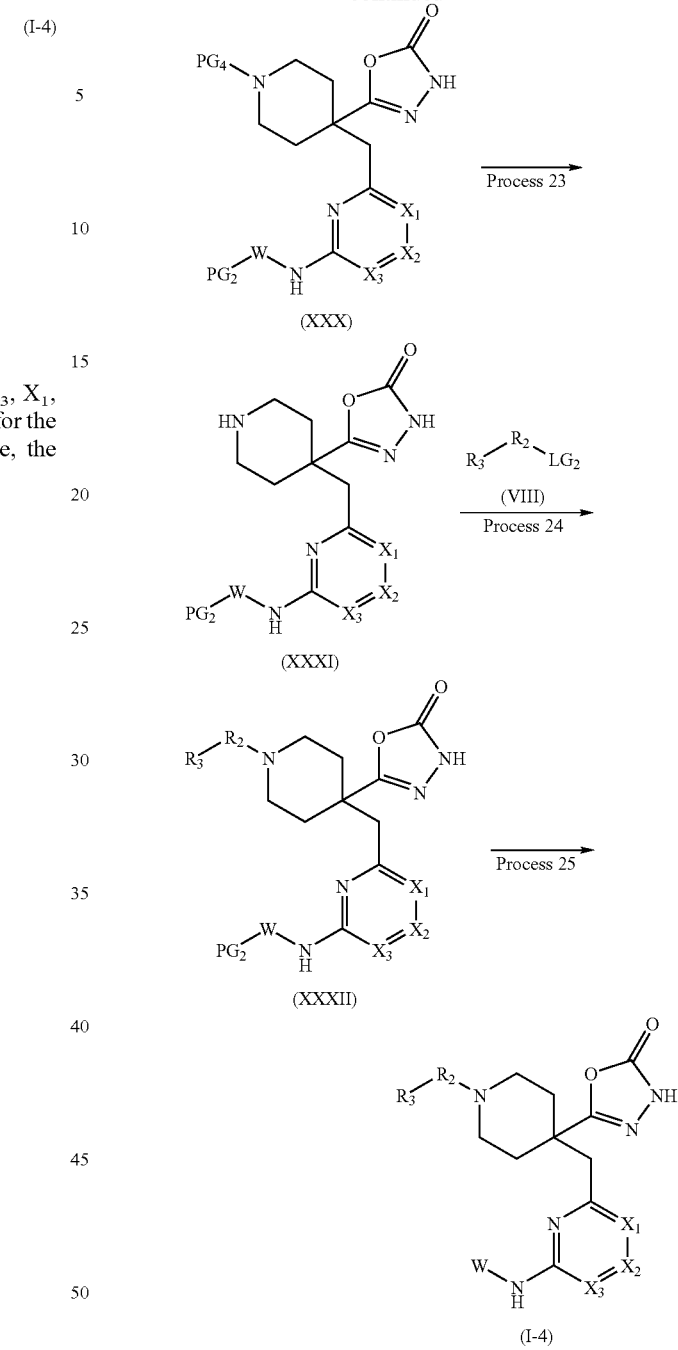

(Process 19)

The present process is a method of deprotecting a protective group $PG_5$ of the Compound (XX) (wherein $PG_2$, $PG_4$ and $PG_5$ have the same meaning as defined above, and $X_1$, $X_2$, $X_3$, and W have the same meaning as the symbols for the above Formula (I)), obtained in the above-described Process 13, thereby to produce Compound (XXVI) (wherein $PG_2$ and $PG_4$ have the same meaning as defined above, and $X_1$, $X_2$, $X_3$, and W have the same meaning as the symbols for the above Formula (I)).

For the deprotection reaction of $PG_5$, the method may vary depending on the type of the protective group or stability of the compound, but methods described in the literature [See T. W. Greene, Protective Groups in Organic Synthesis, John Wiley & Sons (1981)] or methods equivalent thereto can be carried out. For example, the Compound (XX) in which $PG_5$ is ethyl can be deprotected in a solvent such as methanol or ethanol using aqueous sodium hydroxide solution, or the like.

The present process can also be carried out by the same method as used in Process 17, or a method equivalent thereto, or a combination of the same with a commonly used method.

The resulting Compound (XXVI) is subjected to isolation and purification by known separation and purification means such as, for example, concentration, concentration under reduced pressure, crystallization, solvent extraction, reprecipitation or chromatography, or may be subjected to the next process without isolation and purification.

(Process 20)

The present process is a method of subjecting Compound (XXVI) (wherein $PG_2$ and $PG_4$ have the same meaning as defined above, and $X_1$, $X_2$, $X_3$ and W have the same meaning as the symbols for the above Formula (I)), obtained in the above-described Process 19, and Compound (XXVII) (wherein $PG_6$ may be absent, or if present, it is a protective group such as tert-butoxycarbonyl, ethoxycarbonyl or benzyloxycarbonyl), to a condensation reaction, thereby to produce Compound (XXVIII) (wherein $PG_2$, $PG_4$ and $PG_6$ have the same meaning as defined above, and $X_1$, $X_2$, $X_3$, and W have the same meaning as the symbols for the above Formula (I)).

The Compound (XXVII) used in this process may be exemplified by tert-butylcarbazate, ethoxycarbonylhydrazine, benzyloxycarbonylhydrazine, or hydrazine. The Compound (XXVII) is commercially available, or can be produced by a known method.

The present process can also be carried out by the same method as used in Process 18, or a method equivalent thereto, or a combination of the same with a commonly used method.

The resulting Compound (XXVIII) is subjected to isolation and purification by known separation and purification means such as, for example, concentration, concentration under reduced pressure, crystallization, solvent extraction, reprecipitation or chromatography, or may be subjected to the next process without isolation and purification.

(Process 21)

The present process is a method of deprotecting a protective group $PG_6$ of the Compound (XXVIII) (wherein $PG_2$, $PG_4$ and $PG_6$ have the same meaning as defined above, and $X_1$, $X_2$, $X_3$, and W have the same meaning as the symbols for the above Formula (I)), obtained in the above-described Process 20, thereby to produce Compound (XXIX) (wherein $PG_2$ and $PG_4$ have the same meaning as defined above, and $X_1$, $X_2$, $X_3$, and W have the same meaning as the symbols for the above Formula (I)).

For the deprotection reaction of $PG_6$, the method may vary depending on the type of the protective group or stability of the compound, but methods described in the literature [See T. W. Greene, Protective Groups in Organic Synthesis, John Wiley & Sons (1981)] or methods equivalent thereto can be carried out. For example, the Compound (XXVIII) in which $PG_6$ is benzyloxycarbonyl can be deprotected by hydrogenation in a solvent such as methanol or ethanol using palladium hydroxide on carbon, or the like. When palladium hydroxide on carbon is used for the deprotection reaction, palladium hydroxide on carbon is used in an amount of from 0.1 to 10 mol, preferably from 0.1 to 5 mol, relative to 1 mol of Compound (XXVIII). The reaction temperature can be appropriately selected by a person having ordinary skill in the art in accordance with the starting compound or reaction solvent used, but it is typically from room temperature to the boiling point of the solvent. The reaction pressure is typically from 1 atm to 100 atm. Also, the reaction is typically completed between 1 hour to 24 hours, but the reaction time can be appropriately extended or reduced.

The resulting Compound (XXIX) is subjected to isolation and purification by known separation and purification means such as, for example, concentration, concentration under reduced pressure, crystallization, solvent extraction, reprecipitation or chromatography, or may be subjected to the next process without isolation and purification.

(Process 22)

The present process is a method of converting a carbohydrazide group of the Compound (XXIX) (wherein $PG_2$ and $PG_4$ have the same meaning as defined above, and $X_1$, $X_2$, $X_3$, and W have the same meaning as the symbols for the above Formula (I)), obtained in the above-described Process 21, into a heterocyclic group thereof, thereby to produce Compound (XXX) (wherein $PG_2$ and $PG_4$ have the same meaning as defined above, and $X_1$, $X_2$, $X_3$, and W have the same meaning as the symbols for the above Formula (I)).

The reaction used in this process employs a method well known to a person skilled in the art. The reaction can be carried out in accordance with the method described in literature, for example, Journal of Medicinal Chemistry (1993) Vol. 36, Page 1090. In the reaction used in this process, specifically, for example, the Compound (XXX) can be synthesized by reacting the Compound (XXIX) with 1,1'-carbonyldiimidazole, if necessary using a base such as triethylamine or N,N-diisopropylethylamine, in the presence of a solvent such as, for example, tetrahydrofuran, 1,4-dioxane or N-methyl-2-pyrrolidinone. In this case, 1,1'-carbonyldiimidazole is used in an amount of from 1 to 10 mol, preferably 1 to 3 mol; if necessary, a base is used in an amount of from 1 to 10 mol, preferable from 1 to 3 mol, relative to 1 mol of compound (XXIX). The reaction temperature is appropriately selected by a person skilled in the art in accordance with the starting compound or reaction solvent used, but it is typically from room temperature to the boiling point of the solvent used in the reaction. Also, the reaction is typically completed between 1 hour to 24 hours, but the reaction time can be appropriately extended or reduced.

The resulting Compound (XXX) is subjected to isolation and purification by known separation and purification means such as, for example, concentration, concentration under reduced pressure, crystallization, solvent extraction, reprecipitation or chromatography, or may be subjected to the next process without isolation and purification.

(Process 23)

The present process is a method of deprotecting a protective group $PG_4$ of the Compound (XXX) (wherein $PG_2$ and $PG_4$ have the same meaning as defined above, and $X_1$, $X_2$, $X_3$, and W have the same meaning as the symbols for the above Formula (I)), obtained in the above-described Process 22, thereby to produce Compound (XXXI) (wherein $PG_2$ has the same meaning as defined above, and $X_1$, $X_2$, $X_3$, and W have the same meaning as the symbols for the above Formula (I)).

For the deprotection reaction of $PG_4$, the method may vary depending on the type of the protective group or stability of the compound, but methods described in the literature [See T. W. Greene, Protective Groups in Organic Synthesis, John Wiley & Sons (1981)] or methods equivalent thereto can be carried out. For example, the Compound (XXX) in which $PG_4$ is tert-butoxycarbonyl can be deprotected in a mixed solvent of trifluoroacetic acid and chloroform.

The present process can also be carried out by the same method as used in Process 3, or a method equivalent thereto, or a combination of the same with a commonly used method.

The resulting Compound (XXXI) is subjected to isolation and purification by known separation and purification means such as, for example, concentration, concentration under reduced pressure, crystallization, solvent extraction, reprecipitation or chromatography, or may be subjected to the next process without isolation and purification.

(Process 24)

The present process is a method of subjecting Compound (XXXI) (wherein $PG_2$ has the same meaning as defined above, and $X_1$, $X_2$, $X_3$, and W have the same meaning as the symbols for the above Formula (I)), obtained in the above-described Process 23, and Compound (VIII) (wherein $LG_2$ represents a leaving group such as chloride or hydroxy, and $R_2$ and $R_3$ have the same meaning as the symbols for the above Formula (I)), to a condensation reaction, thereby to produce Compound (XXXII) (wherein $PG_2$ has the same meaning as defined above; $R_2$, $R_3$, $X_1$, $X_2$, $X_3$, and W have the same meaning as the symbols for the above Formula (I)).

The Compound (VIII) used in this process may be exemplified by 3-chloro-2-fluorobenzoic acid, 2-fluoro-3-(trifluoromethyl)benzoic acid, 2-(trifluoromethyl)benzenesulfonyl chloride or 2,3-dichlorobenzenesulfonyl chloride. The Compound (VIII) is commercially available, or can be produced by a known method.

The present process can also be carried out by the same method as used in Process 4, or a method equivalent thereto, or a combination of the same with a commonly used method.

The resulting Compound (XXXII) is subjected to isolation and purification by known separation and purification means such as, for example, concentration, concentration under reduced pressure, crystallization, solvent extraction, reprecipitation or chromatography, or may be subjected to the next process without isolation and purification.

If there is no need for deprotection regarding the Compound (XXXII), then the Compound (XV) per se becomes the compound according to the present invention without conducting Process 25 and the processes thereafter.

(Process 25)

The present process is a method of deprotecting a protective group $PG_2$ of the Compound (XXXII) (wherein $PG_2$ has the same meaning as defined above, $R_2$, $R_3$, $X_1$, $X_2$, $X_3$, and W have the same meaning as the symbols for the above Formula (I)), obtained in the above-described Process 24, thereby to produce Compound (I-4) (wherein $R_2$, $R_3$, $X_1$, $X_2$, $X_3$, and W have the same meaning as the symbols for the above Formula (I)).

For the deprotection reaction of $PG_2$, the method may vary depending on the type of the protective group or stability of the compound, but methods described in the literature [See T. W. Greene, Protective Groups in Organic Synthesis, John Wiley & Sons (1981)] or methods equivalent thereto can be carried out. For example, the Compound (XXXII) (wherein $PG_2$ is tert-butyl) can be deprotected in a solvent of formic acid.

The present process can also be carried out by the same method as used in Process 16, or a method equivalent thereto, or a combination of the same with a commonly used method.

The resulting Compound (I-4) is subjected to isolation and purification by known separation and purification means such as, for example, concentration, concentration under reduced pressure, crystallization, solvent extraction, reprecipitation or chromatography.

The Compound (XX-1) (wherein $PG_2$, $PG_4$ and $PG_5$ have the same meaning as defined above; $X_2$ is $CX_{2a}$; $X_1$, $X_3$, and W have the same meaning as the symbols for the above Formula (I)) can be produced, for example, by the following method:

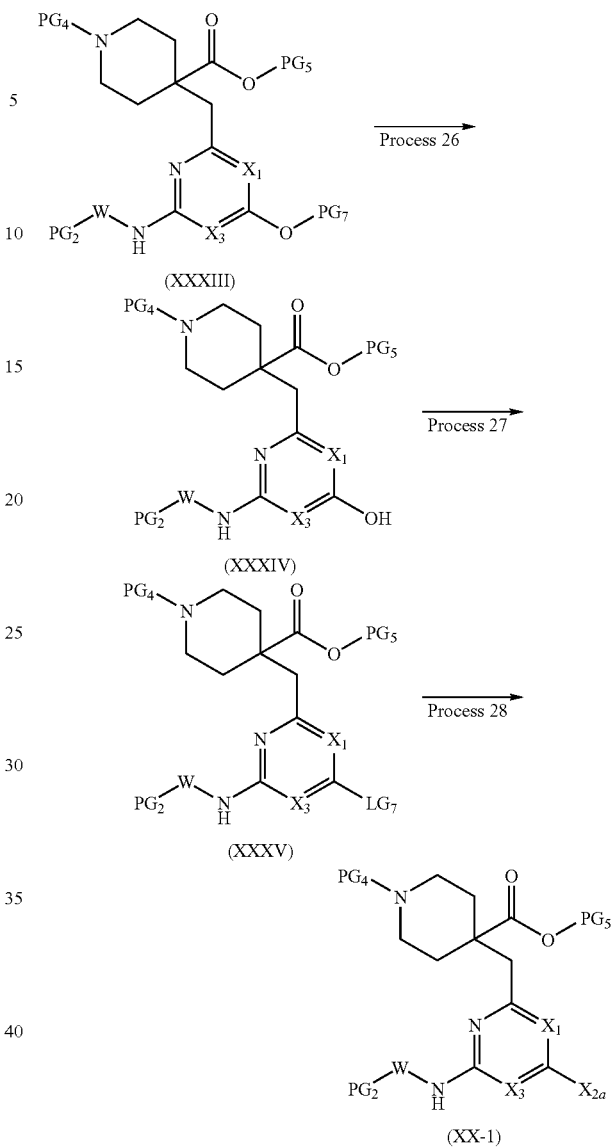

(Process 26)

The present process is a method of deprotecting a protective group $PG_7$ of the Compound (XXXIII) (wherein $PG_7$ is a protecting group such as benzyl; $PG_2$, $PG_4$ and $PG_5$ have the same meaning as defined above; $X_1$, $X_3$, and W have the same meaning as the symbols for the above Formula (I)), thereby to produce Compound (XXXIV) (wherein $PG_2$, $PG_4$ and $PG_5$ have the same meaning as defined above, and $X_1$, $X_3$, and W have the same meaning as the symbols for the above Formula (I)).

The Compound (XXXIII) can be obtained in the same manner as in the steps of Process 11 to 13 using such as (4-(benzyloxy)-6-chloropyridin-2-yl)methanol.

For the deprotection reaction of $PG_7$, the method may vary depending on the type of the protective group or stability of the compound, but methods described in the literature [See T. W. Greene, Protective Groups in Organic Synthesis, John Wiley & Sons (1981)] or methods equivalent thereto can be carried out. For example, the Compound (XXXIII) in which $PG_7$ is benzyloxycarbonyl can be deprotected by hydrogenation in a solvent such as methanol or ethanol using palladium hydroxide on carbon, or the like.

The present process can also be carried out by the same method as used in Process 21, or a method equivalent thereto, or a combination of the same with a commonly used method. The resulting Compound (XXXIV) is subjected to isolation and purification by known separation and purification means such as, for example, concentration, concentration under reduced pressure, crystallization, solvent extraction, reprecipitation or chromatography, or may be subjected to the next process without isolation and purification.

(Process 27)

The present process is a method of converting a hydroxy group of the Compound (XXXIV) (wherein $PG_2$, $PG_4$ and $PG_5$ have the same meaning as defined above, and $X_1$, $X_3$, and W have the same meaning as the symbols for the above Formula (I)), obtained in the above-described Process 26, into a leaving group such as, for example, trifluoromethylsulfonyloxy, thereby to produce Compound (XXXV) (wherein $LG_7$ is a leaving group, $PG_2$, $PG_4$ and $PG_5$ have the same meaning as defined above, and $X_1$, $X_3$, and W has the same meaning as the symbols for the above Formula (I)).

The reaction used in this process employs a method well known to those skilled in the art. In the reaction used in this process, specifically, for example, Compound (XXXV) in which $LG_7$ is trifluoromethylsulfonyloxy can be obtained by reacting the Compound (XXXIV) with trifluoromethanesulfonic anhydride in a solvent such as chloroform, methylene chloride, tetrahydrofuran, N,N-dimethylformamide, diethyl ether or ethyl acetate, in the presence of a base such as triethylamine or diisopropylethylamine. In this case, trifluoromethanesulfonic anhydride is used in an amount of from 1 to 10 mol, preferably from 1 to 3 mol; and the base is used in an amount of from 1 to 20 mol, preferably from 1 to 6 mol, relative to 1 mol of Compound (XXXIV). The reaction temperature can be appropriately selected by a person having ordinary skill in the art in accordance with the starting compound or reaction solvent used, but it is typically from 0° C. to room temperature. Also, the reaction is typically completed between 10 minutes to 2 hours, but the reaction time can be appropriately extended or reduced.

The resulting Compound (XXXV) is subjected to isolation and purification by known separation and purification means such as, for example, concentration, concentration under reduced pressure, crystallization, solvent extraction, reprecipitation or chromatography, or may be subjected to the next process without isolation and purification.

(Process 28)

The present process is a method of subjecting Compound (XXXV) (wherein $LG_7$, $PG_2$, $PG_4$ and $PG_5$ have the same meaning as defined above, and $X_1$, $X_3$, and W have the same meaning as the symbols for the above Formula (I)), obtained in the above-described Process 27, and boronic acid, to a coupling reaction, thereby to produce Compound (XX-1) (wherein $PG_2$, $PG_4$ and $PG_5$ have the same meaning as defined above, and $X_1$, $X_{2a}$, $X_3$, and W have the same meaning as the symbols for the above Formula (I)).

The coupling reaction used in this process employs a method well known to those skilled in the art. In the coupling reaction used in the process, specifically, for example, the synthesis can be conducted by reacting the Compound (XXXV) and boronic acid, such as phenylboronic acid, in a solvent such as 1,4-dioxane, 1,2-dimethoxyethane, tetrahydrofuran or toluene, using a palladium catalyst such as (1,1'-bis(diphenylphosphino)ferrocene)dichloropalladium(II); and a base such as cesium carbonate or potassium phosphate. In the reaction, 0.5 to 3 mol, preferably 1 mol of phenylboronic acid is used; 0.001 to 1 mol, preferably 0.05 to 0.5 mol, of the palladium catalyst is used; and 1 to 10 mol, preferably 1 to 3 mol, of the base is used, relative to 1 mol of compound (XXXV). The reaction temperature is appropriately selected by a person skilled in the art in accordance with the starting compound or reaction solvent used, but it is typically from 50° C. to the boiling point of the solvent used in the reaction. Also, the reaction is typically completed between 1 hour to 24 hours, but the reaction time can be appropriately extended or reduced.

The resulting Compound (XX-1) is subjected to isolation and purification by known separation and purification means such as, for example, concentration, concentration under reduced pressure, crystallization, solvent extraction, reprecipitation or chromatography, or may be subjected to the next process without isolation and purification.

The Compound (XXXVIII) (wherein $PG_8$ has the same meaning as defined above, $R_3$ and $R_x$ have the same meaning as the symbols for the above Formula (I)) can be produced, for example, by the following method:

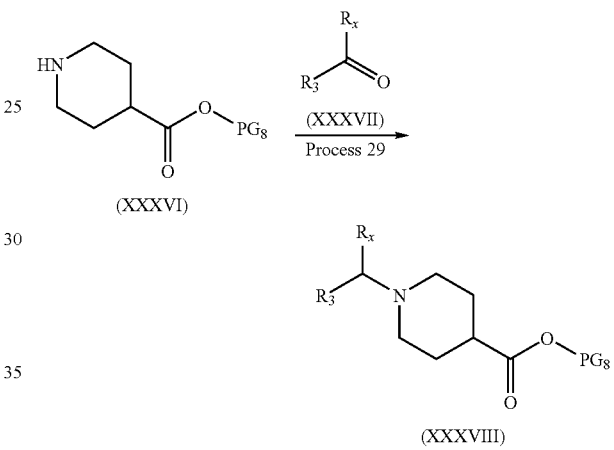

(Process 29)

The present process is a method of subjecting the Compound (XXXVI) (wherein $PG_8$ is a protecting group such as methyl, ethyl or tert-butyl), and Compound (XXXVII) (wherein $R_3$ and $R_x$ have the same meaning as the symbol for the above Formula (I)), to a reductive condensation, thereby to produce Compound (XXXVIII) (wherein $PG_8$ has the same meaning as defined above, and $R_3$ and $R_x$ have the same meaning as the symbols for the above Formula (I)).

The Compound (XXXVI) used in this process may be exemplified by ethyl isonipecotate, and the like. The Compound (XXXVI) is commercially available.

The Compound (XXXVII) used in this process may be exemplified by 2,2,2-trifluoro-1-(3-(trifluoromethyl)phenyl)ethanone, and the like. The Compound (XXXVII) is commercially available.

The reductive condensation used in this process employs a method well known to those skilled in the art. The reductive condensation, for example, can be carried out in accordance with a method described in Tetrahedron Letters (1990), Vol. 31, 5547. In the reductive condensation used in this process, specifically, for example, the Compound (XXXVIII) can be synthesized by reacting the Compound (XXXVI) and the Compound (XXXVII) in a solvent such as methylene chloride with a base such as triethylamine and a Lewis acid such as titanium(IV) chloride to produce a Schiff base of the Compound (XXXVI), followed by adding thereto a reductive agent such as sodium cyanoborohydride in a solvent such as methanol. In this reaction, the Compound (XXXVII) is used in an amount of from 1 to 10 mol, preferably from 1 to 3 mol; the base is used in an amount of from 1 to 10 mol, preferably from 1 to 5 mol; the Lewis acid is used in an amount of from 0.5 to 5 mol, preferably from 0.5 to 2.5 mol; and the reductive agent is used in an amount of from 1 to 100 mol, preferably from 3 to 10 mol, relative to 1 mol of Compound (XXXVI). The reaction temperature can be appropriately selected by a person having ordinary skill in the art in accordance with the starting compound or reaction solvent used, but it is typically from room temperature to the boiling point of the solvent used in the reaction. Also, the reaction is typically completed within 1 hour to 48 hours, but the reaction time can be appropriately extended or reduced.

The resulting Compound (XXXVIII) is subjected to isolation and purification by known separation and purification means such as, for example, concentration, concentration under reduced pressure, crystallization, solvent extraction, reprecipitation or chromatography, or maybe subjected to the next process without isolation and purification.

Next, the Aurora A and Aurora B inhibitory actions of the compound of General Formula (I) according to the invention will be explained below.

Aurora A Inhibitory Activity (1) Purification of Aurora A cDNA of N-terminal His-tagged human Aurora A was integrated into an expression vector, which was then highly expressed in *Escherichia coli* BL21-CodonPlus(DE3)-RIL cells. The *Escherichia coli* was harvested and lysed, and then the His-tagged human Aurora A protein was applied onto a nickel chelate column and eluted from the column with imidazole. The active fractions were desalted with a desalting column to give a purified enzyme.

(2) Measurement of Activity of Aurora A

For measurement of the activity of Aurora A, the substrate used was a synthetic peptide (5-FAM (5-carboxyfluorescein)-γ-aminobutyric acid-Ala-Leu-Arg-Arg-Ala-Ser-Leu-Gly-NH$_2$) (SEQ.ID.NO.: 1), which was purchased from Toray Research Center, Inc.

For the phosphorylation reaction, the method by Upstate, Inc. [Kinase Profiler™ Assay Protocols] was referred to, and phosphorylation of the substrate was detected using IMAP® technology (Molecular Devices, Co. Ltd.) (Gaudet E W. et. al, J. Biomol. Screen, 8, 164-175 (2003)). Concretely, the phosphorylation reaction and the detection were carried out as follows:

The phosphorylation reaction was conducted using 384 well plate, and the reaction volume was 10 µl/well. The reaction buffer is comprised of 50 mM Tris-chloride buffer (pH 7.4), 15 mM magnesium acetate, and 0.2 mM ethylenediamine-N,N,N',N'-tetraacetic acid (EDTA). Thereto, the purified Aurora A protein, 100 nM of the peptide substrate, and 20 µM of adenosine 5'-triphosphate (ATP) were added, and then the reaction was carried out at 30° C. for 120 minutes.

Thereafter, in order to terminate and detect the reaction, 30 µl of the IMAP (registered trademark) binding reagent (IMAP Progressive Binding Reagent, R7284) that had been diluted (1:400) in the 1×IMAP binding buffer A (IMAP Progressive Binding Buffer A, 5× stock, R7282) was added to each well. The solution stood still for 60 minutes in the dark, and then fluorescence polarization was measured using a high-end microplate reader (excitation wavelength: 485 nm; emission wavelength: 520 nm).

The compound to be tested was added to the reaction system such that a dilution series of the compound in dimethylsulfoxide (DMSO) was prepared, and then 0.5 µL of this solution was added for the testing to each well. Each control well was provided by adding 0.5 µL of DMSO to the well in place of the DMSO solution containing the compound to be tested.

Aurora B Inhibitory Activity (1) Measurement of Activity of Aurora B (Method A)

An assay development kit for IMAP (registered trademark) (Aurora B), purchased from Carna Biosciences, Inc., was used for phosphorylation reaction, and the phosphorylation of a substrate was detected using the IMAP technology. The assay development kit used is comprised of an assay buffer, GST-tagged human Aurora B(AurB)/His-tagged human INCENP complex proteins (amino acid sequence: 803-916, AAU04398.1), and an ATP/substrate solution. Using the same, the phosphorylation reaction was conducted in accordance with a partially revised protocol attached to the kit, and then the phosphorylation of the substrate was detected using the IMAP technology.

For the phosphorylation reaction, 384 well plate was used, and the reaction volume was 10 µl/well. The composition of the reaction buffer (assay buffer) is comprised of 20 mM of HEPES buffer (pH 7.4), 0.01% Tween-20, and 2 mM of dithiothreitol (DTT). Thereto, AurB/INCENP complex protein, 100 nM of the substrate, and 40 µM of ATP, and 1 mM of magnesium salt were added, and then the reaction was conducted at 25° C. for 45 minutes. Thereafter, in order to terminate and detect the reaction, 30 µl of the IMAP (registered trademark) binding reagent (IMAP Progressive Binding Reagent, R7284) that had been diluted (1:400) in the 1×IMAP binding buffer A (IMAP Progressive Binding Buffer A, 5× stock, R7282) was added to each well. The solution stood still for 60 minutes in the dark, and then fluorescence polarization was measured using a high-end microplate reader (excitation wavelength: 485 nm; emission wavelength: 520 nm).

The compound to be tested was added to the reaction system such that a dilution series of the compound in DMSO was prepared, and then 0.5 µL of this solution was added for the testing to each well. Each control well was provided by adding 0.5 µL of DMSO to the well in place of the DMSO solution containing the compound to be tested.

(2) Measurement of Activity of Aurora B (Method B)

(a) Purification of Aurora B cDNA of human Aurora B having histidine tag fused at the amino terminal was integrated into an expression vector, which was then highly expressed in *Escherichia coli* BL21-CodonPlus(DE3)-RIL cells. The *Escherichia coli* cells were recovered and solubilized, and then the histidine-tagged Aurora A protein was adsorbed onto a nickel chelate column and eluted from the column with imidazole. The active fraction was desalted with a desalting column to give a pure enzyme.

(b) Measurement of Activity of Aurora B

For measurement of the activity of Aurora B, the substrate used was Kemptide (Leu-Arg-Arg-Ala-Ser-Leu-Gly) (SEQ.ID.NO.: 2), a synthetic peptide purchased from Sigma-Aldrich, Inc. [Certificate of analysis (Upstate, Inc.)].

Reaction was conducted by a partial modification of the method of activity measurement for Aurora A. The amount of the reaction liquid was 21.1 µL, and the composition of the reaction buffer (R2 buffer) was 50 mM Tris-hydrochloride buffer (pH 7.4)/15 mM magnesium acetate/0.2 mM ethylenediamine-N,N,N',N'-tetraacetic acid (EDTA). To this, purified Aurora B, 100 µM of a substrate peptide, 100 µM of unlabeled adenosine triphosphate (ATP) and 1 µCi of [γ-$^{33}$P] labeled ATP (2,500 Ci/mmole or more) were added, and the mixture was reacted at 30° C. for 20 minutes. Then, 10 µL of 350 mM phosphate buffer was added to the reaction system to stop the reaction. The substrate peptide was adsorbed on a P81 paper filter 96-well plate and then washed with 130 mM phosphate buffer for several times. The radiation activity of the peptide was measured with a liquid scintillation counter. The [γ-$^{33}$P] labeled ATP was purchased from Amersham Biosciences Co., Ltd.

The compound to be tested was added to the reaction system such that a dilution series of the compound in dimethylsulfoxide was first prepared, and 1.1 μL of this solution was added. A control was provided by adding 1.1 μL of DMSO to the reaction system.

Using the above method (in the measurement of activity of Aurora B, Method A was used), the results for measurement of the activities of Aurora A and Aurora B were obtained as shown in Table 1. The compound according to the invention exhibited excellent Aurora A selective inhibitory activity. Similar results are obtained when Method B is used in the measurement of activity of Aurora B.

TABLE 1

| Example | Inhibitory activity for Aurora A (IC$_{50}$, nM) | Inhibitory activity for Aurora B (IC$_{50}$, nM) |
| --- | --- | --- |
| Example 2 | 0.91 | 368.7 |
| Example 3 | 1.60 | 400 |
| Example 4 | 1.14 | >1000 |
| Example 5 | 0.63 | 554.9 |
| Example 6 | 1.57 | >1000 |
| Example 7 | 0.61 | 134.8 |
| Example 8 | 0.79 | 554.9 |
| Example 9 | 0.25 | 35.8 |
| Example 10 | 0.27 | 165.8 |
| Example 11 | 0.26 | 235.8 |
| Example 13 | 2.55 | 608.9 |
| Example 14 | 0.40 | >1000 |
| Example 15 | 0.25 | 77.5 |
| Example 16 | 0.41 | 156.7 |
| Example 17 | 0.30 | 380.8 |
| Example 18 | 1.23 | >1000 |
| Example 19 | 1.27 | >1000 |

Next, the cell growth suppressive action of the compound of the General Formula (I) according to the invention will be explained below.

Method for Judging the Pharmaceutical Effect Using Cells
a) Reagent

Fetal calf serum (FCS) was purchased from Moregate Biotech, and DMEM medium was purchased from Invitrogen Corp. WST-8 was purchased from Kishida Chemical Co., Ltd.

b) Cells

Human cervical cancer cells (HeLa S3) were obtained from the American Type Culture Collection (ATCC).

c) Method of Judging the Effect

Cells were suspended in a DMEM medium containing 10% FCS, and the cell suspension was dispensed to a 96-well plastic plate at a rate of 750 cells/100 microliters per well. The plate was incubated overnight in 5% CO$_2$-95% air at 37° C. A drug was subjected to graded dilution in dimethylsulfoxide and further diluted with a DMEM medium containing 10% FCS. Then, the dilution was dispensed to the plate on which cells had been disseminated, at a rate of 100 microliters per well. The plate was incubated for further three days in 5% CO$_2$-95% air at 37° C. Cell growth after incubation was measured by the WST-8 method (H. Tominaga, et al., *Anal. Commun.*, 36, 47-50 (1999)). Here, the WST-8 method refers to a method in which 20 microliters of a WST-8 reagent solution is added to each well, incubation is conducted at 37° C. for 60 minutes, the plate is stirred, and the amount of formazan produced is measured by a colorimetric method to determine the inhibitory rate of the drug. The concentration for 50% growth inhibition (IC$_{50}$, μM) of the compound was determined.

As shown in Table 2, the compound according to the invention exhibited excellent cell growth inhibitory effect against human-derived cancer cells (HeLa S3).

TABLE 2

|  | Cell growth inhibitory effect (HeLaS3) (IC$_{50}$, μM) |
| --- | --- |
| Example 2 | 0.78 |
| Example 9 | 0.22 |
| Example 10 | 0.28 |
| Example 14 | 1.73 |
| Example 17 | 0.10 |
| Example 19 | 1.01 |

Method for Judging the Effect by Combined Use of Drugs in Cells a) Reagent

Fetal calf serum (FCS) was purchased from Moregate Biotech, DMEM medium from Invitrogen Corp., docetaxel (tradename: Taxere) from Sigma-Aldrich, Inc., and WST-8 from Kishida Chemical Co., Ltd.

b) Cells

Human cervical cancer cells (HeLa S3) were obtained from the American Type Culture Collection (ATCC).

c) Method of Judging the Effect

Cells were suspended in a DMEM medium containing 10% FCS, and the cell suspension was dispensed to two 96-well plastic plates at a rate of 750 cells/100 microliters per well. The plates were incubated overnight in 5% CO$_2$-95% air at 37° C. A drug was subjected to graded dilution in dimethylsulfoxide and further diluted with DMSO or with a DMEM medium containing 10% FCS and also containing 0.6 nM docetaxel. Then, the dilutions were each dispensed to one of the plates on which cells had been disseminated, at a rate of 100 microliters per well. The final concentration of docetaxel at this stage was 0.3 nM. Also, the concentrations in the case of sole administration of the compound according to the invention were 0.003, 0.01, 0.03, 0.1, 0.3, 1, 3 and 10 μM. The plates were incubated for further three days in 5% CO$_2$-95% air at 37° C. Cell growth after incubation was measured by the WST-8 method (H. Tominaga, et al., *Anal. Commun.*, 36, 47-50 (1999)). Here, the WST-8 method refers to a method in which 20 microliters of a WST-8 reagent solution is added to each well, incubation is conducted at 37° C. for 60 minutes, the plate is stirred, and the amount of formazan produced is measured by a colorimetric method to determine the inhibitory rate of the drug. The growth inhibitory effects of docetaxel and of the compound according to the invention were determined, with the value obtained in sole treatment of DMSO being defined as 0%.

The compound according to the invention exhibited excellent cell growth inhibitory effect as well as a synergistic action with a taxane-type anti-tumor agent such as docetaxel against human-derived cancer cells (HeLa S3), as shown in Table 3.

TABLE 3

| Example | Cell growth inhibitory effect by sole administration of docetaxel (0.3 nM) (%) | Conc. of the compound of Example (nM) | Cell growth inhibitory effect by sole administration of the compound of Example (%) | Cell growth inhibitory effect by combined administration of docetaxel and the compound of Example (%) |
| --- | --- | --- | --- | --- |
| Example 2 | 49.6 | 300 | 23.9 | 90.2 |
| Example 9 | 51.6 | 30 | 20.3 | 90.9 |
| Example 10 | 51.6 | 30 | 3.3 | 84.8 |
| Example 14 | 49.6 | 300 | 3.3 | 80.7 |
| Example 17 | 51.6 | 10 | 4.2 | 80.8 |
| Example 19 | 49.6 | 100 | 7.6 | 86.0 |

From the above, the compound according to the invention is believed to be useful as an antitumor agent since it exhibits not only excellent cell growth inhibitory action based on Aurora A selective inhibitory activity, but also a synergistic action in combined use with other antitumor agent. Thus, it is believed that a pharmaceutical composition or Aurora A selective inhibitor containing the novel aminopyridine derivative according to the invention or a pharmaceutically acceptable salt or ester thereof, or an antitumor agent containing the compound according to the invention or a pharmaceutically acceptable salt or ester thereof is effective in the treatment of cancer patients.

The above-mentioned pharmaceutical composition and inhibitor, and the above-mentioned antitumor agent may contain a pharmaceutically acceptable carrier or diluent. Here, the "pharmaceutically acceptable carrier or diluent" refers to excipients [e.g., fats, beeswax, semi-solid and liquid polyols, natural or hydrogenated oils, etc.]; water (e.g., distilled water, particularly distilled water for injection, etc.), physiological saline, alcohol (e.g., ethanol), glycerol, polyols, aqueous glucose solution, mannitol, plant oils, etc.); additives [e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant], and the like.

A suitable tumor for which the therapeutic effect of the compound according to the invention is expected may be exemplified by human solid cancer. Examples of human solid cancer include brain cancer, head and neck cancer, esophageal cancer, thyroid cancer, small cell carcinoma, non-small cell carcinoma, breast cancer, stomach cancer, gallbladder and bile duct cancer, liver cancer, pancreas cancer, colon cancer, rectal cancer, ovarian cancer, chorioepithelioma, uterine cancer, cervical cancer, renal pelvic and ureteral cancer, bladder cancer, prostate cancer, penile cancer, testicular cancer, embryonal cancer, Wilms' tumor, skin cancer, malignant melanoma, neuroblastoma, osteosarcoma, Ewing's tumor, soft tissue sarcoma, and the like.

Next, the above-described "pharmaceutically acceptable salt or ester" will be explained below.

When the compound according to the invention is used as an antitumor agent or the like, it may be also used in a form of pharmaceutically acceptable salt. Typical examples of the pharmaceutically acceptable salt include a salt with an alkali metal such as sodium and potassium; a salt with an inorganic acid, such as hydrochloride, sulfate, nitrate, phosphate, carbonate, hydrogen carbonate, and perchlorate; a salt with an organic acid, such as acetate, propionate, lactate, maleate, fumarate, tartrate, malate, citrate, and ascorbate; a salt with sulfonic acid, such as methanesulfonate, isethionate, benzenesulfonate, and toluenesulfonate; a salt with acidic amino acid, such as aspartate and glutamate; and the like. A pharmaceutically acceptable salt of the Compound (I) is preferably a salt with an inorganic acid, such as hydrochloride, sulfate, nitrate, phosphate, carbonate, hydrogen carbonate, and perchlorate; more preferably hydrochloride.

The process for preparation of a pharmaceutically acceptable salt of the compound according to the invention may be carried out by an appropriate combination of those methods that are conventionally used in the field of organic synthetic chemistry. A specific example thereof is a method in which a solution of the compound according to the invention in its free form is subjected to neutralization titration with an alkaline solution or an acidic solution.

Examples of the ester of the compound according to the invention include methyl ester and ethyl ester. Such esters can be prepared by esterification of a free carboxyl group according to a conventional method.

With regard to each preparation of the combined preparation according to the invention, various preparation forms can be selected, and examples thereof include oral preparations such as tablets, capsules, powders, granules or liquids, or sterilized liquid parenteral preparations such as solutions or suspensions, suppositories, ointments and the like.

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

These solid preparations such as tablets, capsules, granules and powders may generally contain, for example, 0.1 to 100% by weight, and preferably 5 to 98% by weight, of the compound of the above Formula (I) as an active ingredient, based on the total weight of the preparation.

Liquid preparations are produced in the forms of suspension, syrup, injection and drip infusion (intravenous fluid) using appropriate additives that are conventionally used in liquid preparations, such as water, alcohol or a plant-derived oil such as soybean oil, peanut oil and sesame oil.

In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, 0.1 to 10% by weight of an active ingredient based on the total weight of the preparation.

Liquid preparations such as suspension or syrup for oral administration may contain, for example, 0.1 to 10% by weight of an active ingredient based on the total weight of the preparation.

Each preparation of the combined preparation according to the invention can be prepared by a person having ordinary skill in the art according to conventional methods or common techniques. For example, a preparation containing another antitumor agent that is used in combination with the compound represented by the above General Formula (I), can be prepared, if the preparation is an oral preparation, for example, by mixing an appropriate amount of the antitumor agent with an appropriate amount of lactose and filling this mixture into hard gelatin capsules which are suitable for oral administration. On the other hand, preparation can be carried out, if the preparation containing the antitumor agent is an injection, for example, by mixing an appropriate amount of the antitumor agent with an appropriate amount of 0.9% physiological saline and filling this mixture in vials for injection.

Also, in the case of a combination preparation containing the compound represented by the above General Formula (I) according to the invention and another antitumor agent, a person having ordinary skill in the art can easily prepare the preparation according to conventional methods or common techniques.

In the process according to the invention, preferred therapeutic unit may vary in accordance with, for example, the administration route of the compound represented by the General Formula (I), the type of the compound represented by the General Formula (I) used, and the dosage form of the compound represented by the General Formula (I) used; the type, administration route and dosage form of the other antitumor agent used in combination; and the type of cells to be treated, the condition of patient, and the like. The optimal treatment under the given conditions can be determined by a person skilled in the art, based on the set conventional therapeutic unit and/or based on the content of the present specification.

In the process according to the invention, the therapeutic unit for the compound represented by the above General Formula (I) may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other antitumor agent used in combination with the compound represented by the General Formula (I) is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 m$^2$; 50 mg in one administration for an area of 1.25 m$^2$ to less than 1.5 m$^2$; 60 mg in one administration for an area of 1.5 m$^2$ or more. This dose is appropriately increased or decreased depending on the condition of the patient.

The therapeutic unit for gemcitabine is, for example, 1 g as gemcitabine/m$^2$ in one administration, which is administered by intravenous drip infusion over a period of 30 minutes, and one administration per week is continued for 3 weeks, followed by withdrawal from medication on the fourth week. This is set as one course of administration, which is repeated. The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/m$^2$ (body surface area) or less, and it may be appropriately increased or decreased within the range.

The therapeutic unit for etoposide is such that, for example, in the case of intravenous injection, 60 to 100 mg/m$^2$ (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/m$^2$ (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/m$^2$ (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/m$^2$ (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/m$^2$ is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/m$^2$ is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/m$^2$ is administered once a day by intravenous drip infusion for 3 or 4 times at an interval of one week, followed by withdrawal from medication for at least two weeks.

The therapeutic unit for topotecan is such that, for example, 1.5 mg/m$^2$ is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 mg. The total dose is 3,000 to 8,000 mg, which may be appropriately increased or decreased. If necessary, it may be injected or infused intramuscularly, intrathoracically or intratumorally. On the other hand, in the case of oral administration, for example, 100 to 200 mg is administered a day.

The therapeutic unit for gefitinib is such that 250 mg is orally administered once a day.

The therapeutic unit for cetuximab is such that, for example, 400 mg/m$^2$ is administered on the first day by intravenous drip infusion, and then 250 mg/m$^2$ is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/m$^2$ of 5-FU and 200 mg/m$^2$ of leucovorin are administered from the first day to the fifth day by intravenous drip infusion, and this course is repeated at an interval of 4 weeks.

The therapeutic unit for sorafenib is such that, for example, 200 mg is orally administered twice a day (400 mg per day) at least 1 hour before or 2 hours after eating.

The therapeutic unit for sunitinib is such that, for example, 50 mg is orally administered once a day for four weeks, followed by 2 weels off

WORKING EXAMPLES

In a thin-layer chromatography of Examples and Referential Examples, Silica gel$_{60}$F$_{254}$ (Merck) was used as a plate and a UV detector was used as a detecting method. As silica gel for the column, Biotage FLASH column (SI, NH) was used. In a reversed phase preparative liquid chromatography, XBridge Prep C18 (Waters) was used as a column and a 0.1% aqueous trifluoroacetic acid solution and a 0.1% solution of trifluoroacetic acid in acetonitrile were used in a mobile phase. MS spectra were measured using Waters micromass ZQ2000 (ESI, ESCi). NMR spectra were measured using a spectrometer in the type of JEOL JNM-AL400 (400 MHz) or Varian MERCURY400 (400 MHz) and all δ values are represented in ppm.

Meanings of abbreviations are as follows.

s: singlet d: doublet dd: double doublet t: triplet q: quartet m: multiplet br: broad J: coupling constant Hz: Hertz DMSO-d$_6$: dimethylsulfoxide-d$_6$ Boc: tert-butoxycarbonyl group SEM: (2-(trimethylsilyl)ethoxy)methyl group Bn: benzyl group Tf: (trifluoromethyl)sulfonyl group Example 1

Synthesis of 1-(3-chloro-2-fluorobenzoyl)-4-((6-(1,3-thiazol-2-ylamino)pyridin-2-yl)methyl)piperidin-4-ol trifluoroacetate

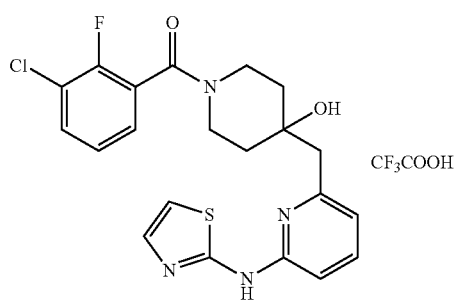 [SMILES: O=C(c1cccc(Cl)c1F)N1CCC(O)(Cc2cccc(Nc3nccs3)n2)CC1 ; "CF3COOH"]

(1) Synthesis of tert-butyl 4-((6-chloropyridin-2-yl)methyl)-4-hydroxypiperidine-1-carboxylate

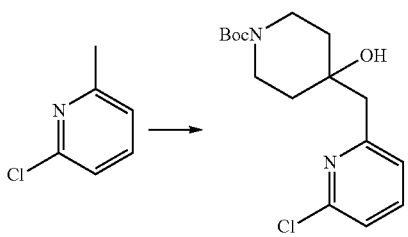

To a solution of 0.22 ml of 2-chloro-6-methylpyridine in 12.5 ml of tetrahydrofuran was added 1.4 ml of a hexane solution containing 1.58 M n-butyl lithium at 0° C., followed by stirring the reaction mixture at 0° C. for 30 minutes. After cooling down to −78° C., a solution of 403.7 mg of tert-butyl 4-oxo-1-piperidinecarboxylate in 1 ml of tetrahydrofuran was added to the solution, followed by gradually warming up the reaction mixture to −40° C. To the reaction mixture was added saturated aqueous ammonium chloride solution, followed by extracting with chloroform. The resulting chloroform layer was washed with brine, dried over anhydrous magnesium sulfate, and filtered. The filtrate was concentrated in vacuo. The resulting residue was purified by a silica gel column chromatography (eluent: hexane/ethyl acetate=20/1–3/2) to give the title compound as a pale yellow oil.

(2) Synthesis of tert-butyl 4-hydroxy-4-((6-(1,3-thiazol-2-ylamino)pyridin-2-yl)methyl)piperidine-1-carboxylate

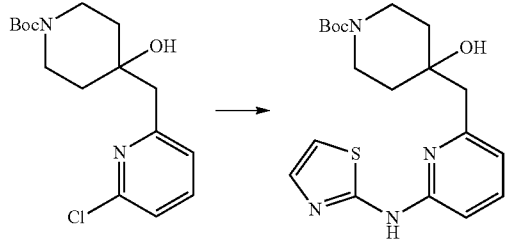 [SMILES: CC(C)(C)OC(=O)N1CCC(O)(Cc2cccc(Cl)n2)CC1 ; CC(C)(C)OC(=O)N1CCC(O)(Cc2cccc(Nc3nccs3)n2)CC1]

A mixture of 50.3 mg of tert-butyl 4((6-chloropyridin-2-yl)methyl)-4-hydroxypiperidine-1-carboxylate, 19.3 mg of 2-aminothiazole, 9.0 mg of 9,9-dimethyl-4,5-bis(diphenylphosphino)xanthene, 4.8 mg of bis(dibenzylideneacetone)palladium(0), 25.2 mg of sodium carbonate and 0.77 ml of toluene was stirred at 100° C. overnight and 120° C. overnight. 156.6 mg of cesium carbonate, 94.4 mg of 9,9-dimethyl-4,5-bis(diphenylphosphino)xanthene and 47.1 mg of bis(dibenzylideneacetone)palladium(0) were added to the reaction mixture, followed by stirring the reaction mixture at 130° C. overnight. The reaction mixture was cooled to room temperature, and diluted with chloroform. An insoluble matter was filtered off using Celite, and the filtrate was concentrated in vacuo. The resulting residue was purified by a preparative thin-layer chromatography (Kieselgel™ 60F$_{254}$, Art5744 (Merck), chloroform/methanol=10/1) to give the title compound as a brown oil.

(3) Synthesis of 4-((6-(1,3-thiazol-2-ylamino)pyridin-2-yl)methyl)piperidine-4-ol

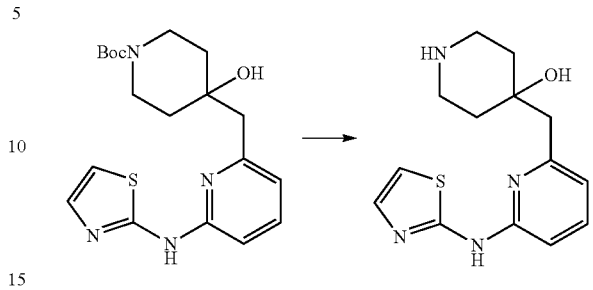

To a solution of 5.9 mg of tert-butyl 4-hydroxy-4-((6-(1,3-thiazol-2-ylamino)pyridin-2-yl)methyl)piperidine-1-carboxylate in 1 ml of chloroform was added 0.5 ml of trifluoroacetic acid at 0° C., followed by stirring the reaction mixture at 0° C. for 2 hours. The reaction mixture was concentrated in vacuo, basified with saturated aqueous sodium bicarbonate solution, and extracted with chloroform. The resulting chloroform layer was dried over anhydrous magnesium sulfate, and filtered. The filtrate was concentrated in vacuo to give the title compound as a brown oil.

(4) Synthesis of 1-(3-chloro-2-fluorobenzoyl)-4-((6-(1,3-thiazol-2-ylamino)pyridin-2-yl)methyl)piperidin-4-ol trifluoroacetate

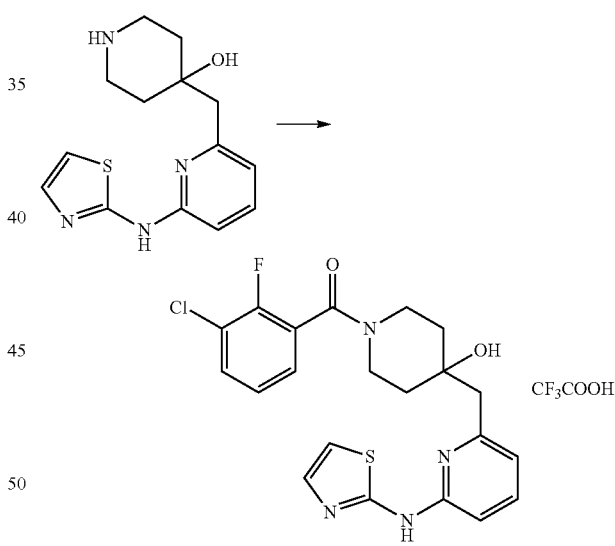

To a solution of 3.9 mg of 4-((6-(1,3-thiazol-2-ylamino)pyridin-2-yl)methyl)piperidine-4-ol in 0.25 ml of dimethylsulfoxide were added 3.4 mg of 3-chloro-2-fluorobenzoic acid, 6.1 mg of hydroxybenzotriazole hydrate and 14.9 mg of 1-(3-dimethylaminopropyl)-3-ethylcarbodiimide hydrochloride at room temperature, followed by stirring the reaction mixture at room temperature for 30 minutes. The reaction mixture was purified by a reversed phase preparative liquid chromatography, followed by concentrating the obtained fraction in vacuo to give the title compound as a white solid.

$^1$H-NMR (CD$_3$OD) δ: 1.53-1.86 (4H, m), 3.07 (2H, s), 7.05-7.13 (21-1 μm), 7.18 (1H, d, J=4.0 Hz), 7.22-7.35 (2H, m), 7.51 (1H, d, J=4.0 Hz), 7.53-7.60 (1H, m), 7.86-7.92 (1H, m).

Mass: 447,449 (M+1)$^+$

Example 2

Synthesis of 1-(3-chloro-2-fluorobenzoyl)-4-((6-(1H-pyrazol-3-ylamino)pyridin-2-yl)methyl)piperidin-4-ol hydrochloride

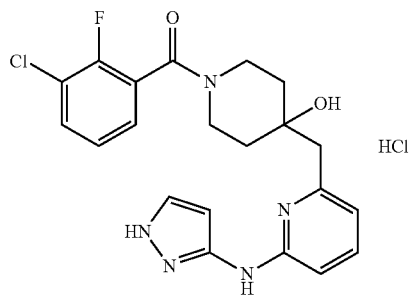 [SMILES: O=C(c1cccc(Cl)c1F)N1CCC(O)(Cc2cccc(Nc3cc[nH]n3)n2)CC1 ; Cl]

(1) Synthesis of 1-benzyl-4-((6-bromopyridin-2-yl)methyl)piperidin-4-ol

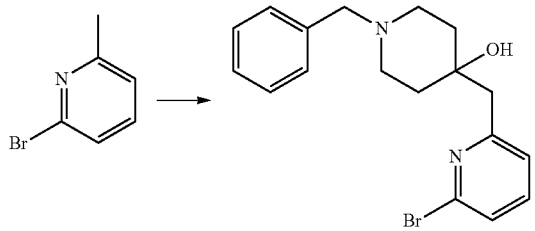

To a solution of 1.11 ml of diisopropylamine in 20 ml of tetrahydrofuran was added 0.73 ml of a hexane solution containing 2.66 M n-butyl lithium at −78° C. The reaction mixture was warmed to 0° C., and then cooled to −78° C. 1.2 ml of 2-bromo-6-methylpyridine was slowly added to the reaction mixture below −70° C., followed by stirring the reaction mixture at −78° C. for 30 minutes. 1.95 g of cerium(III) chloride was added to the reaction mixture at −78° C., followed by stirring the reaction mixture at −78° C. for 1 hour. 0.98 ml of 1-benzyl-4-piperidone was slowly added to the reaction mixture below −70° C., followed by stirring the reaction mixture at −78° C. for 1 h. To the reaction mixture was added saturated aqueous ammonium chloride solution, followed by adding ethyl acetate. An insoluble matter was filtered off using Celite. The organic layer was separated, washed with water and brine, dried over anhydrous magnesium sulfate, and filtered.

The filtrate was concentrated in vacuo. The resulting residue was purified by a silica gel column chromatography (eluent: chloroform to chloroform/methanol=6/1) to give the title compound as a white solid.

(2) Synthesis of 1-benzyl-4-((6-((1-((2-(trimethylsilyl)ethoxy)methyl)-1H-pyrazol-3-yl)amino)pyridin-2-yl)methyl)piperidin-4-ol

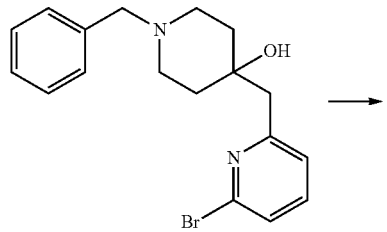

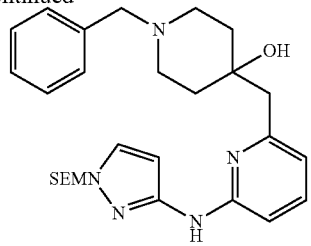

A mixture of 469 mg of 1-benzyl-4-((6-bromopyridin-2-yl)methyl)piperidin-4-ol, 332 mg of 1((2-(trimethylsilyl)ethoxy)methyl)-1H-pyrazol-3-amine (WO2006/046734, page 132, Reference 2), 150 mg of 9,9-dimethyl-4,5-bis(diphenylphosphino)xanthene, 134 mg of tris(dibenzylideneacetone)dipalladium(0)-chloroform complex, 827 mg of potassium phosphate and 10 ml of 1,4-dioxane was stirred at 100° C. overnight, followed by cooling to room temperature. The reaction mixture was diluted with chloroform. An insoluble matter was filtered off using Celite, washed with chloroform, and the filtrate was concentrated in vacuo. The resulting residue was purified by a silica gel column chromatography (eluent: chloroform to chloroform/methanol=10/1) to give the title compound as a pale yellow oil.

(3) Synthesis of 4-((6-((1-((2-(trimethylsilyl)ethoxy)methyl)-1H-pyrazol-3-yl)amino)pyridin-2-yl)methyl)piperidin-4-ol

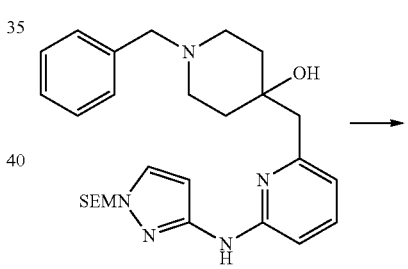

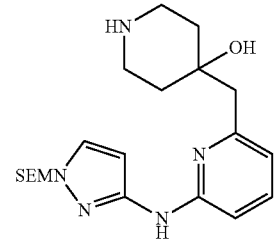

To a solution of 249 mg of 1-benzyl-4-((6-(1-(2-(trimethylsilyl)ethoxy)methyl)-1H-pyrazol-3-yl)amino)pyridin-2-yl)methyl)piperidin-4-ol in 4 ml of tetrahydrofuran and 6 ml of methanol was added 100 mg of 20% palladium hydroxide on carbon, followed by stirring the reaction mixture at room temperature for 4 hours under hydrogen atmosphere. Palladium catalyst was filtered off using Celite, washed with methanol, and the filtrate was concentrated in vacuo to give the title compound as a pale yellow solid.

(4) Synthesis of 1-(3-chloro-2-fluorobenzoyl)-4-((6-((1-((2-(trimethylsilyl)ethoxy)methyl)-1H-pyrazol-3-yl)amino)pyridin-2-yl)methyl)piperidin-4-ol

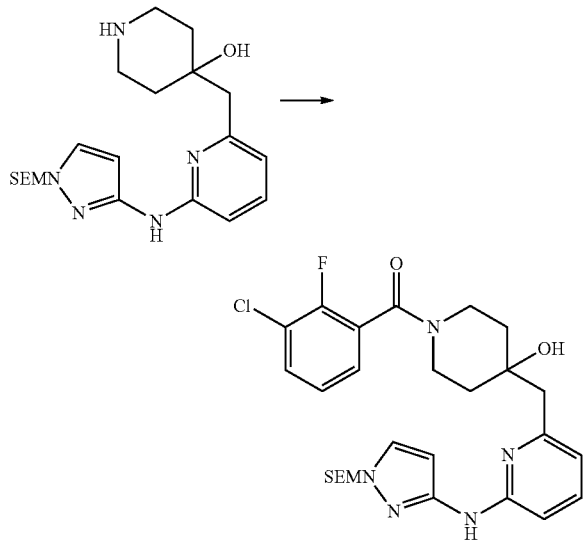

To a solution of 204 mg of 4-((6-((1-((2-(trimethylsilyl)ethoxy)methyl)-1H-pyrazol-3-yl)amino)pyridin-2-yl)methyl)piperidin-4-ol in 10 ml of chloroform were added 132 mg of 3-chloro-2-fluorobenzoic acid, 116 mg of hydroxybenzotriazole hydrate and 194 mg of 1-(3-dimethylaminopropyl)-3-ethylcarbodiimide hydrochloride at room temperature, followed by stirring the reaction mixture at room temperature overnight. The reaction mixture was poured into saturated aqueous sodium bicarbonate solution, and extracted with chloroform. The resulting chloroform layer was dried over anhydrous magnesium sulfate, and filtered. The filtrate was concentrated in vacuo. The resulting residue was purified by a silica gel column chromatography (eluent: hexane/ethyl acetate=10/1 to ethyl acetate) to give the title compound as a colorless oil.

(5) Synthesis of 1-(3-chloro-2-fluorobenzoyl)-4-((6-(1H-pyrazol-3-ylamino)pyridin-2-yl)methyl)piperidin-4-ol hydrochloride

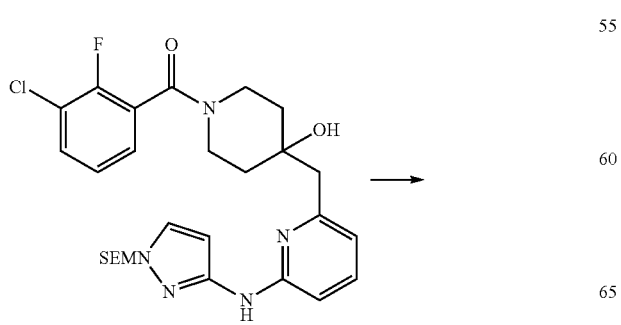

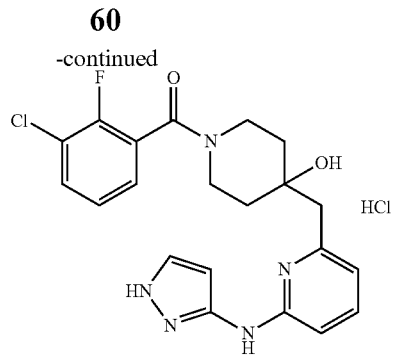

273 mg of 1-(3-chloro-2-fluorobenzoyl)-4-((6-((1-((2-(trimethylsilyl)ethoxy)methyl)-1H-pyrazol-3-yl)amino)pyridin-2-yl)methyl)piperidin-4-ol was dissolved in 3 ml of trifluoroacetic acid and 0.3 ml of water, followed by stirring the reaction mixture at room temperature for 1.5 hours. The reaction mixture was concentrated in vacuo, basified with saturated aqueous sodium bicarbonate solution, and extracted with ethyl acetate. The resulting ethyl acetate layer was dried over anhydrous magnesium sulfate, and filtered. The filtrate was concentrated in vacuo. The resulting residue was purified by a silica gel column chromatography (eluent: chloroform to chloroform/methanol=10/1). The obtained free form was dissolved in 5 ml of ethyl acetate. 0.5 ml of 4 M hydrogen chloride in 1,4-dioxane was added to the solution at room temperature, followed by diluting with 5 ml of tert-butyl methyl ether. The precipitate was collected and washed with tert-butyl methyl ether to give the title compound as a white solid.

$^1$H-NMR (CD$_3$OD) δ: 1.51-1.84 (4H, m), 3.09 (2H, s), 3.25-3.76 (3H, m), 4.30-4.41 (1H, m), 6.13 (1H, s), 6.95-7.04 (1H, m), 7.16 (1H, d, J=8.8 Hz), 7.20-7.42 (2H, m), 7.55-7.63 (1H, m), 7.74 (1H, s), 8.01 (1H, t, J=8.2 Hz).

Mass: 430,432 (M+1)$^+$

Example 3

Synthesis of 2-((1-(3-chloro-2-fluorobenzoyl)piperidin-4-yl)methyl)-6-methyl-N-1H-pyrazol-3-ylpyrimidin-4-amine trifluoroacetate

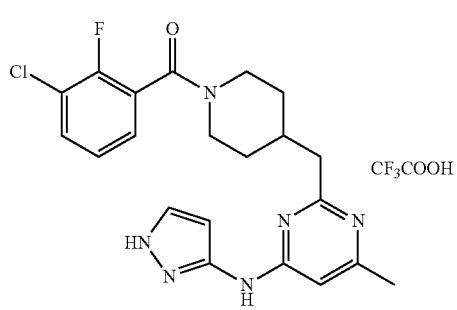 [SMILES: Cc1cc(Nc2cc[nH]n2)nc(CC2CCN(C(=O)c3cccc(Cl)c3F)CC2)n1 ; "CF3COOH"]

(1) Synthesis of 2-chloro-6-methyl-N-(1-((2-(trimethylsilyl)ethoxy)methyl)-1H-pyrazol-3-yl)pyrimidin-4-amine

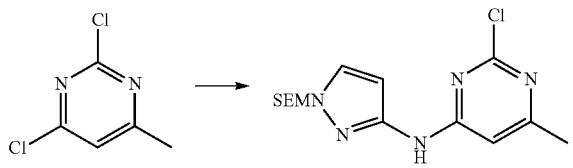

A mixture of 405.9 mg of 2,4-dichloro-6-methylpyrimidine, 585.5 mg of 1-((2-(trimethylsilyl)ethoxy)methyl)-1H-pyrazol-3-amine (WO2006/046734, page 132, Reference 2), 231.9 mg of 9,9-dimethyl-4,5-bis(diphenylphosphino)xanthene, 208.6 mg of tris(dibenzylideneacetone)dipalladium (0)-chloroform complex, 751.2 mg of potassium phosphate and 20 ml of 1,4-dioxane was stirred at 80° C. overnight, followed by cooling to room temperature. The reaction mixture was diluted with ethyl acetate. An insoluble matter was filtered off using Celite, and washed with ethyl acetate. The filtrate was washed with saturated aqueous sodium bicarbonate solution and brine, dried over anhydrous magnesium sulfate, and filtered. The filtrate was concentrated in vacuo. The resulting residue was purified by a silica gel column chromatography (eluent: hexane/ethyl acetate=10/1–2/3) to give the title compound.

(2) Synthesis of tert-butyl 4-((4-methyl-6-((1-((2-(trimethylsilyl)ethoxy)methyl)-1H-pyrazol-3-yl)amino)pyrimidin-2-yl)methyl)piperidine-1-carboxylate

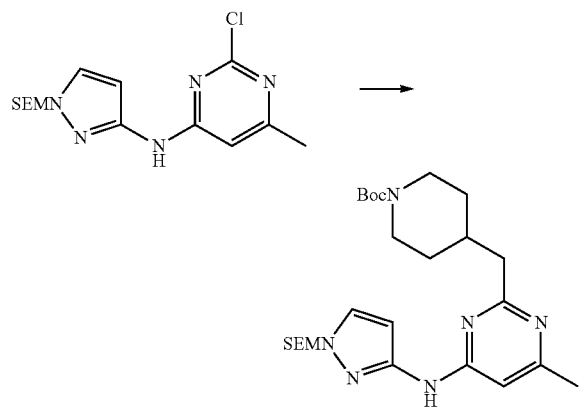

To 116.2 mg of tert-butyl 4-methylenepiperidine-1-carboxylate was added a solution of 71.3 mg of 9-borabicyclo[3.3.1]nonane in 2 ml of tetrahydrofuran at room temperature. The reaction mixture was stirred at 90° C. for 1.5 hours, cooled to room temperature, and added to a suspension of 106.8 mg of 2-chloro-6-methyl-N-(1-((2-(trimethylsilyl)ethoxy)methyl)-1H-pyrazol-3-yl)pyrimidin-4-amine, 12.3 mg of (1,1'-bis(diphenylphosphino)ferrocene)dichloropalladium(II)-dichloromethane complex, 4.3 mg of triphenylarsine and 49.8 mg of potassium carbonate in 2 ml of N,N-dimethylformamide and 0.2 ml of water. The reaction mixture was stirred at 60° C. for 8 hours. 12.4 mg of (1,1'-bis(diphenylphosphino)ferrocene)dichloropalladium(II)-dichloromethane complex, 4.8 mg of triphenylarsine and 47.3 mg of potassium carbonate was added to the reaction mixture, followed by stirring the reaction mixture at 60° C. for 13 hours, 90° C. for 1.5 hours and 100° C. for 2.5 hours. 13.7 mg of (1,1'-bis(diphenylphosphino)ferrocene)dichloropalladium (II)-dichloromethane complex, 5.0 mg of triphenylarsine, 47.1 mg of potassium carbonate and a solution of tert-butyl 4-(9-borabicyclo[3.3.1]non-9-ylmethyl)piperidine-1-carboxylate (prepared from 117.6 mg of tert-butyl 4-methylenepiperidine-1-carboxylate and 145.2 mg of 9-borabicyclo[3.3.1]nonane in 2.5 ml of tetrahydrofuran at 100° C. for 3 hours) were added to the reaction mixture, followed by stirring the reaction mixture at 100° C. for 4.5 hours. The reaction mixture was cooled to room temperature, poured into water, and extracted with ethyl acetate. The organic layer was washed with brine, dried over anhydrous magnesium sulfate, and filtered. The filtrate was concentrated in vacuo. The resulting residue was purified by a silica gel column chromatography (eluent: hexane/ethyl acetate=8/1 to ethyl acetate) to give the title compound.

(3) Synthesis of 6-methyl-2-(piperidin-4-ylmethyl)-N-(1-((2-(trimethylsilyl)ethoxy)methyl)-1H-pyrazol-3-yl)pyrimidin-4-amine

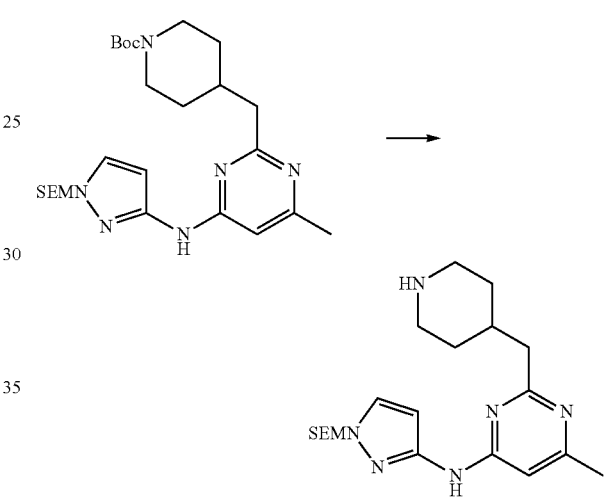

21.2 mg of tert-butyl 4-((4-methyl-6-((1-((2-(trimethylsilyl)ethoxy)methyl)-1H-pyrazol-3-yl)amino)pyrimidin-2-yl)methyl)piperidine-1-carboxylate was dissolved in 1 ml of formic acid at room temperature, followed by stirring the reaction mixture at room temperature for 1 hour. The reaction mixture was concentrated in vacuo, basified with saturated aqueous sodium bicarbonate solution, and extracted with chloroform. The organic layer was washed with brine, dried over anhydrous magnesium sulfate, and filtered. The filtrate was concentrated in vacuo to give the title compound.

(4) Synthesis of 2-((1-(3-chloro-2-fluorobenzoyl)piperidin-4-yl)methyl)-6-methyl-N-(1-((2-(trimethylsilyl)ethoxy)methyl)-1H-pyrazol-3-yl)pyrimidin-4-amine

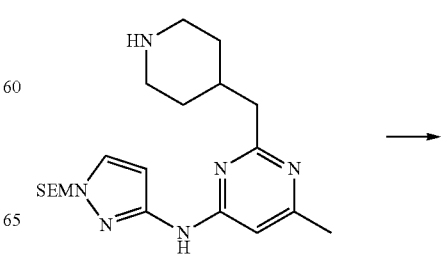

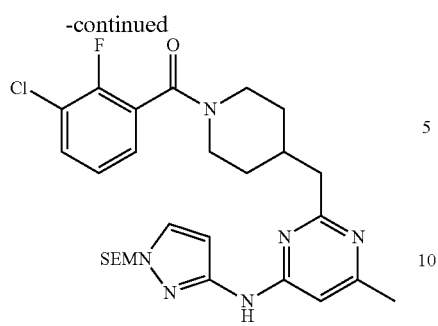

To a solution of 29.8 mg of 6-methyl-2-(piperidin-4-ylmethyl)-N-(1-((2-(trimethylsilyl)ethoxy)methyl)-1H-pyrazol-3-yl)pyrimidin-4-amine in 2 ml of chloroform were added 39.1 mg of 3-chloro-2-fluorobenzoic acid, 0.093 ml of triethylamine, 29.5 mg of hydroxybenzotriazole hydrate and 43.8 mg of 1-(3-dimethylaminopropyl)-3-ethylcarbodiimide hydrochloride at room temperature, followed by stirring the reaction mixture at room temperature for 1.5 hours. The reaction mixture was poured into saturated aqueous sodium bicarbonate solution, and extracted with chloroform. The resulting chloroform layer was dried over anhydrous magnesium sulfate, and filtered. The filtrate was concentrated in vacuo. The resulting residue was purified by a silica gel column chromatography (eluent: hexane/ethyl acetate=1/1 to ethyl acetate) to give the title compound.

(5) Synthesis of 2-((1-(3-chloro-2-fluorobenzoyl)piperidin-4-yl)methyl)-6-methyl-N-1H-pyrazol-3-ylpyrimidin-4-amine trifluoroacetate

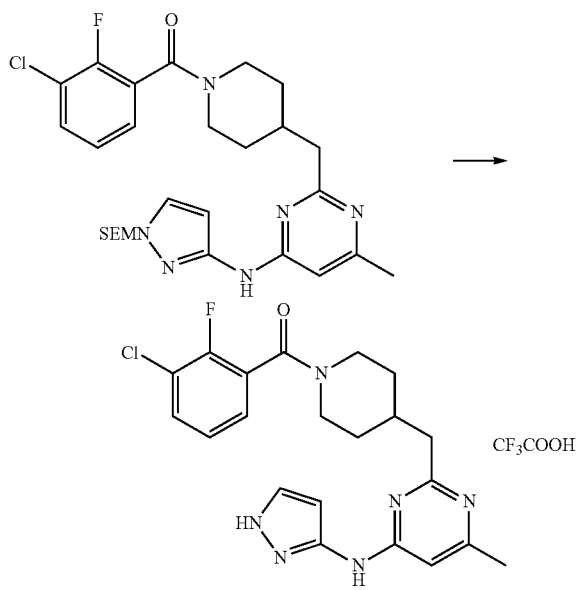

24.9 mg of 2-((1-(3-chloro-2-fluorobenzoyl)piperidin-4-yl)methyl)-6-methyl-N-(1-((2-(trimethylsilyl)ethoxy)methyl)-1H-pyrazol-3-yl)pyrimidin-4-amine was dissolved in 0.9 ml of trifluoroacetic acid and 0.1 ml of water at room temperature, followed by stirring the reaction mixture at 60° C. for 30 minutes. The reaction mixture was cooled to room temperature, and concentrated in vacuo. The reaction mixture was purified by a reversed phase preparative liquid chromatography, followed by concentrating the obtained fraction in vacuo to give the title compound as a white solid.

$^1$H-NMR (CD$_3$OD) δ: 1.25-1.49 (2H, m), 1.76-2.04 (2H, m), 2.30-2.43 (1H, m), 2.53 (3H, s), 2.80-2.99 (3H, m), 3.10-3.28 (1H, m), 3.50-3.61 (1H, m), 4.67-4.76 (1H, m), 5.43-7.80 (6H, m).
Mass: 429,431 (M+1)$^+$ Example 4

Synthesis of ethyl 1-(3-chloro-2-fluorobenzoyl)-4-((6-(1H-pyrazol-3-ylamino)pyridin-2-yl)methyl)piperidine-4-carboxylate

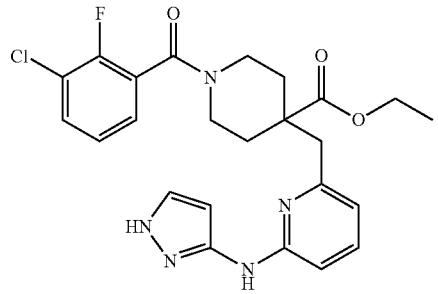 [SMILES: CCOC(=O)C1(Cc2cccc(Nc3cc[nH]n3)n2)CCN(C(=O)c2cccc(Cl)c2F)CC1]

(1) Synthesis of 2-bromo-6-(bromomethyl)pyridine

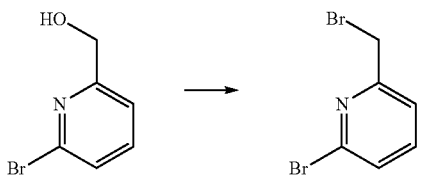 [SMILES: OCc1cccc(Br)n1 ; BrCc1cccc(Br)n1]

To a solution of 498 mg of (6-bromo-pyridin-2-yl)methanol in 6 ml of N,N-dimethylformamide were successively added 1.15 ml of N,N-diisopropylethylamine and a solution of 695 mg of methanesulfonic anhydride in 2 ml of N,N-dimethylformamide under cooling with ice, followed by stirring the reaction mixture at room temperature for 20 minutes. Then 693 mg of lithium bromide was added to the solution, followed by stirring the reaction mixture at room temperature for 1 hour. After adding saturated aqueous sodium bicarbonate solution to the reaction mixture, the mixture was extracted with ethyl acetate. The resulting ethyl acetate solution was dried over anhydrous magnesium sulfate and filtered. The filtrate was concentrated in vacuo. The resulting residue was purified by a silica gel column chromatography (eluent: hexane/ethyl acetate=20/1–3/2) to give the title compound as a pale yellow solid.

(2) Synthesis of 1-tert-butyl 4-ethyl 4-((6-bromopyridin-2-yl)methyl)piperidine-1,4-dicarboxylate

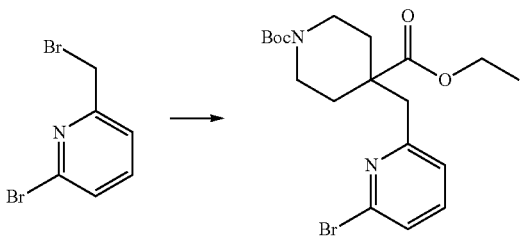 [SMILES: BrCc1cccc(Br)n1 ; CCOC(=O)C1(Cc2cccc(Br)n2)CCN(C(=O)OC(C)(C)C)CC1]

To a solution of 0.855 ml of diisopropylamine in 15 ml of tetrahydrofuran was added 2.26 ml of a hexane solution containing 2.66 M n-butyllithium at 0° C., followed by stirring the reaction mixture at 0° C. for 30 minutes. After cooling down to −78° C., a solution of 1.54 g of 1-tert-butyl 4-ethyl piperidine-1,4-dicarboxylate in 5 ml of tetrahydrofuran was added to the reaction mixture, and the resultant mixture was stirred at −78° C. for 30 minutes. A solution of 1.00 g of 2-bromo-6-(bromomethyl)pyridine in 5 ml of tetrahydrofuran was added to the reaction mixture, followed by stirring the reaction mixture at −78° C. for 2 hours. To the reaction mixture was added saturated aqueous ammonium chloride solution, followed by extracting with ethyl acetate. The resulting ethyl acetate solution was dried over anhydrous magnesium sulfate, and filtered. The filtrate was concentrated in vacuo. The resulting residue was purified by a silica gel column chromatography (eluent: hexane/ethyl acetate=20/1–2/1) to give the title compound as a yellow oil.

(3) Synthesis of 1-tert-butyl 4-ethyl 4-((6-((1-tert-butyl-1H-pyrazol-5-yl)amino)pyridin-2-yl)methyl)piperidine-1,4-dicarboxylate

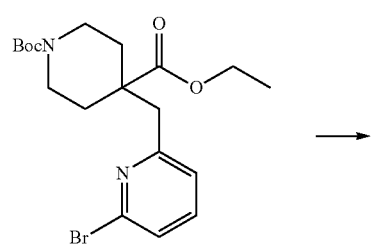

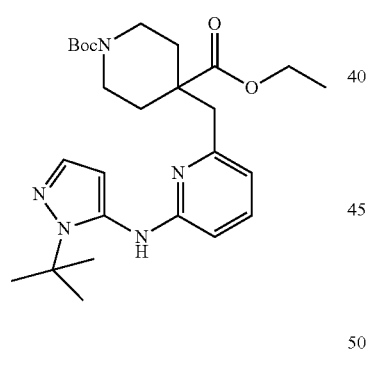

A mixture of 1.33 g of 1-tert-butyl 4-ethyl 4-((6-bromopyridin-2-yl)methyl)piperidine-1,4-dicarboxylate, 650 mg of 1-tert-butyl-1H-pyrazol-5-amine (WO2007/126126, page 72, Reference 1), 360 mg of 9,9-dimethyl-4,5-bis(diphenylphosphino)xanthene, 322 mg of tris(dibenzylideneacetone)dipalladium(0)-chloroform complex, 1.98 g of potassium phosphate and 30 ml of 1,4-dioxane was stirred at 100° C. for 4 hours, followed by cooling down to room temperature. An insoluble matter was filtered off using Celite and washed with ethyl acetate. The resulting ethyl acetate solution was concentrated in vacuo. The resulting residue was purified by a silica gel column chromatography (eluent: hexane/ethyl acetate=20/1–3/2) to give the title compound as a pale brown oil.

(4) Synthesis of ethyl 4-((6-((1-tert-butyl-1H-pyrazol-5-yl)amino)pyridin-2-yl)methyl)piperidine-4-carboxylate

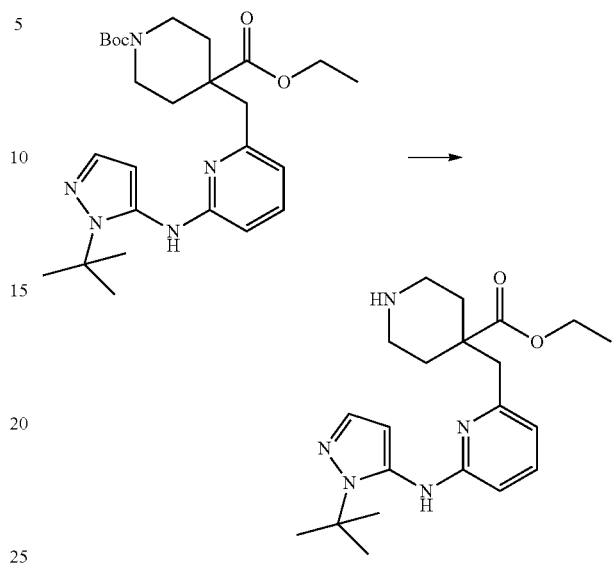

To 1.21 g of 1-tert-butyl 4-ethyl 4-((6-((1-tert-butyl-1H-pyrazol-5-yl)amino)pyridin-2-yl)methyl)piperidine-1,4-dicarboxylate were added 12 ml of 4 M hydrogen chloride in 1,4-dioxane and 3 ml of ethanol at room temperature. The reaction mixture was stirred at room temperature for 30 minutes, and concentrated in vacuo. The resulting residue was basified with saturated aqueous sodium bicarbonate solution, and extracted with ethyl acetate. The resulting ethyl acetate solution was dried over anhydrous magnesium sulfate, and filtered. The filtrate was concentrated in vacuo to give the title compound as a pale brown oil.

(5) Synthesis of ethyl 4-((6-((1-tert-butyl-1H-pyrazol-5-yl)amino)pyridin-2-yl)methyl)-1-(3-chloro-2-fluorobenzoyl)piperidine-4-carboxylate

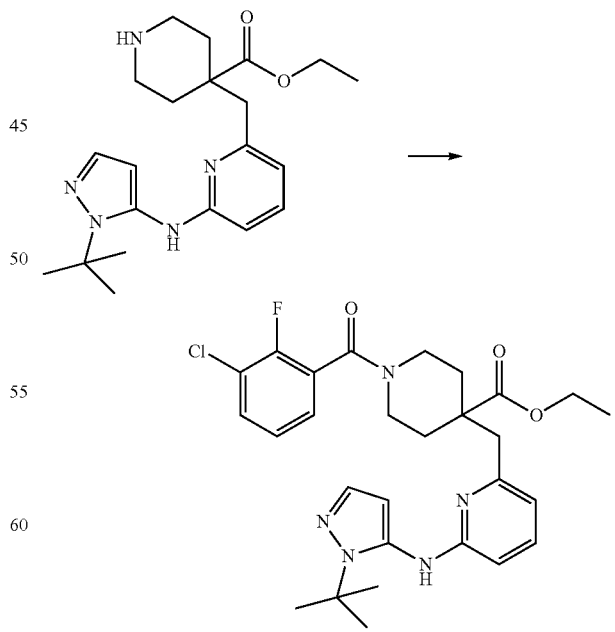

To a solution of 230 mg of ethyl 4-((6-((1-tert-butyl-1H-pyrazol-5-yl)amino)pyridin-2-yl)methyl)piperidine-4-carboxylate in 10 ml of chloroform were added 156 mg of 3-chloro-2-fluorobenzoic acid, 137 mg of hydroxybenzotriazole hydrate and 229 mg of 1-(3-dimethylaminopropyl)-3-ethylcarbodiimide hydrochloride at room temperature, followed by stirring the reaction mixture at room temperature overnight. The reaction mixture was poured into saturated aqueous sodium bicarbonate solution, and extracted with ethyl acetate. The resulting ethyl acetate layer was dried over anhydrous magnesium sulfate, and filtered. The filtrate was concentrated in vacuo. The resulting residue was purified by a silica gel column chromatography (eluent: chloroform to chloroform/methanol=20/1) to give the title compound as a pale yellow oil.

(6) Synthesis of ethyl 1-(3-chloro-2-fluorobenzoyl)-4-((6-(1H-pyrazol-3-ylamino)pyridin-2-yl)methyl)piperidine-4-carboxylate

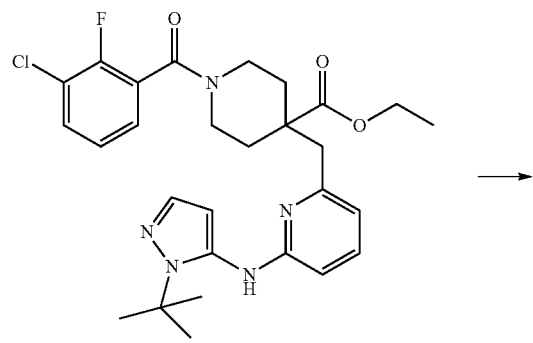

207 mg of ethyl 4-((6-((1-tert-butyl-1H-pyrazol-5-yl)amino)pyridin-2-yl)methyl)-1-(3-chloro-2-fluorobenzoyl)piperidine-4-carboxylate was dissolved in 3 ml of formic acid at room temperature, followed by stirring the reaction mixture at 100° C. for 8 hours. The reaction mixture was cooled to room temperature, and concentrated in vacuo. The resulting residue was basified with saturated aqueous sodium bicarbonate solution, and extracted with ethyl acetate. The resulting ethyl acetate solution was dried over anhydrous magnesium sulfate, and filtered. The filtrate was concentrated in vacuo. The resulting residue was purified by a silica gel column chromatography (eluent: chloroform to chloroform/methanol=10/1) to give the title compound as a colorless oil.

$^1$H-NMR (CDCl$_3$) δ: 1.17 (3H, t, J=7.0 Hz), 1.40-1.75 (2H, m), 2.17 (1H, d, J=12.4 Hz), 2.31 (1H, d, J=12.4 Hz), 2.90-3.30 (4H, m), 3.43 (1H, d, J=13.6 Hz), 4.14 (2H, q, J=7.0 Hz), 4.53 (1H, d, J=13.6 Hz), 6.04 (1H, s), 6.54 (1H, d, J=6.7 Hz), 6.83 (1H, d, J=7.8 Hz), 7.10-7.31 (3H, m), 7.40-7.48 (3H, m).

Mass: 486,488 (M+1)$^+$

Example 5

Synthesis of ethyl 1-(2-fluoro-3-(trifluoromethyl)benzoyl)-4-((6-(1H-pyrazol-3-ylamino)pyridin-2-yl)methyl)piperidine-4-carboxylate

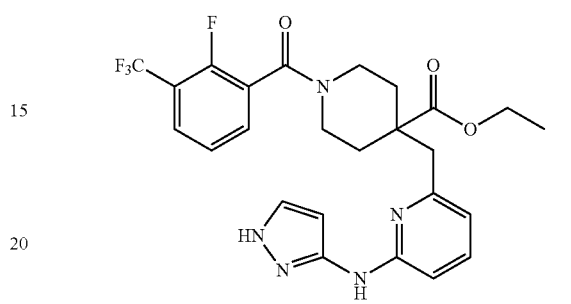

(1) Synthesis of ethyl 4-((6-((1-tert-butyl-1H-pyrazol-5-yl)amino)pyridin-2-yl)methyl)-1-(2-fluoro-3-(trifluoromethyl)benzoyl)piperidine-4-carboxylate

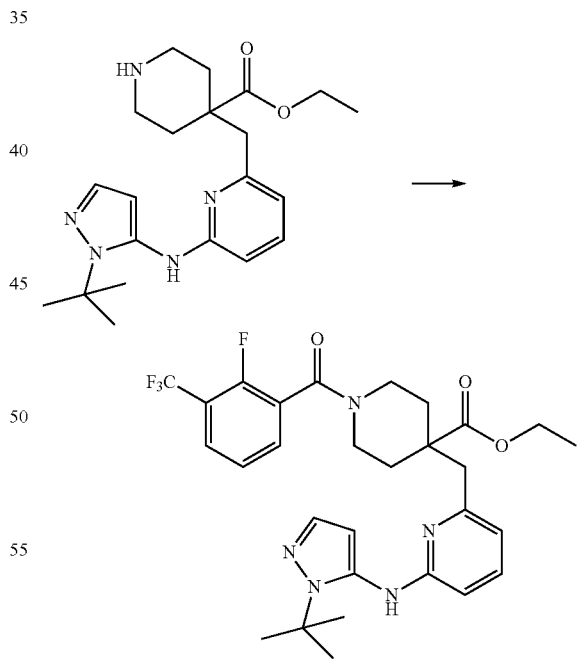

The title compound was obtained as a pale yellow oil in the same manner as in the step of Example 4(5) using 2-fluoro-3-(trifluoromethyl)benzoic acid, instead of 3-chloro-2-fluorobenzoic acid as used in the step of Example 4(5).

(2) Synthesis of ethyl 1-(2-fluoro-3-(trifluoromethyl)benzoyl)-4-((6-(1H-pyrazol-3-ylamino)pyridin-2-yl)methyl)piperidine-4-carboxylate (1) Synthesis of 1-(3-chloro-2-fluorobenzoyl)-4-((6-(1H-pyrazol-3-ylamino)pyridin-2-yl)methyl)piperidine-4-carboxylic acid

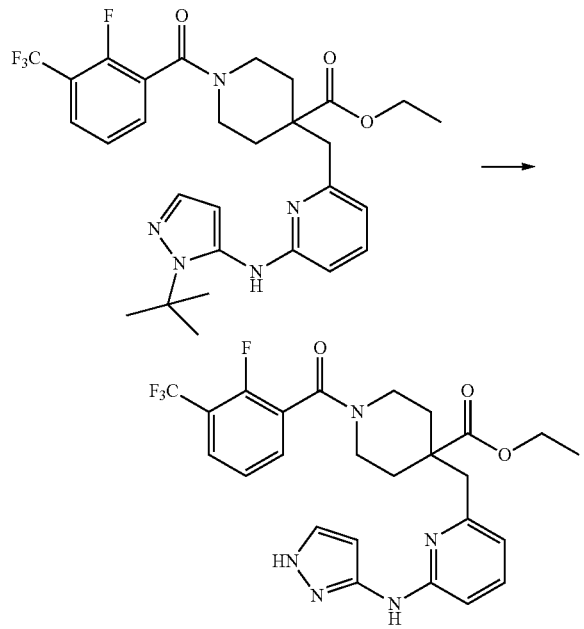
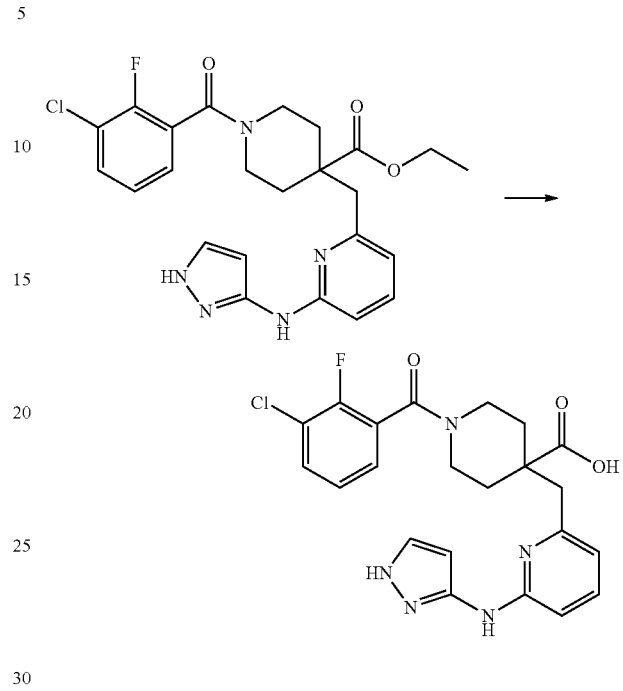

The title compound was obtained as a pale yellow oil in the same manner as in the step of Example 4(6) using ethyl 4-((6-((1-tert-butyl-1H-pyrazol-5-yl)amino)pyridin-2-yl)methyl)-1-(2-fluoro-3-(trifluoromethyl)benzoyl)piperidine-4-carboxylate, instead of ethyl 4-((6-((1-tert-butyl-1H-pyrazol-5-yl)amino)pyridin-2-yl)methyl)-1-(3-chloro-2-fluorobenzoyl)piperidine-4-carboxylate as used in the step of Example 4(6).

$^1$H-NMR (CDCl$_3$) δ: 1.17 (3H, t, J=7.0 Hz), 1.40-1.75 (2H, m), 2.19 (1H, d, J=12.4 Hz), 2.31 (1H, d, J=12.4 Hz), 2.90-3.30 (4H, m), 3.41 (1H, d, J=13.6 Hz), 4.14 (2H, q, J=7.0 Hz), 4.54 (1H, d, J=13.6 Hz), 6.05 (1H, s), 6.54 (1H, d, J=7.0 Hz), 6.82 (1H, d, J=8.0 Hz), 7.02-7.25 (1H, m), 7.31 (1H, t, J=7.8 Hz), 7.42-7.47 (2H, m), 7.57 (1H, brs), 7.65 (1H, t, J=7.0 Hz). Mass: 520 (M+1)$^+$ Example 6

Synthesis of 1-(3-chloro-2-fluorobenzoyl)-4-((6-(1H-pyrazol-3-ylamino)pyridin-2-yl)methyl)piperidine-4-carboxamide To a solution of 160 mg of ethyl 1-(3-chloro-2-fluorobenzoyl)-4-((6-(1H-pyrazol-3-ylamino)pyridin-2-yl)methyl)piperidine-4-carboxylate as obtained in Example 4 in 4 ml of methanol and 2 ml of tetrahydrofuran was added 1 ml of 1 M aqueous sodium hydroxide solution at room temperature. After stirring at room temperature for 1 hour, 2 ml of 5 M aqueous sodium hydroxide solution was added to the reaction mixture at room temperature, followed by stirring the reaction mixture at 60° C. for 3 days. The reaction mixture was cooled to room temperature, followed by concentrating in vacuo. The resulting residue was neutralized with 2 M hydrochloric acid, and extracted with chloroform. The resulting chloroform solution was dried over anhydrous magnesium sulfate, and filtered. The filtrate was concentrated in vacuo to give the title compound as a pale yellow solid.

(2) Synthesis of 1-(3-chloro-2-fluorobenzoyl)-4-((6-(1H-pyrazol-3-ylamino)pyridin-2-yl)methyl)piperidine-4-carboxamide

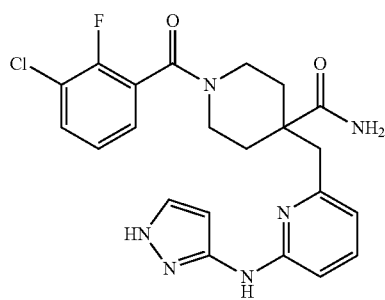 [SMILES: NC(=O)C1(Cc2cccc(Nc3cc[nH]n3)n2)CCN(C(=O)c2cccc(Cl)c2F)CC1]
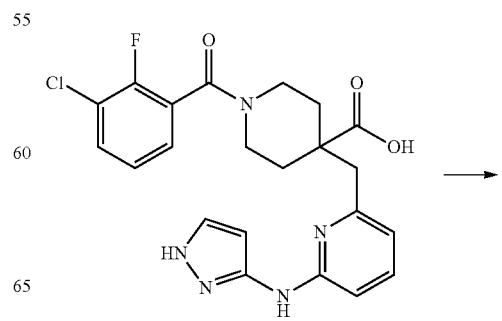

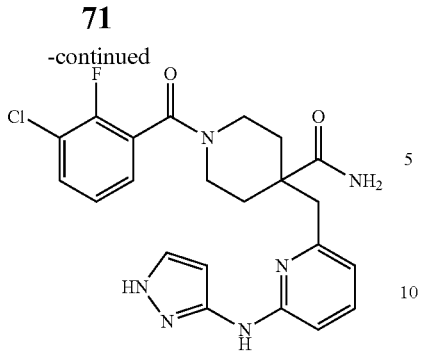

To a solution of 82.8 mg of 1-(3-chloro-2-fluorobenzoyl)-4-((6-(1H-pyrazol-3-ylamino)pyridin-2-yl)methyl)piperidine-4-carboxylic acid in 5 ml of chloroform were added 97 mg of ammonium chloride, 0.252 ml of triethylamine, 83 mg of hydroxybenzotriazole hydrate and 104 mg of 1-(3-dimethylaminopropyl)-3-ethylcarbodiimide hydrochloride at room temperature, followed by stirring the reaction mixture at room temperature overnight. The reaction mixture was poured into saturated aqueous sodium bicarbonate solution, and extracted with ethyl acetate. The resulting ethyl acetate layer was dried over anhydrous magnesium sulfate, and filtered. The filtrate was concentrated in vacuo. The resulting residue was purified by a preparative thin-layer chromatography (Kieselgel™ 60F$_{254}$, Art5744 (Merck), chloroform/methanol=6/1) to give the title compound as a pale yellow solid.

$^1$H-NMR (CD$_3$OD) δ: 1.55-1.76 (2H, m), 1.98-2.10 (1H, m), 2.15-2.26 (1H, m), 2.94-3.04 (2H, m), 3.20-3.50 (3H, m), 4.26-4.37 (1H, m), 6.01 (1H, brs), 6.62-6.78 (2H, m), 7.24-7.62 (5H, m).
Mass: 457,459 (M+1)$^+$ Example 7

Synthesis of 1-(2-fluoro-3-(trifluoromethyl)benzoyl)-4-((6-(1H-pyrazol-3-ylamino)pyridin-2-yl)methyl)piperidine-4-carboxamide

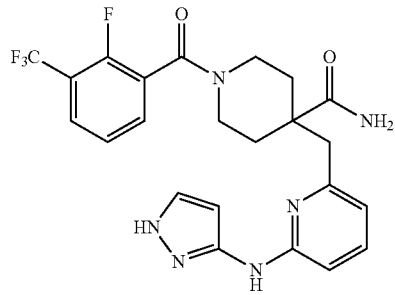 [SMILES: NC(=O)C1(Cc2cccc(Nc3cc[nH]n3)n2)CCN(C(=O)c2cccc(C(F)(F)F)c2F)CC1]

(1) Synthesis of 1-(2-fluoro-3-(trifluoromethyl)benzoyl)-4-((6-(1H-pyrazol-3-ylamino)pyridin-2-yl)methyl)piperidine-4-carboxylic acid

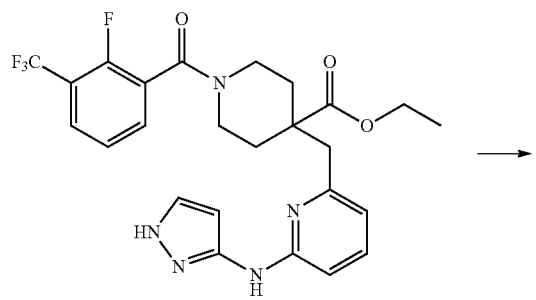

The title compound was obtained as a pale yellow solid in the same manner as in the step of Example 6(1) using ethyl 1-(2-fluoro-3-(trifluoromethyl)benzoyl)-4-((6-(1H-pyrazol-3-ylamino)pyridin-2-yl)methyl)piperidine-4-carboxylate as obtained in Example 5, instead of ethyl 1-(3-chloro-2-fluorobenzoyl)-4-((6-(1H-pyrazol-3-ylamino)pyridin-2-yl)methyl)piperidine-4-carboxylate as used in the step of Example 6(1).

(2) Synthesis of 1-(2-fluoro-3-(trifluoromethyl)benzoyl)-4-((6-(1H-pyrazol-3-ylamino)pyridin-2-yl)methyl)piperidine-4-carboxamide

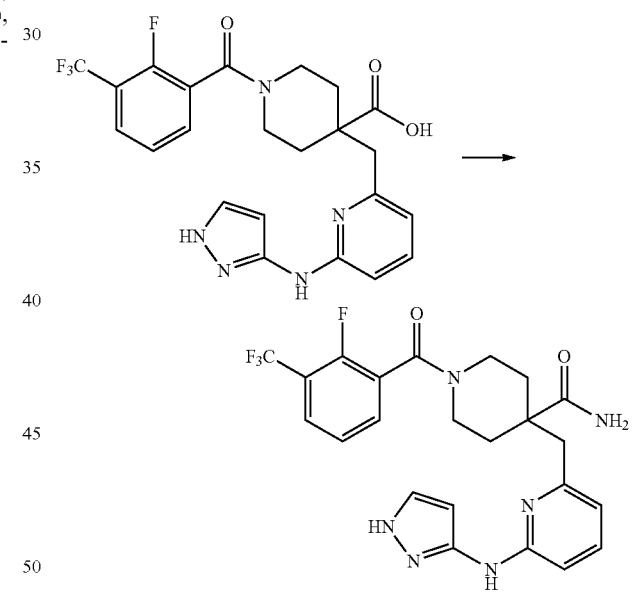

The title compound was obtained as a pale yellow solid in the same manner as in the step of Example 6(2) using 1-(2-fluoro-3-(trifluoromethyl)benzoyl)-4-((6-(1H-pyrazol-3-ylamino)pyridin-2-yl)methyl)piperidine-4-carboxylic acid, instead of 1-(3-chloro-2-fluorobenzoyl)-4-((6-(1H-pyrazol-3-ylamino)pyridin-2-yl)methyl)piperidine-4-carboxylic acid as used in the step of Example 6(2).

$^1$H-NMR (CDCl$_3$) δ: 1.30-1.64 (2H, m), 1.99-2.13 (2H, m), 2.76-2.94 (2H, m), 3.15-3.40 (3H, m), 4.25-4.34 (1H, m), 5.97 (1H, s), 6.51 (1H, d, J=6.6 Hz), 6.59 (1H, brs), 6.66 (1H, d, J=8.0 Hz), 6.86 (1H, brs), 7.26-7.38 (2H, m), 7.42 (1H, d, J=2.0 Hz), 7.54 (1H, brs), 7.65 (1H$_2$O=7.0 Hz), 8.07 (1H, brs).
Mass: 491 (M+1)$^+$

Example 8

Synthesis of 1-(2-fluoro-3-(trifluoromethyl)benzoyl)-N-methoxy-4-((6-(1H-pyrazol-3-ylamino)pyridin-2-yl)methyl)piperidine-4-carboxamide

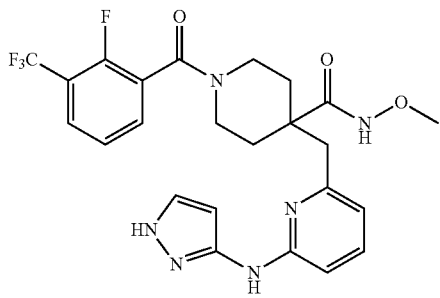 [SMILES: CONC(=O)C1(Cc2cccc(Nc3cc[nH]n3)n2)CCN(C(=O)c2cccc(C(F)(F)F)c2F)CC1]

The title compound was obtained as a pale yellow solid in the same manner as in the step of Example 7(2) using O-methylhydroxylamine hydrochloride, instead of ammonium chloride as used in the step of Example 7(2).

$^1$H-NMR (CDCl$_3$) δ: 1.35-1.70 (2H, m), 2.15-2.29 (2H, m), 2.90-3.01 (2H, m), 3.30-3.51 (3H, m), 3.63 (3H, s), 4.11-4.25 (1H, m), 6.08 (1H, s), 6.51-6.60 (1H, m), 6.84 (1H, d, J=8.0 Hz), 7.30 (1H, t, J=7.8 Hz), 7.41 (1H, t, J=7.8 Hz), 7.47 (1H, d, J=2.0 Hz), 7.51-7.79 (3H, m).

Mass: 521 (M+1)$^+$

Example 9

Synthesis of 5-(1-(2-fluoro-3-(trifluoromethyl)benzoyl)-4-((6-(1H-pyrazol-3-ylamino)pyridin-2-yl)methyl)piperidin-4-yl)-1,3,4-oxadiazol-2(3H)-one

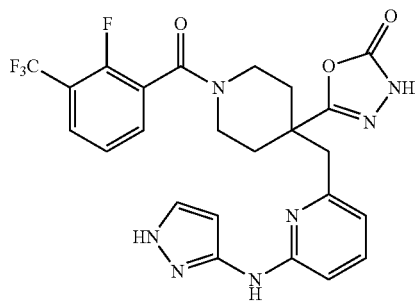 [SMILES: O=C(c1cccc(C(F)(F)F)c1F)N1CCC(Cc2cccc(Nc3cc[nH]n3)n2)(c2n[nH]c(=O)o2)CC1]

(1) Synthesis of 4-((6-((1-tert-butyl-1H-pyrazol-5-yl)amino)pyridin-2-yl)methyl)-1-(2-fluoro-3-(trifluoromethyl)benzoyl)piperidine-4-carboxylic acid

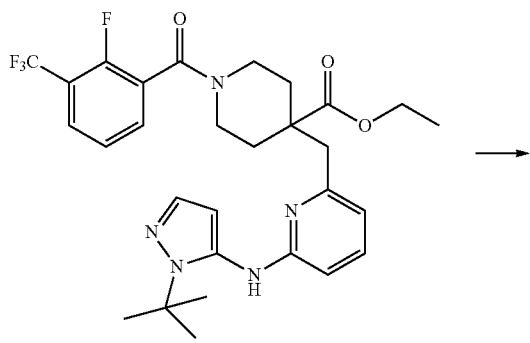

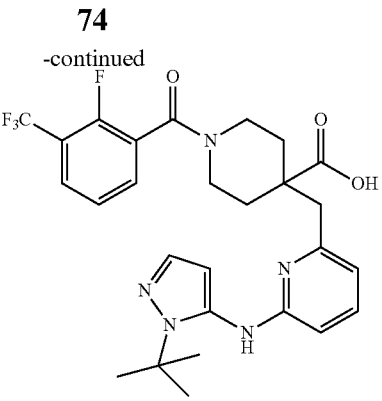

To a solution of 505 mg of ethyl 4-((6-(((1-tert-butyl-1H-pyrazol-5-yl)amino)pyridin-2-yl)methyl)-1-(2-fluoro-3-(trifluoromethyl)benzoyl)piperidine-4-carboxylate obtained in the step of Example 5(1) in 5 ml of ethanol was added 4 ml of 5 M aqueous sodium hydroxide solution at room temperature, followed by stirring the reaction mixture at 60° C. for 3 hours. The reaction mixture was cooled to room temperature, and concentrated in vacuo. The resulting residue was acidified with 2 M hydrochloric acid. The precipitate was collected, and washed with water to give the title compound as a pale yellow solid.

(2) Synthesis of tert-butyl 2-((4-((6-(((1-tert-butyl-1H-pyrazol-5-yl)amino)pyridin-2-yl)methyl)-1-(2-fluoro-3-(trifluoromethyl)benzoyl)piperidin-4-yl)carbonyl)hydrazinecarboxylate

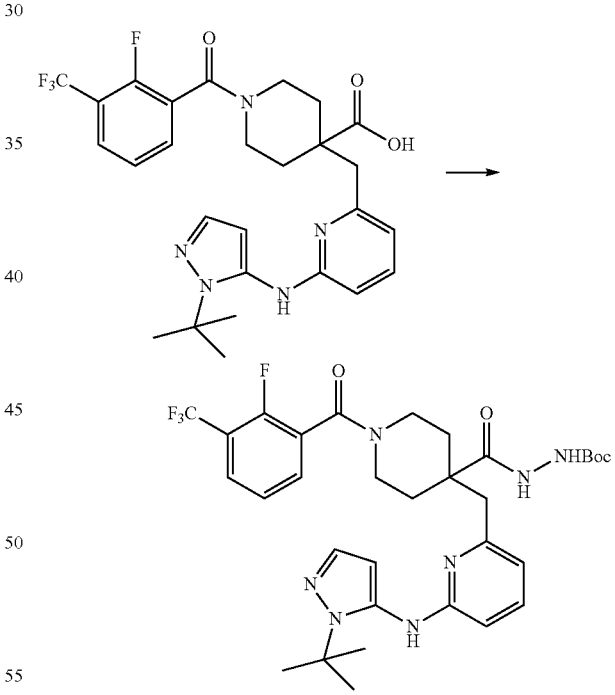

To a solution of 150 mg of 4-((6-((1-tert-butyl-1H-pyrazol-5-yl)amino)pyridin-2-yl)methyl)-1-(2-fluoro-3-(trifluoromethyl)benzoyl)piperidine-4-carboxylic acid in 5 ml of chloroform were added 43.3 mg of tert-butyl carbazate and 63.0 mg of 1-(3-dimethylaminopropyl)-3-ethylcarbodiimide hydrochloride at room temperature, followed by stirring the reaction mixture at room temperature for 6 hours. The reaction mixture was poured into saturated aqueous sodium bicarbonate solution, and extracted with ethyl acetate. The ethyl acetate solution was dried over magnesium sulfate, and filtered. The filtrate was concentrated in vacuo. The resulting residue was purified by a silica gel column chromatography (eluent: hexane/ethyl acetate=10/1 to ethyl acetate) to give the title compound as a white solid.

(3) Synthesis of 4-(((6-(((1-tert-butyl-1H-pyrazol-5-yl)amino)pyridin-2-yl)methyl)-1-(2-fluoro-3-(trifluoromethyl)benzoyl)piperidine-4-carbohydrazide

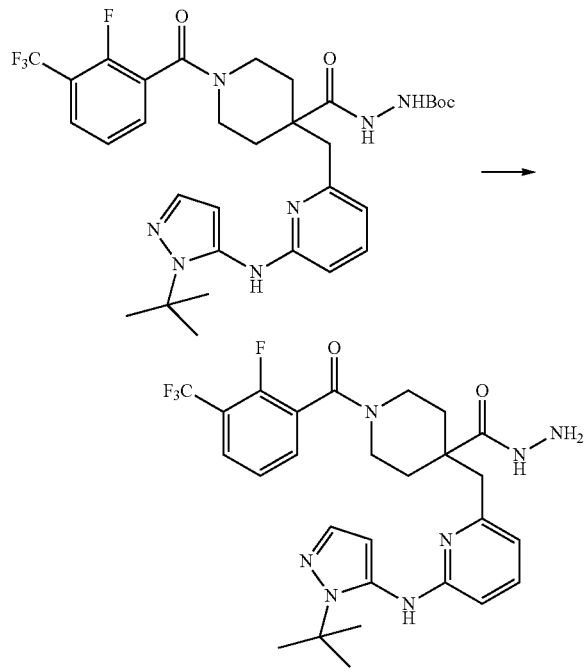

To a solution of 195 mg of tert-butyl 2-((4-(((6-(((1-tert-butyl-1H-pyrazol-5-yl)amino)pyridin-2-yl)methyl)-1-(2-fluoro-3-(trifluoromethyl)benzoyl)piperidin-4-yl)carbonyl)hydrazinecarboxylate in 4 ml of chloroform was added 2 ml of trifluoroacetic acid at 0° C. The reaction mixture was stirred at 0° C. for 2 hours and at room temperature for 2 hours, followed by concentrating in vacuo. The resulting residue was basified with saturated aqueous sodium bicarbonate solution, and extracted with ethyl acetate. The ethyl acetate solution was dried over anhydrous magnesium sulfate, and filtered. The filtrate was concentrated in vacuo. The resulting residue was purified by a silica gel column chromatography (eluent: chloroform to chloroform/methanol=10/1) to give the title compound as a colorless oil.

(4) Synthesis of 5-(4-(((6-(((1-tert-butyl-1H-pyrazol-5-yl)amino)pyridin-2-yl)methyl)-1-(2-fluoro-3-(trifluoromethyl)benzoyl)piperidin-4-yl)-1,3,4-oxadiazol-2(3H)-one

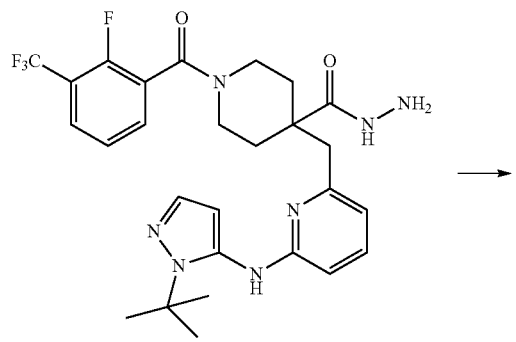

-continued

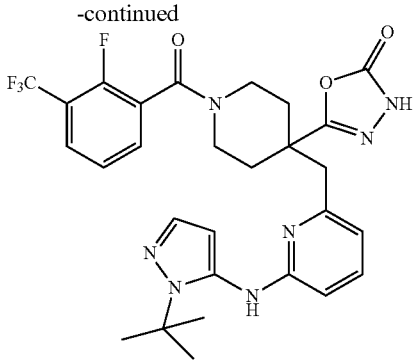

To a solution of 68.5 mg of 4-(((6-(((1-tert-butyl-1H-pyrazol-5-yl)amino)pyridin-2-yl)methyl)-1-(2-fluoro-3-(trifluoromethyl)benzoyl)piperidine-4-carbohydrazide in 5 ml of tetrahydrofuran was added 23.7 mg of 1,1'-carbonyldiimidazole at room temperature. The reaction mixture was stirred at room temperature overnight, and concentrated in vacuo. The resulting residue was purified by a silica gel column chromatography (eluent: hexane/ethyl acetate=20/1 to ethyl acetate) to give the title compound as a colorless oil.

(5) Synthesis of 5-(1-(2-fluoro-3-(trifluoromethyl)benzoyl)-4-(((6-(1H-pyrazol-3-ylamino)pyridin-2-yl)methyl)piperidin-4-yl)-1,3,4-oxadiazol-2(3H)-one

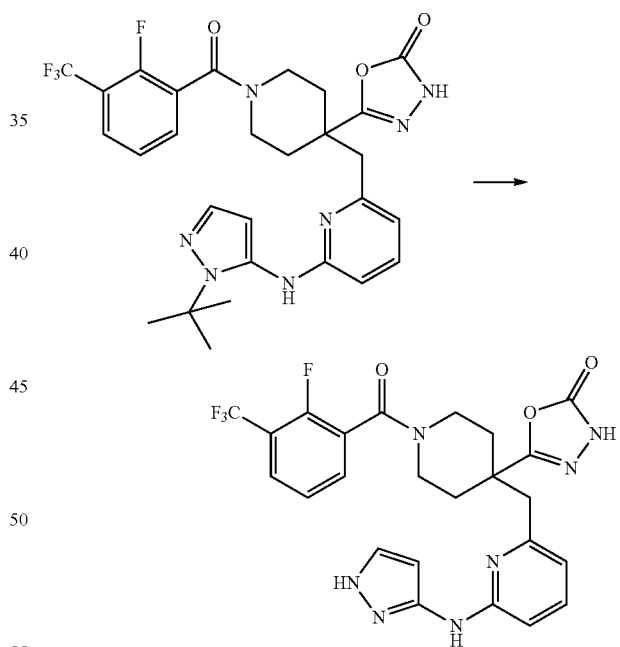

71 mg of 5-(4-(((6-(((1-tert-butyl-1H-pyrazol-5-yl)amino)pyridin-2-yl)methyl)-1-(2-fluoro-3-(trifluoromethyl)benzoyl)piperidin-4-yl)-1,3,4-oxadiazol-2(3H)-one was dissolved in 1.5 ml of formic acid at room temperature, followed by stirring the reaction mixture at 90° C. overnight. The reaction mixture was cooled to room temperature, and concentrated in vacuo. The resulting residue was basified with saturated aqueous sodium bicarbonate solution, and extracted with ethyl acetate. The ethyl acetate solution was dried over anhydrous magnesium sulfate, and filtered. The filtrate was concentrated in vacuo. The resulting residue was purified by a preparative thin-layer chromatography (Kieselgel™ 60F$_{254}$, Art5744 (Merck), chloroform/methanol=10/1) to give the title compound as a pale yellow solid.

$^1$H-NMR (CD$_3$OD) δ: 1.60-2.30 (4H, m), 2.97-3.65 (5H, m), 4.05-4.50 (1H, m), 6.20-7.02 (3H, m), 7.42-7.82 (5H, m). Mass: 532 (M+1)$^+$ Example 10

Synthesis of 5-(1-(3-chloro-2-fluorobenzoyl)-4-((6-(1H-pyrazol-3-ylamino)pyridin-2-yl)methyl)piperidin-4-yl)-1,3,4-oxadiazol-2(3H)-one trifluoroacetate

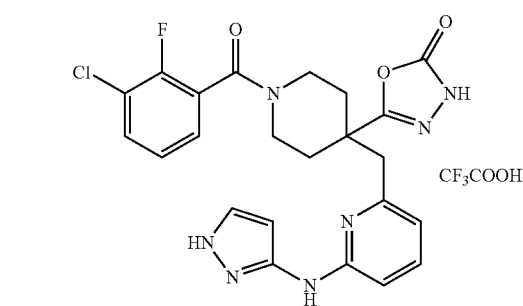 [SMILES: O=C(c1cccc(Cl)c1F)N1CCC(Cc2cccc(Nc3cc[nH]n3)n2)(c2n[nH]c(=O)o2)CC1 ; "CF3COOH"]

(1) Synthesis of 1-(tert-butoxycarbonyl)-4-((6-((1-tert-butyl-1H-pyrazol-5-yl)amino)pyridin-2-yl)methyl)piperidine-4-carboxylic acid

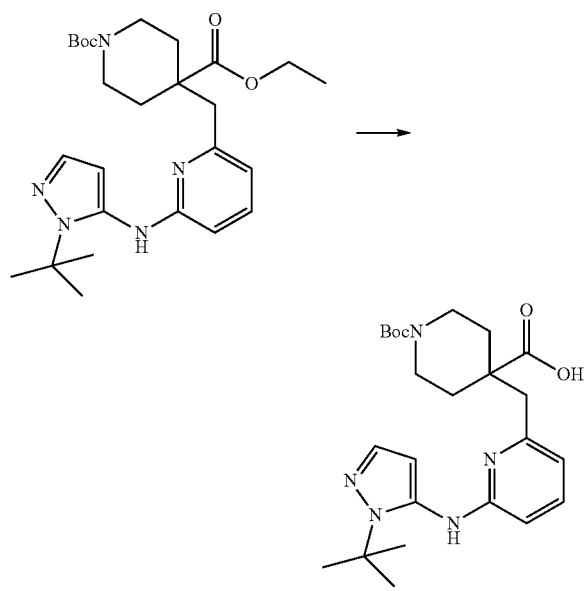

To a solution of 495 mg of 1-tert-butyl 4-ethyl 4-((6-((1-tert-butyl-1H-pyrazol-5-yl)amino)pyridin-2-yl)methyl)piperidine-1,4-dicarboxylate as obtained in the step of Example 4(3) in 5 ml of ethanol was added 1 ml of 5 M aqueous sodium hydroxide solution at room temperature, followed by stirring the reaction mixture at 60° C. overnight. The reaction mixture was cooled to room temperature, and concentrated in vacuo. The resulting residue was acidified with 5 M hydrochloric acid, and extracted with ethyl acetate. The ethyl acetate solution was dried over anhydrous magnesium sulfate, and filtered. The filtrate was concentrated in vacuo to give the title compound as a pale yellow oil.

(2) Synthesis of tert-butyl 4-((2-((benzyloxy)carbonyl)hydrazino)carbonyl)-4-((6-((1-tert-butyl-1H-pyrazol-5-yl)amino)pyridin-2-yl)methyl)piperidine-1-carboxylate

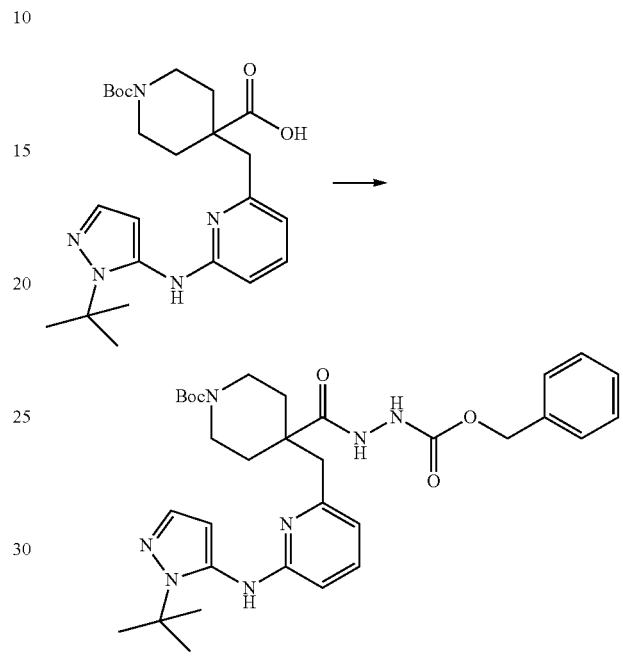

To a solution of 535 mg of 1-(tert-butoxycarbonyl)-4-((6-((1-tert-butyl-1H-pyrazol-5-yl)amino)pyridin-2-yl)methyl)piperidine-4-carboxylic acid in 10 ml of chloroform were added 214 mg of benzyl carbazate and 291 mg of 1-(3-dimethylaminopropyl)-3-ethylcarbodiimide hydrochloride at room temperature, followed by stirring the reaction mixture at room temperature for 2 hours. The reaction mixture was poured into water, and extracted with chloroform. The chloroform solution was dried over magnesium sulfate, and filtered. The filtrate was concentrated in vacuo. The resulting residue was purified by a silica gel column chromatography (eluent: hexane to hexane/ethyl acetate=10/1) to give the title compound as a pale brown solid.

(3) Synthesis of tert-butyl 4-((6-((1-tert-butyl-1H-pyrazol-5-yl)amino)pyridin-2-yl)methyl)-4-(hydrazinocarbonyl)piperidine-1-carboxylate

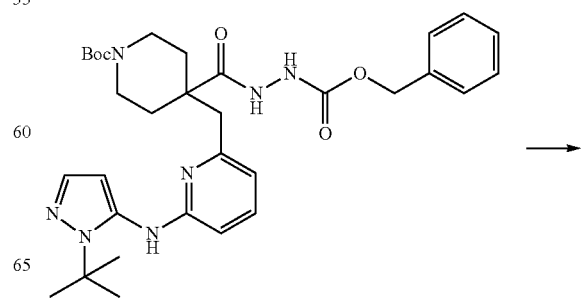

-continued

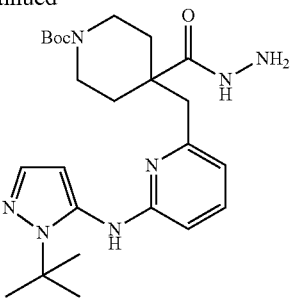

To a solution of 535 mg of tert-butyl 4-((2-((benzyloxy) carbonyl)hydrazino)carbonyl)-4-((6-((1-tert-butyl-1H-pyrazol-5-yl)amino)pyridin-2-yl)methyl)piperidine-1-carboxylate in 10 ml of methanol was added 200 mg of 20% palladium hydroxide on carbon, followed by stirring the reaction mixture at room temperature overnight under hydrogen atmosphere. Palladium catalyst was filtered off using Celite, washed with methanol, and the filtrate was concentrated in vacuo to give the title compound as a pale brown solid.

(4) Synthesis of tert-butyl 4-((6-((1-tert-butyl-1H-pyrazol-5-yl)amino)pyridin-2-yl)methyl)-4-(5-oxo-4,5-dihydro-1,3,4-oxadiazol-2-yl)piperidine-1-carboxylate

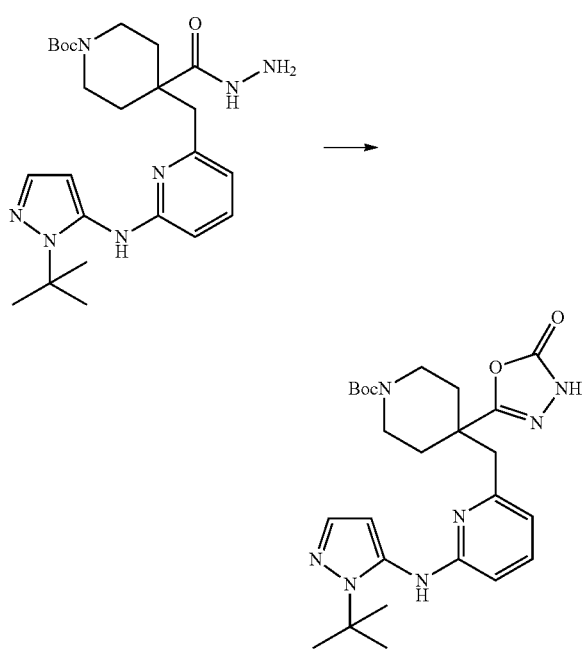

To a suspension of 378 mg of tert-butyl 4-((6-((1-tert-butyl-1H-pyrazol-5-yl)amino)pyridin-2-yl)methyl)-4-(hydrazinocarbonyl)piperidine-1-carboxylate in 10 ml of tetrahydrofuran was added 130 mg of 1,1'-carbonyldiimidazole at room temperature. After stirring at room temperature for 3 hours, 100 mg of 1,1'-carbonyldiimidazole was added at room temperature, followed by stirring at room temperature for 5 days. To the reaction mixture was added 10 ml of saturated aqueous sodium bicarbonate solution, followed by stirring the reaction mixture at room temperature for 30 minutes. The reaction mixture was poured into water, and extracted with ethyl acetate. The ethyl acetate solution was dried over anhydrous magnesium sulfate, and filtered. The filtrate was concentrated in vacuo. The resulting residue was purified by a silica gel column chromatography (eluent: hexane/ethyl acetate=20/1–1/2) to give the title compound as a pale yellow oil.

(5) Synthesis of 5-(4-((6-((1-tert-butyl-1H-pyrazol-5-yl)amino)pyridin-2-yl)methyl)piperidin-4-yl)-1,3,4-oxadiazol-2(3H)-one dihydrochloride

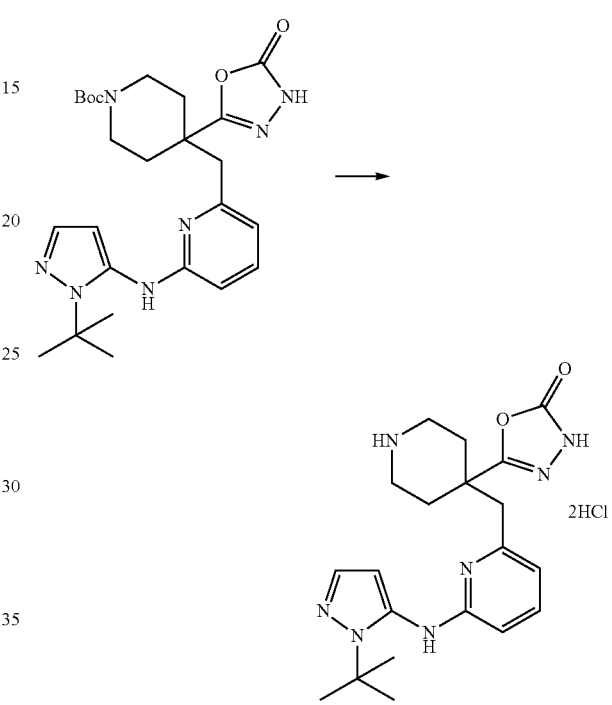

To a solution of 250 mg of tert-butyl 4-((6-((1-tert-butyl-1H-pyrazol-5-yl)amino)pyridin-2-yl)methyl)-4-(5-oxo-4,5-dihydro-1,3,4-oxadiazol-2-yl)piperidine-1-carboxylate in 4 ml of methanol was added 4 ml of 4 M hydrogen chloride in 1,4-dioxane at room temperature. The reaction mixture was stirred at room temperature for 1 hour, and concentrated in vacuo to give the title compound as a pale yellow solid.

(6) Synthesis of 5-(4-((6-((1-tert-butyl-1H-pyrazol-5-yl)amino)pyridin-2-yl)methyl)-1-(3-chloro-2-fluorobenzoyl)piperidin-4-yl)-1,3,4-oxadiazol-2(3H)-one

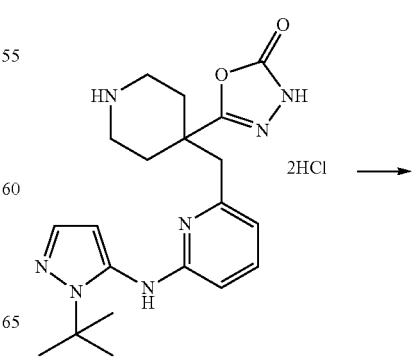

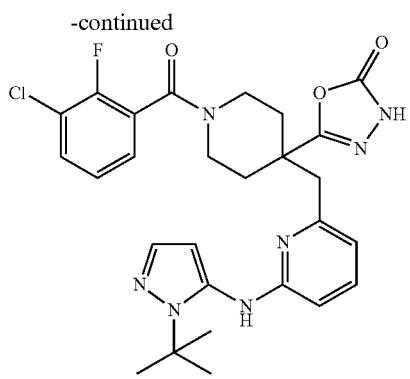

To a solution of 40 mg of 5-(4-((6-(((1-tert-butyl-1H-pyrazol-5-yl)amino)pyridin-2-yl)methyl)piperidin-4-yl)-1,3,4-oxadiazol-2(3H)-one dihydrochloride in 2 ml of pyridine were added 17.8 mg of 3-chloro-2-fluorobenzoic acid and 24.4 mg of 1-(3-dimethylaminopropyl)-3-ethylcarbodiimide hydrochloride at room temperature. The reaction mixture was stirred at room temperature overnight, followed by concentrating in vacuo. The reaction mixture was dissolved in ethyl acetate, and washed with water. The resulting ethyl acetate layer was dried over anhydrous magnesium sulfate, and filtered. The filtrate was concentrated in vacuo. The resulting residue was purified by a silica gel column chromatography (eluent: hexane to ethyl acetate) to give the title compound as a pale yellow oil.

(7) Synthesis of 5-(1-(3-chloro-2-fluorobenzoyl)-4-((6-(1H-pyrazol-3-ylamino)pyridin-2-yl)methyl)piperidin-4-yl)-1,3,4-oxadiazol-2(3H)-one trifluoroacetate

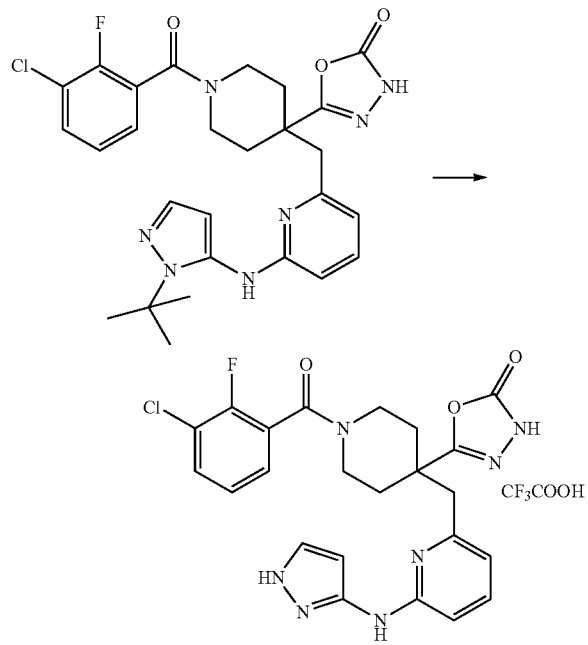

25.5 mg of 5-(4-((6-(((1-tert-butyl-1H-pyrazol-5-yl)amino)pyridin-2-yl)methyl)-1-(3-chloro-2-fluorobenzoyl)piperidin-4-yl)-1,3,4-oxadiazol-2(3H)-one was dissolved in 1 ml of formic acid at room temperature, followed by stirring the reaction mixture at 90° C. overnight. The reaction mixture was cooled to room temperature, and concentrated in vacuo. The resulting residue was purified by a reversed phase preparative liquid chromatography, followed by concentrating the obtained fraction in vacuo to give the title compound as a white solid.

$^1$H-NMR (CD$_3$OD) δ: 1.84-2.01 (2H, m), 2.12-2.26 (1H, m), 2.30-2.38 (1H, m), 3.06-3.17 (1H, m), 3.20-3.39 (3H, m), 3.48-3.56 (1H, m), 4.53-4.60 (1H, m), 6.15 (1H, d, J=2.4 Hz), 6.99 (1H, d, J=7.0 Hz), 7.19 (1H, d, J=9.0 Hz), 7.25-7.46 (2H, m), 7.61 (1H, dd, J=9.0, 7.4 Hz), 7.77 (1H, d, J=2.4 Hz), 8.02 (1H, dd, J=8.6, 7.4 Hz).

Mass: 498,500 (M+1)$^+$

Example 11

Synthesis of 5-(1-(2,3-difluorobenzoyl)-4-((6-(1H-pyrazol-3-ylamino)pyridin-2-yl)methyl)piperidin-4-yl)-1,3,4-oxadiazol-2(3H)-one trifluoroacetate

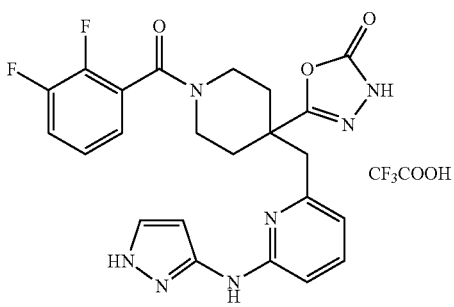

The title compound was obtained as a white solid in the same manner as in Example 10 using 2,3-difluorobenzoic acid, instead of 3-chloro-2-fluorobenzoic acid as used in the step of Example 10(6).

$^1$H-NMR (CD$_3$OD) δ: 1.82-2.01 (2H, m), 2.15-2.25 (1H, m), 2.31-2.38 (1H, m), 3.06-3.17 (1H, m), 3.20-3.40 (3H, m), 3.51-3.62 (1H, m), 4.53-4.62 (1H, m), 6.15 (1H, d, J=2.4 Hz), 6.99 (1H, d, J=7.0 Hz), 7.12-7.32 (3H, m), 7.40 (1H, q, J=8.2 Hz), 7.77 (1H, d, J=2.4 Hz), 8.03 (1H, dd, J=9.0, 7.4 Hz).

Mass: 482 (M+1)$^+$

Example 12

Synthesis of 5-(1-(phenylsulfonyl)-4-((6-(1H-pyrazol-3-ylamino)pyridin-2-yl)methyl)piperidin-4-yl)-1,3,4-oxadiazol-2(3H)-one trifluoroacetate

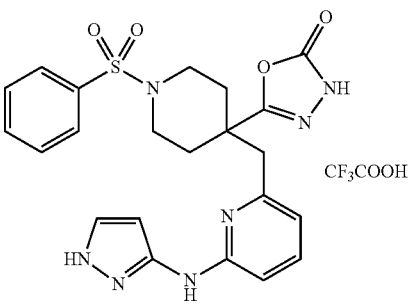 [SMILES: O=c1[nH]nc(C2(Cc3cccc(Nc4cc[nH]n4)n3)CCN(S(=O)(=O)c3ccccc3)CC2)o1 ; "CF3COOH"]

(1) Synthesis of 5-(4-((6-((1-tert-butyl-1H-pyrazol-5-yl)amino)pyridin-2-yl)methyl)-1-(phenylsulfonyl)piperidin-4-yl)-1,3,4-oxadiazol-2(3H)-one

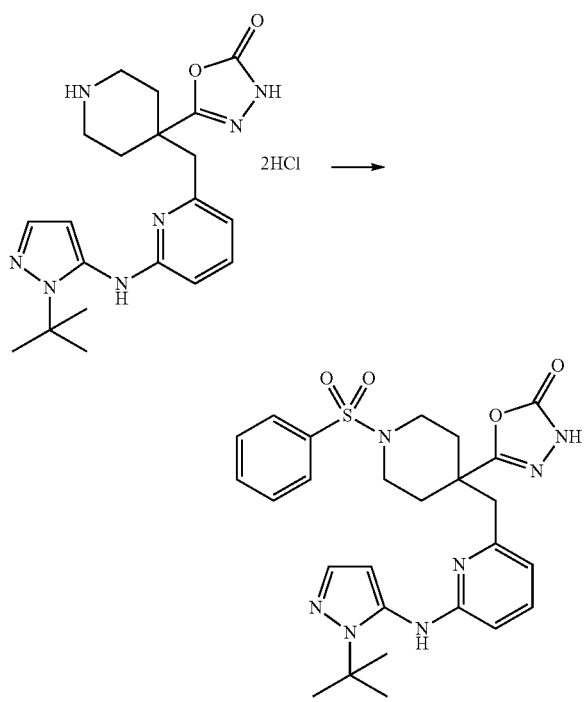

To a solution of 40 mg of 5-(4(((6((1-tert-butyl-1H-pyrazol-5-yl)amino)pyridin-2-yl)methyl)piperidin-4-yl)-1,3,4-oxadiazol-2(3H)-one dihydrochloride as obtained in the step of Example 10(5) in 4 ml of chloroform were added 0.059 ml of triethylamine and 0.013 ml of benzenesulfonyl chloride at room temperature. The reaction mixture was stirred at room temperature overnight, followed by concentrating in vacuo. To a solution of the resulting residue in 3 ml of methanol was added 117 mg of potassium carbonate at room temperature. The reaction mixture was stirred at room temperature for 1 h, poured into water, and extracted with ethyl acetate. The resulting ethyl acetate layer was dried over anhydrous magnesium sulfate, and filtered. The filtrate was concentrated in vacuo. The resulting residue was purified by a preparative thin-layer chromatography (Kieselgel™ 60F$_{254}$, Art5744 (Merck), hexane/ethyl acetate=1/2) to give the title compound as a pale yellow oil.

(2) Synthesis of 5-(1-(phenylsulfonyl)-4-((6-(1H-pyrazol-3-ylamino)pyridin-2-yl)methyl)piperidin-4-yl)-1,3,4-oxadiazol-2(3H)-one trifluoroacetate

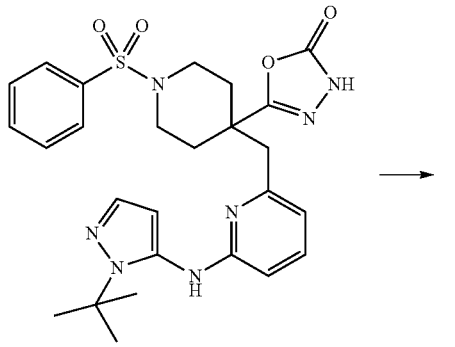

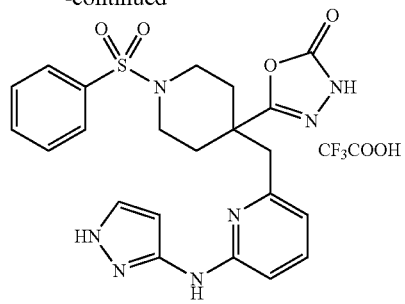

The title compound was obtained as a white solid in the same manner as in the step of Example 10(7) using 5-(4-((6-((1-tert-butyl-1H-pyrazol-5-yl)amino)pyridin-2-yl)methyl)-1-(phenylsulfonyl)piperidin-4-yl)-1,3,4-oxadiazol-2(3H)-one, instead of 5-(4-((6-((1-tert-butyl-1H-pyrazol-5-yl)amino)pyridin-2-yl)methyl)-1-(3-chloro-2-fluorobenzoyl)piperidin-4-yl)-1,3,4-oxadiazol-2(3H)-one as used in the step of Example 10(7).

$^1$H-NMR (CD$_3$OD) δ: 1.94-2.03 (2H, m), 2.24-2.32 (2H, m), 2.39-2.49 (2H, m), 3.23 (2H, s), 3.70-3.77 (2H, m), 6.14 (1H, d, J=2.4 Hz), 6.92 (1H, d, J=7.4 Hz), 7.15 (1H, d, J=9.0 Hz), 7.53-7.68 (3H, m), 7.71-7.78 (3H, m), 7.99 (1H, dd, J=9.0, 7.4 Hz).

Mass: 482 (M+1)$^+$

Example 13

Synthesis of 5-(1((2,3-dichlorophenyl)sulfonyl)-4((6-(1H-pyrazol-3-ylamino)pyridin-2-yl)methyl)piperidin-4-yl)-1,3,4-oxadiazol-2(3H)-one trifluoroacetate

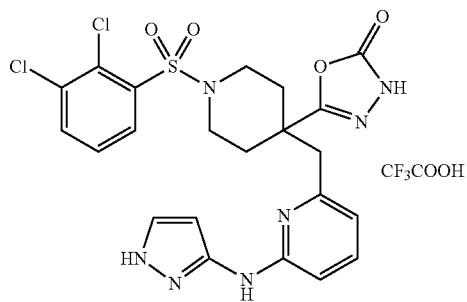 [SMILES: O=c1[nH]nc(C2(Cc3cccc(Nc4cc[nH]n4)n3)CCN(S(=O)(=O)c3cccc(Cl)c3Cl)CC2)o1 ; "CF3COOH"]

The title compound was obtained as a white solid in the same manner as in Example 12 using 2,3-dichlorobenzenesulfonyl chloride, instead of benzenesulfonyl chloride as used in the step of Example 12(1). $^1$H-NMR (CD$_3$OD) δ: 1.88-2.00 (2H, m), 2.23-2.32 (2H, m), 2.96-3.06 (2H, m), 3.28 (2H, s), 3.78-3.85 (2H, m), 6.15 (1H, d, J=2.4 Hz), 6.97 (1H, d, J=7.0 Hz), 7.17 (1H, d, J=9.0 Hz), 7.46 (1H, t, J=8.0 Hz), 7.76 (1H, d, J=2.4 Hz), 7.80 (1H, dd, J=8.2, 1.2 Hz), 7.97-8.05 (2H, m).

Mass: 550,552 (M+1)$^+$

Example 14

Synthesis of 5-(4-((6-(1H-pyrazol-3-ylamino)pyridin-2-yl)methyl)-1-((2-(trifluoromethyl)phenyl)sulfonyl)piperidin-4-yl)-1,3,4-oxadiazol-2(3H)-one trifluoroacetate

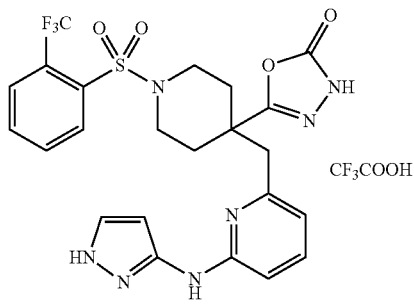 [SMILES: O=c1[nH]nc(C2(Cc3cccc(Nc4cc[nH]n4)n3)CCN(S(=O)(=O)c3ccccc3C(F)(F)F)CC2)o1 ; "CF3COOH"]

The title compound was obtained as a white solid in the same manner as in Example 12 using 2-(trifluoromethyl)benzenesulfonyl chloride, instead of benzenesulfonyl chloride as used in the step of Example 12(1).

$^1$H-NMR (CD$_3$OD) δ: 1.90-2.02 (2H, m), 2.25-2.33 (2H, m), 2.87-2.97 (2H, m), 3.28 (2H, s), 3.76-3.85 (2H, m), 6.15 (1H, d, J=2.8 Hz), 6.97 (1H, d, J=7.4 Hz), 7.17 (1H, d, J=8.6 Hz), 7.74-7.84 (3H, m), 7.92-8.11 (3H, m).

Mass: 550 (M+1)$^+$

Example 15

Synthesis of 5-(1-(3-chloro-2-fluorobenzoyl)-4-((6-((5-methyl-1H-pyrazol-3-yl)amino)pyridin-2-yl)methyl)piperidin-4-yl)-1,3,4-oxadiazol-2(3H)-one

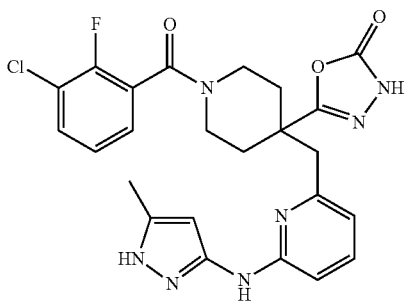 [SMILES: Cc1cc(Nc2cccc(CC3(c4n[nH]c(=O)o4)CCN(C(=O)c4cccc(Cl)c4F)CC3)n2)n[nH]1]

(1) Synthesis of 1-tert-butyl 4-ethyl 4-((6-((1-tert-butyl-3-methyl-1H-pyrazol-5-yl)amino)pyridin-2-yl)methyl)piperidine-1,4-dicarboxylate

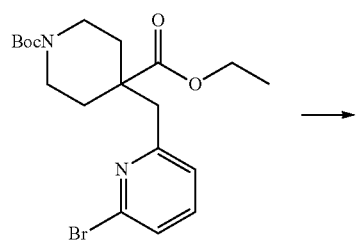

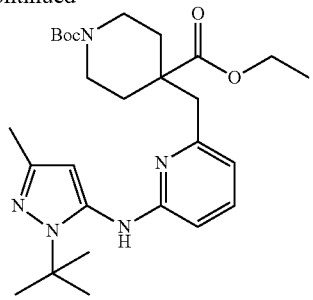

The title compound was obtained as a pale brown oil in the same manner as in the step of Example 4(3) using 1-tert-butyl-3-methyl-1H-pyrazol-5-amine, instead of 1-tert-butyl-1H-pyrazol-5-amine as used in the step of Example 4(3).

(2) Synthesis of 5-(4-((6-((1-tert-butyl-3-methyl-1H-pyrazol-5-yl)amino)pyridin-2-yl)methyl)piperidin-4-yl)-1,3,4-oxadiazol-2(3H)-one dihydrochloride

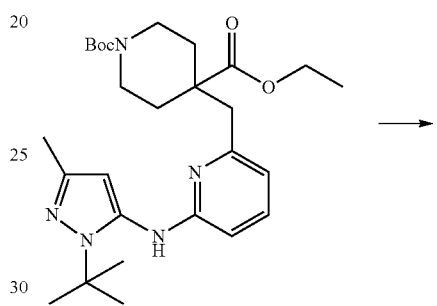

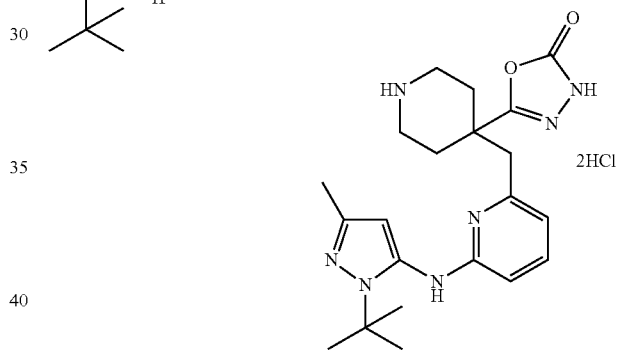

The title compound was obtained as a pale yellow solid in the same manner as in the steps of Example 10(1) to 10(5) using 1-tert-butyl 4-ethyl 4-((6-((1-tert-butyl-3-methyl-1H-pyrazol-5-yl)amino)pyridin-2-yl)methyl)piperidine-1,4-dicarboxylate, instead of 1-tert-butyl 4-ethyl 4-((6-((1-tert-butyl-1H-pyrazol-5-yl)amino)pyridin-2-yl)methyl)piperidine-1,4-dicarboxylate as used in the step of Example 10(1).

(3) Synthesis of 5-(4-((6-((1-tert-butyl-3-methyl-1H-pyrazol-5-yl)amino)pyridin-2-yl)methyl)-1-(3-chloro-2-fluorobenzoyl)piperidin-4-yl)-1,3,4-oxadiazol-2(3H)-one

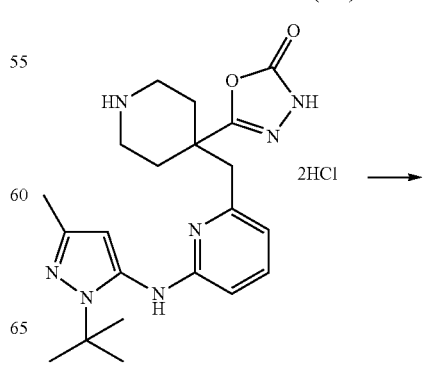

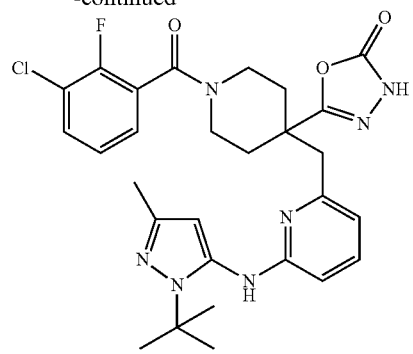

The title compound was obtained as a pale yellow oil in the same manner as in the step of Example 10(6) using 5-(4-((6-((1-tert-butyl-3-methyl-1H-pyrazol-5-yl)amino)pyridin-2-yl)methyl)piperidin-4-yl)-1,3,4-oxadiazol-2(3H)-one dihydrochloride, instead of 5-(4-((6-((1-tert-butyl-1H-pyrazol-5-yl)amino)pyridin-2-yl)methyl)piperidin-4-yl)-1,3,4-oxadiazol-2(3H)-one dihydrochloride as used in the step of Example 10(6).

(4) Synthesis of 5-(1-(3-chloro-2-fluorobenzoyl)-4-((6-((5-methyl-1H-pyrazol-3-yl)amino)pyridin-2-yl)methyl)piperidin-4-yl)-1,3,4-oxadiazol-2(3H)-one

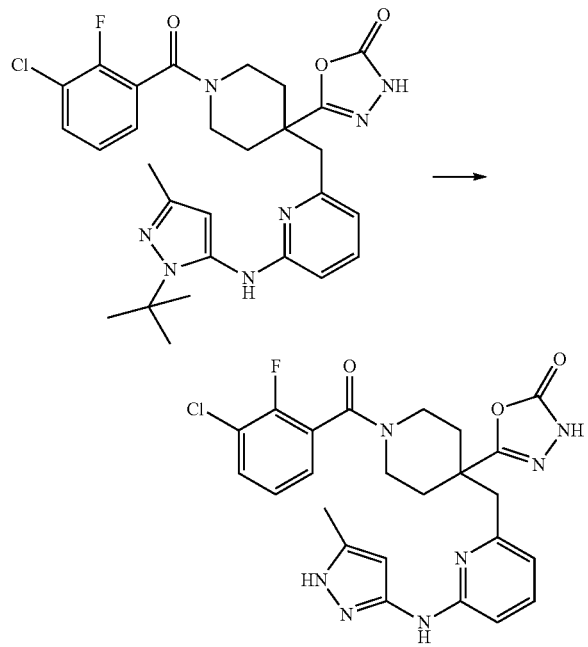

The title compound was obtained as a pale yellow solid in the same manner as in the step of Example 9(5) using 5-(4-((6-((1-tert-butyl-3-methyl-1H-pyrazol-5-yl)amino)pyridin-2-yl)methyl)-1-(3-chloro-2-fluorobenzoyl)piperidin-4-yl)-1,3,4-oxadiazol-2(3H)-one, instead of 5-(4-((6-((1-tert-butyl-1H-pyrazol-5-yl)amino)pyridin-2-yl)methyl)-1-(2-fluoro-3-(trifluoromethyl)benzoyl)piperidin-4-yl)-1,3,4-oxadiazol-2(3H)-one as used in the step of Example 9(5).

$^1$H-NMR (CDCl$_3$) δ: 1.40-2.35 (7H, m), 2.74-3.54 (5H, m), 4.01-4.55 (1H, m), 5.14-6.03 (1H, m), 6.45-7.50 (7H, m).
Mass: 510,512 (M+1)$^+$

Example 16

Synthesis of 5-(1-(2,3-difluorobenzoyl)-4-((6-((5-methyl-1H-pyrazol-3-yl)amino)pyridin-2-yl)methyl)piperidin-4-yl)-1,3,4-oxadiazol-2(3H)-one

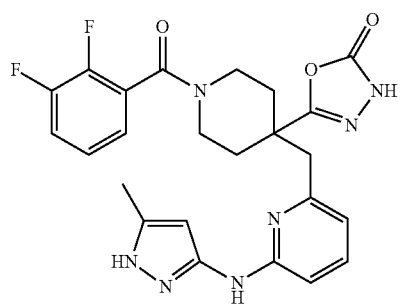 [SMILES: Cc1cc(Nc2cccc(CC3(c4n[nH]c(=O)o4)CCN(C(=O)c4cccc(F)c4F)CC3)n2)n[nH]1]

The title compound was obtained as a pale yellow solid in the same manner as in Example 15 using 2,3-difluorobenzoic acid, instead of 3-chloro-2-fluorobenzoic acid as used in the step of Example 15(3).

$^1$H-NMR (CDCl$_3$) δ: 1.40-2.35 (7H, m), 2.72-3.55 (5H, m), 4.01-4.55 (1H, m), 5.20-6.03 (1H, m), 6.46-7.53 (7H, m).
Mass: 496 (M+1)$^+$

Example 17

Synthesis of 5-(1-(3-chloro-2-fluorobenzoyl)-4-((4-phenyl-6-(1H-pyrazol-3-ylamino)pyridin-2-yl)methyl)piperidin-4-yl)-1,3,4-oxadiazol-2(3H)-one

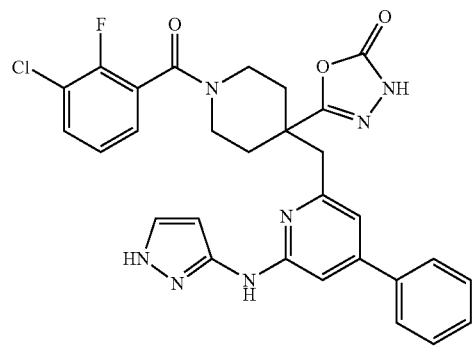 [SMILES: O=C(c1cccc(Cl)c1F)N1CCC(Cc2cc(-c3ccccc3)cc(Nc3cc[nH]n3)n2)(c2n[nH]c(=O)o2)CC1]

(1) Synthesis of (4-(benzyloxy)-6-chloropyridin-2-yl)methanol

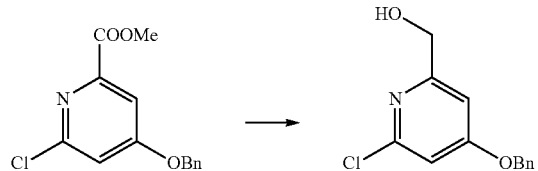 [SMILES: COC(=O)c1cc(OCc2ccccc2)cc(Cl)n1 ; OCc1cc(OCc2ccccc2)cc(Cl)n1]

To a solution of 500 mg of methyl 4-(benzyloxy)-6-chloropyridine-2-carboxylate (WO2006/046734, page 123, Example 116(5)) in 3 ml of tetrahydrofuran was added 78 mg of lithium aluminum hydride at room temperature, followed by stirring the reaction mixture at room temperature for 2 hours. The reaction mixture was diluted with ethyl acetate, and washed with saturated aqueous ammonium chloride solution, water and brine. The ethyl acetate solution was dried over anhydrous magnesium sulfate, and filtered. The filtrate was concentrated in vacuo to give the title compound as a pale yellow solid.

(2) Synthesis of 1-tert-butyl 4-ethyl 4((4-(benzyloxy)-6((1-tert-butyl-1H-pyrazol-5-yl)amino)pyridin-2-yl)methyl)piperidine-1,4-dicarboxylate

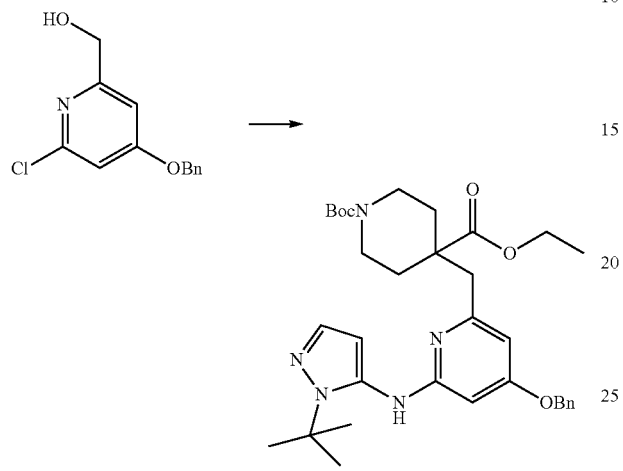

The title compound was obtained as a pale brown oil in the same manner as in the steps of Example 4(1) to 4(3) using (4-(benzyloxy)-6-chloropyridin-2-yl)methanol, instead of (6-bromo-pyridin-2-yl)methanol as used in the step of Example 4(1).

(3) Synthesis of 1-tert-butyl 4-ethyl 4-((6-((1-tert-butyl-1H-pyrazol-5-yl)amino)-4-hydroxypyridin-2-yl)methyl)piperidine-1,4-dicarboxylate

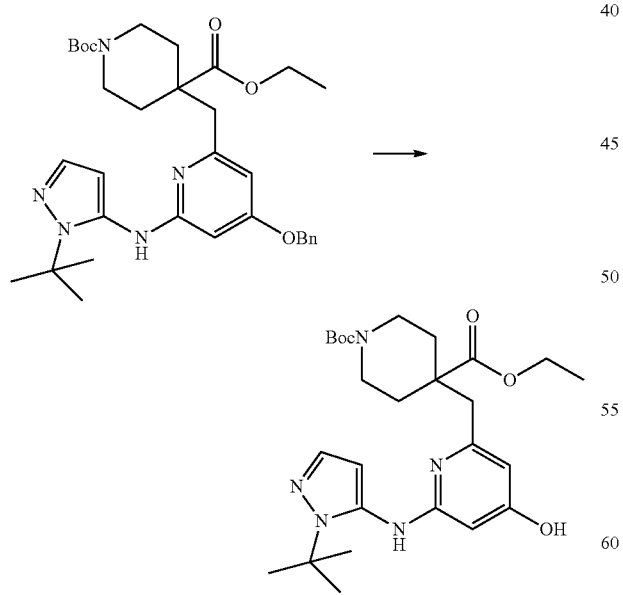

To a solution of 1 g of 1-tert-butyl 4-ethyl 4-((4-(benzyloxy)-6-((1-tert-butyl-1H-pyrazol-5-yl)amino)pyridin-2-yl)methyl)piperidine-1,4-dicarboxylate in 10 ml of tetrahydrofuran and 10 ml of methanol was added 300 mg of 20% palladium hydroxide on carbon, followed by stirring the reaction mixture at room temperature for 2 hours under hydrogen atmosphere. Palladium catalyst was filtered off using Celite, washed with methanol, and the filtrate was concentrated in vacuo to give the title compound as a pale brown solid.

(4) Synthesis of 1-tert-butyl 4-ethyl 4-((6-((1-tert-butyl-1H-pyrazol-5-yl)amino)-4-(((trifluoromethyl)sulfonyl)oxy)pyridin-2-yl)methyl)piperidine-1,4-dicarboxylate

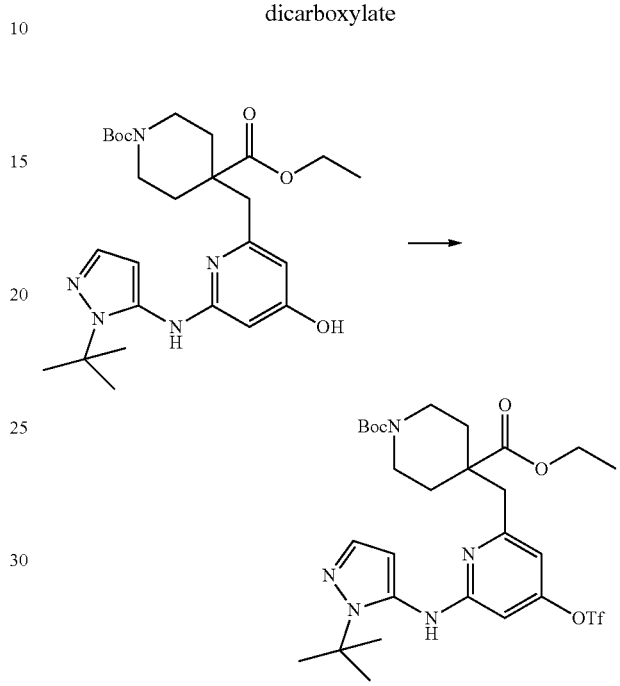

To a solution of 848 mg of 1-tert-butyl 4-ethyl 4((6-((1-tert-butyl-1H-pyrazol-5-yl)amino)-4-hydroxypyridin-2-yl)methyl)piperidine-1,4-dicarboxylate in 10 ml of chloroform were added 1.18 ml of N,N-diisopropylethylamine and 0.57 ml of trifluoromethanesulfonic anhydride at 0° C., followed by stirring the reaction mixture at 0° C. for 30 minutes. The reaction mixture was poured into water, and extracted with ethyl acetate. The ethyl acetate solution was washed with water and brine, dried over anhydrous magnesium sulfate, and filtered. The filtrate was concentrated in vacuo. The resulting residue was purified by a silica gel column chromatography (eluent: chloroform to chloroform/methanol=9/1) to give the title compound as a pale yellow solid.

(5) Synthesis of 1-tert-butyl 4-ethyl 4-((6-((1-tert-butyl-1H-pyrazol-5-yl)amino)-4-phenylpyridin-2-yl)methyl)piperidine-1,4-dicarboxylate

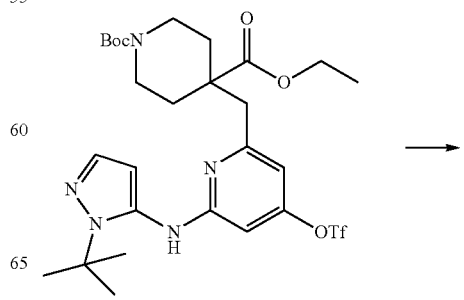

-continued

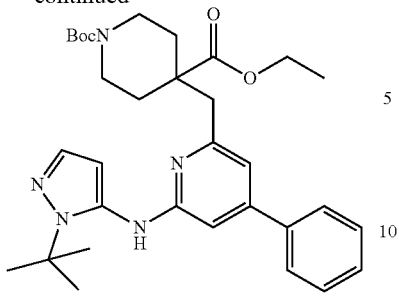

A mixture of 300 mg of 1-tert-butyl 4-ethyl 4-((6-(((1-tert-butyl-1H-pyrazol-5-yl)amino)-4-((((trifluoromethyl)sulfonyl)oxy)pyridin-2-yl)methyl)piperidine-1,4-dicarboxylate, 87 mg of phenylboronic acid, 69.3 mg of (1,1'-bis(diphenylphosphino)ferrocene)dichloropalladium(II), 201 mg of potassium phosphate, 3 ml of 1,4-dioxane and 0.3 ml of water was stirred at 100° C. overnight, followed by cooling to room temperature. The reaction mixture was diluted with ethyl acetate. An insoluble matter was filtered off using Celite, and washed with ethyl acetate. The filtrate was washed with water and brine, dried over anhydrous magnesium sulfate, and filtered. The filtrate was concentrated in vacuo. The resulting residue was purified by a silica gel column chromatography (eluent: chloroform to chloroform/methanol=9/1) to give the title compound as a pale yellow solid.

(6) Synthesis of 5-(1-(3-chloro-2-fluorobenzoyl)-4-((4-phenyl-6-(1H-pyrazol-3-ylamino)pyridin-2-yl)methyl)piperidin-4-yl)-1,3,4-oxadiazol-2(3H)-one

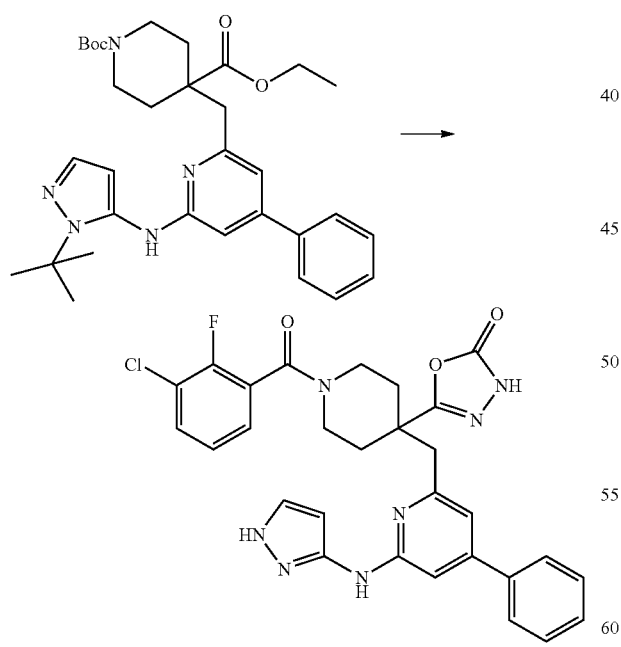

The title compound was obtained as a white solid in the same manner as in the steps of Example 4(4), (5) and Example 9(1) to 9(5) using 5-(1-(3-chloro-2-fluorobenzoyl)-4-((4-phenyl-6-(1H-pyrazol-3-ylamino)pyridin-2-yl)methyl)piperidin-4-yl)-1,3,4-oxadiazol-2(3H)-one, instead of 1-tert-butyl 4-ethyl 4-((6-(((1-tert-butyl-1H-pyrazol-5-yl)amino)pyridin-2-yl)methyl)piperidine-1,4-dicarboxylate as used in the step of Example 4(4).

$^{1}$H-NMR (DMSO-d$_{6}$) δ: 1.72-2.20 (4H, m), 2.97-3.48 (6H, m), 4.23-4.29 (1H, m), 6.35 (1H, brs), 6.68 (1H, s), 7.25-7.69 (10H, m), 9.20 (1H, brs), 12.04 (1H, brs).

Mass: 574,576 (M+1)$^{+}$

Example 18

Synthesis of 1-(3-chloro-2-fluorobenzoyl)-4-((4-methyl-6-(1H-pyrazol-3-ylamino)pyrimidin-2-yl)methyl)piperidine-4-carboxamide trifluoroacetate

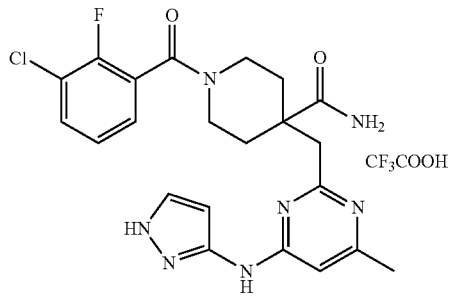 [SMILES: Cc1cc(Nc2cc[nH]n2)nc(CC2(C(N)=O)CCN(C(=O)c3cccc(Cl)c3F)CC2)n1 ; "CF3COOH"]

The title compound was obtained as a white solid in the same manner as in the steps of Example 4(1) to (3), (6) and Example 6 using (4-((1-tert-butyl-1H-pyrazol-5-yl)amino)-6-methylpyrimidin-2-yl)methanol (WO2007/126126, page 54, Example 1(3)), instead of (6-bromo-pyridin-2-yl)methanol as used in the step of Example 4(1).

$^{1}$H-NMR (CD$_{3}$OD) δ: 1.90-2.39 (4H, m), 2.48 (3H, s), 2.97-3.20 (3H, m), 3.41-3.55 (2H, m), 4.14-4.31 (1H, m), 5.95-6.20 (2H, m), 6.62-6.88 (1H, m), 7.22-7.39 (2H, m), 7.53-7.75 (3H, m).

Mass: 472,474 (M+1)$^{+}$

Example 19

Synthesis of 5-(4-((6-(1H-pyrazol-3-ylamino)pyridin-2-yl)methyl)-1-(2,2,2-trifluoro-1-(3-(trifluoromethyl)phenyl)ethyl)piperidin-4-yl)-1,3,4-oxadiazol-2(3H)-one trifluoroacetate

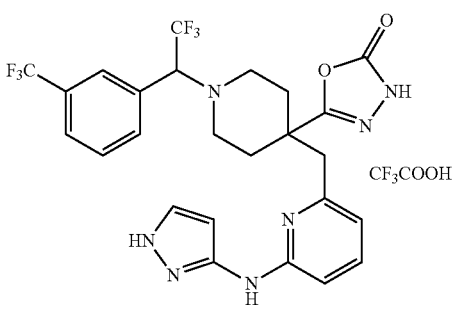 [SMILES: O=c1[nH]nc(C2(Cc3cccc(Nc4cc[nH]n4)n3)CCN(C(c3cccc(C(F)(F)F)c3)C(F)(F)F)CC2)o1 ; "CF3COOH"]

(1) Synthesis of ethyl 1-(2,2,2-trifluoro-1-(3-(trifluoromethyl)phenyl)ethyl)piperidine-4-carboxylate

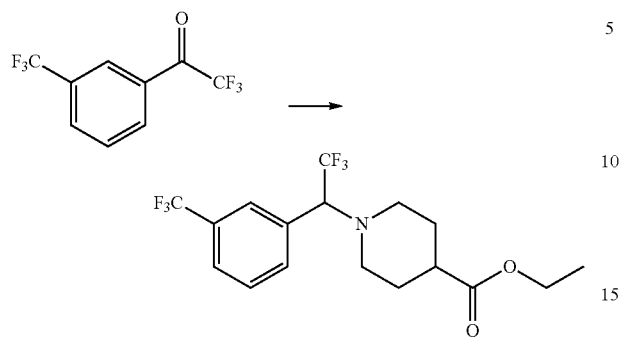

To a solution of 0.355 ml of 2,2,2-trifluoro-1-(3-(trifluoromethyl)phenyl)ethanone in 12 ml of dichloromethane were added 0.32 ml of ethyl isonipecotate, 0.58 ml of triethylamine and 1.05 ml of a toluene solution containing 1 M titanium(IV) chloride at room temperature, followed by stirring the reaction mixture at room temperature overnight. To the reaction mixture was added a solution of 392 mg of sodium cyanoborohydride in 5 ml of methanol at room temperature, followed by stirring the reaction mixture at room temperature for 6 hours. Ethyl acetate and saturated aqueous sodium bicarbonate solution were added to the reaction mixture. An insoluble matter was filtered off using Celite. The ethyl acetate layer was separated, washed with brine, dried over anhydrous magnesium sulfate, and filtered. The filtrate was concentrated in vacuo. The resulting residue was purified by a silica gel column chromatography (eluent: hexane to hexane/ethyl acetate=4/1) to give the title compound as a yellow oil.

(2) Synthesis of 5-(4-((6-(1H-pyrazol-3-ylamino)pyridin-2-yl)methyl)-1-(2,2,2-trifluoro-1-(3-(trifluoromethyl)phenyl)ethyl)piperidin-4-yl)-1,3,4-oxadiazol-2(3H)-one trifluoroacetate

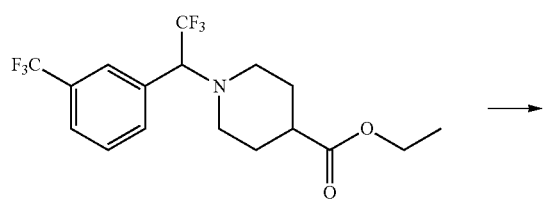

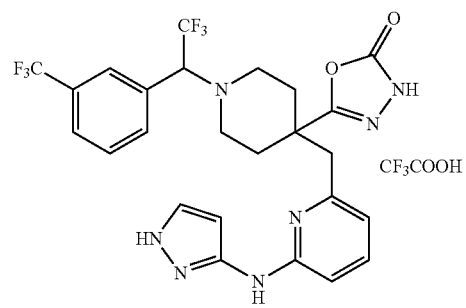

The title compound was obtained as a white solid in the same manner as in the steps of Example 4(2), (3) and Example 9(1) to 9(5) using ethyl 1-(2,2,2-trifluoro-1-(3-(trifluoromethyl)phenyl)ethyl)piperidine-4-carboxylate, instead of 1-tert-butyl 4-ethyl piperidine-1,4-dicarboxylate as used in the step of Example 4(2).

$^1$H-NMR (CD$_3$OD) δ: 1.89-2.00 (2H, m), 2.13-2.30 (3H, m), 2.52 (1H, brt, J=11.2 Hz), 2.92 (1H, brd, J=12.4 Hz), 2.99 (1H, brd, J=12.4 Hz), 3.22 (2H, brs), 4.48 (1H, q, J=8.8 Hz), 6.13 (1H, d, J=2.4 Hz), 6.94 (1H, d, J=7.2 Hz), 7.16 (1H, d, J=8.8 Hz), 7.56-7.63 (1H, m), 7.66-7.71 (3H, m), 7.75 (1H, d, J=2.4 Hz), 8.00 (1H, dd, J=8.8, 7.2 Hz).

Mass: 568 (M+1)$^+$

INDUSTRIAL APPLICABILITY

The compound of the invention is characterized in that it has cell growth inhibitory action as well as synergistic action with other antitumor agents, based on excellent Aurora A selective inhibitory action, and thus it is expected as a useful antitumor agent in the field of pharmaceuticals.

The invention claimed is:

1. A compound which is:
   (a) 1-(3-chloro-2-fluorobenzoyl)-4-((6-(1H-pyrazol-3-ylamino)pyridin-2-yl)methyl)piperidin-4-ol;
   (b) 5-(1-(2-fluoro-3-(trifluoromethyl)benzoyl)-4-((6-(1H-pyrazol-3-ylamino)pyridin-2-yl)methyl)piperidin-4-yl)-1,3,4-oxadiazol-2(3H)-one;
   (c) 5-(1-(3-chloro-2-fluorobenzoyl)-4-((6-(1H-pyrazol-3-ylamino)pyridin-2-yl)methyl)piperidin-4-yl)-1,3,4-oxadiazol-2(3H)-one;
   (d) 5-(4-((6-(1H-pyrazol-3-ylamino)pyridin-2-yl)methyl)-1-((2-(trifluoromethyl)phenyl)sulfonyl)piperidin-4-yl)-1,3,4-oxadiazol-2(3H)-one;
   (e) 5-(1-(3-chloro-2-fluorobenzoyl)-4-((4-phenyl-6-(1H-pyrazol-3-ylamino)pyridin-2-yl)methyl)piperidin-4-yl)-1,3,4-oxadiazol-2(3H)-one; or
   (f) 5-(4-((6-(1H-pyrazol-3-ylamino)pyridin-2-yl)methyl)-1-(2,2,2-trifluoro-1-(3-(trifluoromethyl)phenyl)ethyl)piperidin-4-yl)-1,3,4-oxadiazol-2(3H)-one;
or a pharmaceutically acceptable salt or ester thereof.

2. A pharmaceutical composition comprising, together with pharmaceutically acceptable carrier or diluent, at least one compound according to claim 1 as active ingredient.

3. A combined preparation for simultaneous, separate, or sequential administration in the treatment of cancer, comprising two separate preparations:
   (i) a preparation comprising, together with a pharmaceutically acceptable carrier or diluent, a compound according to claim 1; and
   (ii) a preparation comprising, together with a pharmaceutically acceptable carrier or diluent, one antitumor agent selected from the group consisting of antitumor alkylating agents, antitumor antimetabolites, antitumor antibiotics, plant-derived antitumor agents, antitumor platinum-complex compounds, antitumor camphothecin derivatives, antitumor tyrosine kinase inhibitors, monoclonal antibodies, interferons, biological response modifiers, and other antitumor agents or a pharmaceutically acceptable salt thereof, wherein:
      the antitumor alkylating agents are nitrogen mustard N-oxide, cyclophosphamide, ifosfamide, melphalan, busulfan, mitobronitol, carboquone, thiotepa, ranimustine, nimustine, temozolomide, and carmustine;
      the antitumor antimetabolites are methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine, and pemetrexed disodium;
      the antitumor antibiotics are actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus, and valrubicin;
      the plant-derived antitumor agents are vincristine, vinblastine, vindeshine, etoposide, sobuzoxane, docetaxel, paclitaxel, and vinorelbine;
      the antitumor platinum-complex compounds are cisplatin, carboplatin, nedaplatin, and oxaliplatin;
      the antitumor camphothecin derivatives are irinotecan, topotecan, and camphothecin;
      the antitumor tyrosine kinase inhibitors are gefitinib, imatinib, sorafenib, sunitinib, dasatinib, and erlotinib;
      the monoclonal antibodies are cetuximab, rituximab, bevacizumab, alemtuzumab, and trastuzumab;
      the interferons are interferon α, interferon α-2a, interferon α-2b, interferon β, interferon γ-1a, and interferon γ-n1,
      the biological response modifiers are krestin, lentinan, sizofuran, picibanil, or ubenimex, and
      the other antitumor agents are mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

4. The combined preparation according to claim 3 wherein one of or both of the two separate preparations is/are oral preparation(s).

5. The combined preparation according to claim 3 which is further combined with at least one preparation comprising, together with a pharmaceutically acceptable carrier or diluent, an antitumor agent selected from the group consisting of antitumor alkylating agents, antitumor antimetabolites, antitumor antibiotics, plant-derived antitumor agents, antitumor platinum-complex compounds, antitumor camphothecin derivatives, antitumor tyrosine kinase inhibitors, monoclonal antibodies, interferons, biological response modifiers, and other antitumor agents, wherein the definition of each antitumor agent is the same as defined in claim 3, or a pharmaceutically acceptable salt thereof.

6. The combined preparation according to claim 3 wherein: among the combined preparation,
   (i) one is a preparation which comprises, together with a pharmaceutically acceptable carrier or diluent,
      (a) 1-(3-chloro-2-fluorobenzoyl)-4-((6-(1H-pyrazol-3-ylamino)pyridin-2-yl)methyl)piperidin-4-ol;
      (b) 5-(1-(2-fluoro-3-(trifluoromethyl)benzoyl)-4-((6-(1H-pyrazol-3-ylamino)pyridin-2-yl)methyl)piperidin-4-yl)-1,3,4-oxadiazol-2(3H)-one;

(c) 5-(1-(3-chloro-2-fluorobenzoyl)-4-((6-(1H-pyrazol-3-ylamino)pyridin-2-yl)methyl)piperidin-4-yl)-1,3,4-oxadiazol-2(3H)-one;

(d) 5-(4-((6-(1H-pyrazol-3-ylamino)pyridin-2-yl)methyl)-1-((2-(trifluoromethyl)phenyl)sulfonyl)piperidin-4-yl)-1,3,4-oxadiazol-2(3H)-one;

(e) 5-(1-(3-chloro-2-fluorobenzoyl)-4-((4-phenyl-6-(1H-pyrazol-3-ylamino)pyridin-2-yl)methyl)piperidin-4-yl)-1,3,4-oxadiazol-2(3H)-one; or (f) 5-(4-((6-(1H-pyrazol-3-ylamino)pyridin-2-yl)methyl)-1-(2,2,2-trifluoro-1-(3-(trifluoromethyl)phenyl)ethyl)piperidin-4-yl)-1,3,4-oxadiazol-2(3H)-one;

or a pharmaceutically acceptable salt or ester thereof; and
(ii) the other is a preparation which comprises, together with a pharmaceutically acceptable carrier or diluent, paclitaxel or docetaxel.

7. A pharmaceutical composition comprising, together with a pharmaceutically acceptable carrier or diluent, a compound according to claim 1, or a pharmaceutically acceptable salt thereof; and an antitumor agent selected from the group consisting of antitumor alkylating agents, antitumor antimetabolites, antitumor antibiotics, plant-derived antitumor agents, antitumor platinum-complex compounds, antitumor campthotecin derivatives, antitumor tyrosine kinase inhibitors, monoclonal antibodies, biological response modifiers, and other antitumor agents, wherein the definition of each antitumor agent is the same as defined in claim 3, or a pharmaceutically acceptable salt thereof.

8. The pharmaceutical composition according to claim 7, wherein a compound according to claim 1 is the following:

(a) 1-(3-chloro-2-fluorobenzoyl)-4-((6-(1H-pyrazol-3-ylamino)pyridin-2-yl)methyl)piperidin-4-ol;

(b) 5-(1-(2-fluoro-3-(trifluoromethyl)benzoyl)-4-((6-(1H-pyrazol-3-ylamino)pyridin-2-yl)methyl)piperidin-4-yl)-1,3,4-oxadiazol-2(3H)-one;

(c) 5-(1-(3-chloro-2-fluorobenzoyl)-4-((6-(1H-pyrazol-3-ylamino)pyridin-2-yl)methyl)piperidin-4-yl)-1,3,4-oxadiazol-2(3H)-one;

(d) 5-(4-((6-(1H-pyrazol-3-ylamino)pyridin-2-yl)methyl)-1-((2-(trifluoromethyl)phenyl)sulfonyl)piperidin-4-yl)-1,3,4-oxadiazol-2(3H)-one;

(e) 5-(1-(3-chloro-2-fluorobenzoyl)-4-((4-phenyl-6-(1H-pyrazol-3-ylamino)pyridin-2-yl)methyl)piperidin-4-yl)-1,3,4-oxadiazol-2(3H)-one; or (f) 5-(4-((6-(1H-pyrazol-3-ylamino)pyridin-2-yl)methyl)-1-(2,2,2-trifluoro-1-(3-(trifluoromethyl)phenyl)ethyl)piperidin-4-yl)-1,3,4-oxadiazol-2(3H)-one;

or a pharmaceutically acceptable salt or ester thereof; and the antitumor agent is paclitaxel or docetaxel.

\* \* \* \* \*

SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Completely Synthetic Amino Acid Sequence
<221> NAME/KEY: AMIDATION
<222> LOCATION: (1)...(1)
<223> OTHER INFORMATION: Xaa = 5-FAM-gamma-aminobutyric acid
      5-FAM = 5-carboxyfluorescein

<400> SEQUENCE: 1

```
-continued

Xaa Ala Leu Arg Arg Ala Ser Leu Gly
 1               5

<210> SEQ ID NO 2
<211> LENGTH: 7
<212> TYPE: PRT
<213> ORGANISM: Artificial Sequence
<220> FEATURE:
<223> OTHER INFORMATION: Completely Synthetic Amino Acid Sequence

<400> SEQUENCE: 2

Leu Arg Arg Ala Ser Leu Gly
 1               5
```